(12) United States Patent
O'Neil et al.

(10) Patent No.: US 8,071,103 B2
(45) Date of Patent: Dec. 6, 2011

(54) PHARMACEUTICAL COMPOSITION COMPRISING A HUMAN GLP-1 MIMETIBODY

(75) Inventors: Karyn T. O'Neil, Media, PA (US); Kristen Picha, Malvern, PA (US)

(73) Assignee: Centocor, Inc., Radnor, PA (US)

( * ) Notice: Subject to any disclaimer, the term of this patent is extended or adjusted under 35 U.S.C. 154(b) by 574 days.

(21) Appl. No.: 11/779,316

(22) Filed: Jul. 18, 2007

(65) Prior Publication Data

US 2008/0044411 A1    Feb. 21, 2008

Related U.S. Application Data

(60) Provisional application No. 60/831,704, filed on Jul. 18, 2006.

(51) Int. Cl.
*A61K 39/00* (2006.01)
*A61K 38/00* (2006.01)
*C07K 16/00* (2006.01)

(52) U.S. Cl. .......... 424/178.1; 530/308; 530/387.1; 514/1.1

(58) Field of Classification Search .......... None
See application file for complete search history.

(56) References Cited

U.S. PATENT DOCUMENTS

| | | | |
|---|---|---|---|
| 4,946,778 A | 8/1990 | Ladner et al. | |
| 5,118,666 A | 6/1992 | Habener | |
| 5,428,130 A | 6/1995 | Capon et al. | |
| 5,512,549 A | 4/1996 | Chen et al. | |
| 5,545,618 A | 8/1996 | Buckley et al. | |
| 5,908,626 A | 6/1999 | Chang et al. | |
| 5,977,071 A | 11/1999 | Galloway et al. | |
| 6,406,697 B1 | 6/2002 | Capon et al. | |
| 2004/0053370 A1* | 3/2004 | Glaesner et al. | 435/69.7 |
| 2004/0096935 A1* | 5/2004 | Shi et al. | 435/69.1 |

FOREIGN PATENT DOCUMENTS

| | | |
|---|---|---|
| EP | 1 355 942 B1 | 10/2003 |
| EP | 1 408 050 | 4/2004 |
| EP | 1 559 724 | 8/2005 |
| WO | WO 98/08871 | 3/1998 |
| WO | WO 00/69911 | 11/2000 |
| WO | WO 01/98331 A | 12/2001 |
| WO | WO 2004/002424 A | 1/2004 |
| WO | WO 2005/005604 A2 | 6/2004 |
| WO | WO 2005/097175 A | 10/2005 |

OTHER PUBLICATIONS

Adelhorst, et al., "Structure-Activity Studies of Glucagon-like Peptide-1," The Journal of Biological Chemistry, 269(9): 6275-6278 (1994).
Chou, et al., "Conformational Parameters for Amino Acids in Helical, β-Sheet, and Random Coil Regions Calculated from Proteins," Biochemistry, 13(2): 211-222 (1974).
Marqusee, et al., "Helix stabilization by Glu$^-$ . . . Lys$^+$ salt bridges in short peptides of *de novo* design," Proceedings of the National Academy of Sciences USA, 84: 8898-8902 (1987).
Maxfield, et al., "The Effect of Neighboring Charges on the Helix Forming Ability of Charged Amino Acids in Proteins," Macromolecules, 8(4): 491-493 (1975).
Thornton, et al., "Structure of Glucagon-like peptide (7-36) Amide in a Dodecylphosphocholine Micelle as Determined by 2D NMR," Biochemistry, 33: 3532-3539 (1994).
Sarmay, et al, "Mapping and Comparison of the Interaction Sites on The Fc Region of IgG Responsible for Triggering Antibody Dependent Cellular Cytotoxicity (ADCC) Through Different Types of Human Fcγ Receptor," Molecular Immunology, 29(5): 633-639 (1992).
Bird, et al., "Single-Chain Antigen-Binding Proteins," Science, 242: 423-426 (1988).
Parker, et al., "Structure-function analysis of a series of glucagon-like peptide-1 analogs," Journal of Peptide Research, 52: 398-409 (1998).
Kim, et al., "FT-IR and Near-Infared FT-Raman Studies of the Secondary Structure of Insulinotropin in the solid State: α-Helix to β-Sheet Conversion Induced by Phenol and/or by High Shear Force," Journal of Pharmaceutical Sciences, 83(8): 1175-1180 (1994).
PCT International Search Report dated Jul. 4, 2008.

\* cited by examiner

*Primary Examiner* — Gyan Chandra
(74) *Attorney, Agent, or Firm* — Kirk Baumeister

(57) ABSTRACT

The present invention relates to at least one improved human GLP-1 mimetibody or specified portion or variant, including isolated nucleic acids that encode at least one GLP-1 mimetibody or specified portion or variant, GLP-1 mimetibody or specified portion or variants, vectors, host cells, transgenic animals or plants, and methods of making and using thereof, including therapeutic compositions, methods and devices.

2 Claims, 27 Drawing Sheets

FIG. 1A

```
SIGNAL SEQUENCE..................................................................................
Met Ala Trp Val Trp Thr Leu Leu Phe Leu Met Ala Ala Ala Gln
ATG GCT TGG GTG TGG ACC TTG CTA TTC CTG ATG GCG GCC GCC CAA

.................... GLP-1 ..........................................................................
Ser Ile Gln Ala His Ala Glu Gly Thr Phe Thr Ser Asp Val Ser
AGT ATA CAG GCC CAT GCT GAA GGG ACC TTT ACT AGT GAT GTA AGT

Ser Tyr Leu Glu Gly Gln Ala Ala Lys Glu Phe Ile Glu Trp Leu
TCT TAT TTG GAA GGC CAA GCT GCC AAG GAA TTC ATT GAA TGG CTG

.................... LINKER ................................................ VH ...............
Val Lys Gly Arg Gly Gly Gly Ser Gly Gly Gly Ser Gly Thr Leu
GTG AAA GGC CGA GGA GGT GGA TCC GGT GGA GGC TCC GGT ACC TTA

.................... HINGE ..........................................................................
Val Thr Asn Ser Ser Glu Pro Lys Ser Cys Asp Lys Thr His Thr
GTC ACC AAC TCC TCA GAG CCC AAA TCT TGT GAC AAA ACT CAC ACG

.................... CH2 ............................................................................
Cys Pro Pro Cys Pro Ala Pro Glu Leu Leu Gly Gly Pro Ser Val
TGC CCA CCG TGC CCA GCA CCT GAA CTC CTG GGG GGA CCG TCA GTC

Phe Leu Phe Pro Pro Lys Pro Lys Asp Thr Leu Met Ile Ser Arg
TTC CTC TTC CCC CCA AAA CCC AAG GAC ACC CTC ATG ATC TCC CGG

Thr Pro glu Val Thr Cys Val Val Val Asp Val Ser His Glu Asp
ACC CCT GAG GTC ACA TGC GTG GTG GTG GAC GTG AGC CAC GAA GAC Pro Glu Val Lys Phe Asn Trp Tyr Val Asp Gly Val Glu Val His
CCT GAG GTC AAG TTC AAC TGG TAC GTG GAC GGC GTG GAG GTG CAT Asn Ala Lys Thr Lys Pro Arg Glu Glu Gln Tyr Asn Ser Thr tyr
AAT GCC AAG ACA AAG CCG CGG GAG GAG CAG TAC AAC AGC ACG TAC Arg Val Val Ser Val Leu Thr Val Leu His Gln Asp Trp Leu Asn
CGG GTG GTC AGC GTC CTC ACC GTC CTG CAC CAG GAC TGG CTG AAT
```

FIG. 1B

```
Gly Lys Glu Tyr Lys Cys Lys Val Ser Asn Lys Ala Leu Pro Ala
GGC AAG GAG TAC AAG TGC AAG GTC TCC AAC AAA GCC CTC CCA GCC

................ CH3 ........................
Pro Ile Glu Lys Thr Ile Ser Lys Ala Lys Gly Gln Pro Arg Glu
CCC ATC GAG AAA ACC ATC TCC AAA GCC AAA GGG CAG CCC CGA GAA

Pro Gln Val Tyr Thr Leu Pro Pro Ser Arg Asp Glu Leu Thr Lys
CCA CAG GTG TAC ACC CTG CCC CCA TCC CGG GAT GAG CTG ACC AAG

Asn Gln Val Ser Leu Thr Cys Leu Val Lys Gly Phe Tyr Pro Ser
AAC CAG GTC AGC CTG ACC TGC CTG GTC AAA GGC TTC TAT CCC AGC

Asp Ile Ala Val Glu Trp Glu Ser Asn Gly Gln Pro Glu Asn Asn
GAC ATC GCC GTG GAG TGG GAG AGC AAT GGG CAG CCG GAG AAC AAC

Tyr Lys Thr Thr Pro Pro Val Leu Asp Ser Asp Gly Ser Phe Phe
TAC AAG ACC ACG CCT CCC GTG CTG GAC TCC GAC GGC TCC TTC TTC

Leu Tyr Ser Lys Leu Thr Val Asp Lys Ser Arg Trp Gln Gln Gly
CTC TAC AGC AAG CTC ACC GTG GAC AAG AGC AGG TGG CAG CAG GGG

Asn Val Phe Ser Cys Ser Val Met His Glu Ala Leu His Asn His
AAC GTC TTC TCA TGC TCC GTG ATG CAT GAG GCT CTG CAC AAC CAC

........... STOP
Tyr Thr Gln Lys Ser Leu Ser Leu Ser Pro Gly Lys
TAC ACG CAG AAG AGC CTC TCC CTG TCT CCG GGT AAA TGA
```

Insulin Release in Rin M cells treated with GLP-1 and Exendin 4
n=3

Insulin Release in Rin M cells in presence of GLP-1 mmb's n=3

```
                              SEQUENCE LISTING

<160> NUMBER OF SEQ ID NOS: 64

<210> SEQ ID NO 1
<211> LENGTH: 31
<212> TYPE: PRT
<213> ORGANISM: Artificial sequence
<220> FEATURE:
<223> OTHER INFORMATION: GLP-1 variants
<220> FEATURE:
<221> NAME/KEY: MOD_RES
<222> LOCATION: (2)
<223> OTHER INFORMATION: Ala, Gly, Ser, Thr, Leu, Ile, Val, Glu, Asp or
      Lys
<220> FEATURE:
<221> NAME/KEY: MOD_RES
<222> LOCATION: (3)
<223> OTHER INFORMATION: Glu, Asp or Lys
<220> FEATURE:
<221> NAME/KEY: MOD_RES
<222> LOCATION: (6)
<223> OTHER INFORMATION: Phe, His, Trp or Tyr
<220> FEATURE:
<221> NAME/KEY: MOD_RES
<222> LOCATION: (7)
<223> OTHER INFORMATION: Thr or Asn
<220> FEATURE:
<221> NAME/KEY: MOD_RES
<222> LOCATION: (8)
<223> OTHER INFORMATION: Ala, Gly, Ser, Thr, Leu, Ile, Val, Glu, Asp or
      Lys
<220> FEATURE:
<221> NAME/KEY: MOD_RES
<222> LOCATION: (9)
<223> OTHER INFORMATION: Glu or Asp
<220> FEATURE:
<221> NAME/KEY: MOD_RES
<222> LOCATION: (10)
<223> OTHER INFORMATION: Val, Gln, His, Glu, or Lys
<220> FEATURE:
<221> NAME/KEY: MOD_RES
```

```
<222> LOCATION: (12)
<223> OTHER INFORMATION: Ala, Gly, Ser, Thr, Leu, Ile, Val, Glu, Asp or
      Lys
<220> FEATURE:
<221> NAME/KEY: MOD_RES
<222> LOCATION: (14)
<223> OTHER INFORMATION: Leu, Gln, His, Glu, or Lys
<220> FEATURE:
<221> NAME/KEY: MOD_RES
<222> LOCATION: (16)
<223> OTHER INFORMATION: Ala, Gly, Ser, Thr, Leu, Ile, Val, Gln, Asn,
      Arg, Cys, Glu, Asp or Lys
<220> FEATURE:
<221> NAME/KEY: MOD_RES
<222> LOCATION: (17)
<223> OTHER INFORMATION: Gln, Asn, Arg, His, Glu, Asp or Lys
<220> FEATURE:
<221> NAME/KEY: MOD_RES
<222> LOCATION: (18)
<223> OTHER INFORMATION: Ala, Gly, Ser, Thr, Leu, Ile, Val, Glu, Asp or
      Lys
<220> FEATURE:
<221> NAME/KEY: MOD_RES
<222> LOCATION: (19)
<223> OTHER INFORMATION: Ala, Gly, Ser, Thr, Leu, Ile, Val, Glu, Asp or
      Lys
<220> FEATURE:
<221> NAME/KEY: MOD_RES
<222> LOCATION: (21)
<223> OTHER INFORMATION: Glu, Leu, Ala, His, Phe, Tyr, Trp, Arg, Gln,
      Thr, Ser, Gly, Asp or Lys
<220> FEATURE:
<221> NAME/KEY: MOD_RES
<222> LOCATION: (23)
<223> OTHER INFORMATION: Ala, Val, Leu, or Glu
<220> FEATURE:
<221> NAME/KEY: MOD_RES
<222> LOCATION: (27)
<223> OTHER INFORMATION: Val, Gln, His, Glu, or Lys
<220> FEATURE:
<221> NAME/KEY: MOD_RES
<222> LOCATION: (28)
<223> OTHER INFORMATION: Lys, Asn, Arg, His, Glu, or Asp
<220> FEATURE:
<221> NAME/KEY: MOD_RES
<222> LOCATION: (30)
<223> OTHER INFORMATION: Arg, His, Thr, Ser, Trp, Tyr, Phe, Glu, Asp or
      Lys
<220> FEATURE:
<221> NAME/KEY: MOD_RES
<222> LOCATION: (31)
<223> OTHER INFORMATION: Gly, Ala, Ser, Thr, Leu, Ile, Val, Arg, Trp,
      Tyr, Phe, Pro, His, Glu, Asp or Lys

<400> SEQUENCE: 1

His Xaa Xaa Gly Thr Xaa Xaa Xaa Xaa Xaa Ser Xaa Tyr Xaa Glu Xaa
 1               5                  10                  15

Xaa Xaa Xaa Lys Xaa Phe Xaa Ala Trp Leu Xaa Xaa Gly Xaa Xaa
                20                  25                  30

<210> SEQ ID NO 2
<211> LENGTH: 278
<212> TYPE: PRT
<213> ORGANISM: Artificial Sequence
<220> FEATURE:
<223> OTHER INFORMATION: fusion protein of GLP-1 variants-linker 3-J
      region-hinge H1-Fc
<220> FEATURE:
<221> NAME/KEY: MOD_RES
<222> LOCATION: (10)..(10)
<223> OTHER INFORMATION: Gln, Glu, Lys, His or Ala
<220> FEATURE:
<221> NAME/KEY: MOD_RES
<222> LOCATION: (12)..(13)
<223> OTHER INFORMATION: Gln, Glu, Lys, His or Ala
<220> FEATURE:
<221> NAME/KEY: MOD_RES
```

```
<222> LOCATION: (19)..(19)
<223> OTHER INFORMATION: Variable amino acid
<220> FEATURE:
<221> NAME/KEY: MOD_RES
<222> LOCATION: (24)..(24)
<223> OTHER INFORMATION: Gln, Glu, Lys or Ala
<220> FEATURE:
<221> NAME/KEY: MOD_RES
<222> LOCATION: (27)..(27)
<223> OTHER INFORMATION: Gln, Glu, Lys, His or Ala
<220> FEATURE:
<221> NAME/KEY: MOD_RES
<222> LOCATION: (44)..(44)
<223> OTHER INFORMATION: Asn or Gln

<400> SEQUENCE: 2

His Ala Glu Gly Thr Phe Thr Ser Asp Xaa Ser Xaa Xaa Leu Glu Gly
1               5                   10                  15

Gln Ala Xaa Lys Glu Phe Ile Xaa Trp Leu Xaa Lys Gly Arg Gly Gly
            20                  25                  30

Gly Ser Gly Gly Gly Ser Gly Thr Leu Val Thr Xaa Ser Ser Glu Pro
        35                  40                  45

Lys Ser Cys Asp Lys Thr His Thr Cys Pro Pro Cys Pro Ala Pro Glu
50                  55                  60

Leu Leu Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser His Glu Asp Pro Glu Val Lys Phe Asn Trp Tyr Val Asp Gly
            100                 105                 110

Val Glu Val His Asn Ala Lys Thr Lys Pro Arg Glu Glu Gln Tyr Asn
        115                 120                 125

Ser Thr Tyr Arg Val Val Ser Val Leu Thr Val Leu His Gln Asp Trp
    130                 135                 140

Leu Asn Gly Lys Glu Tyr Lys Cys Lys Val Ser Asn Lys Ala Leu Pro
145                 150                 155                 160

Ala Pro Ile Glu Lys Thr Ile Ser Lys Ala Lys Gly Gln Pro Arg Glu
                165                 170                 175

Pro Gln Val Tyr Thr Leu Pro Pro Ser Arg Asp Glu Leu Thr Lys Asn
            180                 185                 190

Gln Val Ser Leu Thr Cys Leu Val Lys Gly Phe Tyr Pro Ser Asp Ile
        195                 200                 205

Ala Val Glu Trp Glu Ser Asn Gly Gln Pro Glu Asn Asn Tyr Lys Thr
    210                 215                 220

Thr Pro Pro Val Leu Asp Ser Asp Gly Ser Phe Phe Leu Tyr Ser Lys
225                 230                 235                 240

Leu Thr Val Asp Lys Ser Arg Trp Gln Gln Gly Asn Val Phe Ser Cys
                245                 250                 255

Ser Val Met His Glu Ala Leu His Asn His Tyr Thr Gln Lys Ser Leu
            260                 265                 270

Ser Leu Ser Pro Gly Lys
        275

<210> SEQ ID NO 3
<211> LENGTH: 837
<212> TYPE: DNA
<213> ORGANISM: Artificial Sequence
<220> FEATURE:
<223> OTHER INFORMATION: cDNA encoding a fusion protein of
      GLP-1 variants-linker 3-J region-hinge H1-Fc
<220> FEATURE:
```

<221> NAME/KEY: modified_base
<222> LOCATION: (28)..(30)
<223> OTHER INFORMATION: This region may encompass any codon encoding
       Gln, Glu, Lys, His or Ala
<220> FEATURE:
<221> NAME/KEY: modified_base
<222> LOCATION: (37)..(39)
<223> OTHER INFORMATION: This region may encompass any codon encoding
       Gln, Glu, Lys, His or Ala
<220> FEATURE:
<221> NAME/KEY: modified_base
<222> LOCATION: (40)..(42)
<223> OTHER INFORMATION: This region may encompass any codon encoding
       Gln, Glu, Lys, His or Ala
<220> FEATURE:
<221> NAME/KEY: modified_base
<222> LOCATION: (70)..(72)
<223> OTHER INFORMATION: This region may encompass any codon encoding
       Gln, Glu, Lys, His or Ala
<220> FEATURE:
<221> NAME/KEY: modified_base
<222> LOCATION: (79)..(81)
<223> OTHER INFORMATION: This region may encompass any codon encoding
       Gln, Glu, Lys, His or Ala
<220> FEATURE:
<221> NAME/KEY: modified_base
<222> LOCATION: (130)..(132)
<223> OTHER INFORMATION: This region may encompass any codon encoding
       Asn or Gln

<400> SEQUENCE: 3

```
catgctgaag ggaccttcac tagtgatnnn agttctnnnn nngaaggcca agctgccaag      60
gaattcattn nntggctgnn naaaggccga ggaggtggat ccggtggagg ctccggtacc     120
ttagtcaccn nntcctcaga gcccaaatct tgtgacaaaa ctcacacgtg cccaccgtgc     180
ccagcacctg aactcctggg gggaccgtca gtcttcctct tccccccaaa acccaaggac     240
accctcatga tctcccggac ccctgaggtc acatgcgtgg tggtggacgt gagccacgaa     300
gaccctgagg tcaagttcaa ctggtacgtg gacggcgtgg aggtgcataa tgccaagaca     360
aagccgcggg aggagcagta caacagcacg taccgggtgg tcagcgtcct caccgtcctg     420
caccaggact ggctgaatgg caaggagtac aagtgcaagg tctccaacaa agccctccca     480
gcccccatcg agaaaaccat ctccaaagcc aagggcagc ccgagaacc acaggtgtac      540
accctgcccc catcccggga tgagctgacc aagaaccagg tcagcctgac ctgcctggtc     600
aaaggcttct atcccagcga catcgccgtg gagtgggaga gcaatgggca gccggagaac     660
aactacaaga ccacgcctcc cgtgctggac tccgacggct ccttcttcct ctacagcaag     720
ctcaccgtgg acaagagcag gtggcagcag gggaacgtct tctcatgctc cgtgatgcat     780
gaggctctgc acaaccacta cacgcagaag agcctctccc tgtctccggg taaatga       837
```

<210> SEQ ID NO 4
<211> LENGTH: 275
<212> TYPE: PRT
<213> ORGANISM: Artificial Sequence
<220> FEATURE:
<223> OTHER INFORMATION: fusion protein of
       GLP-1 variant-linker 3-J region-Hinge H3-Fc

<400> SEQUENCE: 4

```
His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly Gly
                20                  25                  30

Gly Ser Gly Gly Gly Ser Gly Thr Leu Val Thr Asn Ser Ser Glu Ser
            35                  40                  45
```

-continued

```
            Lys Tyr Gly Pro Pro Cys Pro Pro Cys Pro Ala Pro Glu Ala Ala Gly
                50                  55                  60

Gly Pro Ser Val Phe Leu Phe Pro Pro Lys Pro Lys Asp Thr Leu Met
             65                  70                  75                  80

Ile Ser Arg Thr Pro Glu Val Thr Cys Val Val Val Asp Val Ser Gln
                                85                  90                  95

Glu Asp Pro Glu Val Gln Phe Asn Trp Tyr Val Asp Gly Val Glu Val
                           100                 105                 110

His Asn Ala Lys Thr Lys Pro Arg Glu Glu Gln Phe Asn Ser Thr Tyr
                       115                 120                 125

Arg Val Val Ser Val Leu Thr Val Leu His Gln Asp Trp Leu Asn Gly
                   130                 135                 140

Lys Glu Tyr Lys Cys Lys Val Ser Asn Lys Gly Leu Pro Ser Ser Ile
            145                 150                 155                 160

Glu Lys Thr Ile Ser Lys Ala Lys Gly Gln Pro Arg Glu Pro Gln Val
                            165                 170                 175

Tyr Thr Leu Pro Pro Ser Gln Glu Glu Met Thr Lys Asn Gln Val Ser
                        180                 185                 190

Leu Thr Cys Leu Val Lys Gly Phe Tyr Pro Ser Asp Ile Ala Val Glu
                    195                 200                 205

Trp Glu Ser Asn Gly Gln Pro Glu Asn Asn Tyr Lys Thr Thr Pro Pro
                210                 215                 220

Val Leu Asp Ser Asp Gly Ser Phe Phe Leu Tyr Ser Arg Leu Thr Val
            225                 230                 235                 240

Asp Lys Ser Arg Trp Gln Glu Gly Asn Val Phe Ser Cys Ser Val Met
                            245                 250                 255

His Glu Ala Leu His Asn His Tyr Thr Gln Lys Ser Leu Ser Leu Ser
                        260                 265                 270

Leu Gly Lys
                    275

<210> SEQ ID NO 5
            <211> LENGTH: 828
            <212> TYPE: DNA
            <213> ORGANISM: Artificial Sequence
            <220> FEATURE:
            <223> OTHER INFORMATION: cDNA encoding fusion protein of
                  GLP-1 variant-linker 3-J region-Hinge H3-Fc

<400> SEQUENCE: 5
catgctgaag ggacctttac tagtgatgta agttcttatt tggaaggcca agctgccaag      60
gaattcattg aatggctggt gaaaggccga ggaggtggat ccggtggagg ctccggtacc     120
ttagtcacca actcctcaga gtccaaatat ggtcccccat gcccaccatg cccggcgcct     180
gaggccgccg ggggaccatc agtcttcctg ttccccccaa aacccaagga cactctcatg     240
atctcccgga cccctgaggt cacgtgcgtg gtggtggacg tgagccagga agaccccgag     300
gtccagttca actggtacgt ggatggcgtg gaggtgcata atgccaagac aaagccgcgg     360
gaggagcagt tcaacagcac gtaccgtgtg gtcagcgtcc tcaccgtcct gcaccaggac     420
tggctgaacg gcaaggagta caagtgcaag gtctccaaca aaggcctccc gtcctccatc     480
gagaaaacca tctccaaagc caagggcag cctcgagagc cacaggtgta cccctgccc      540 ccatcccagg aggagatgac caagaaccag gtcagcctga cctgcctggt caaaggcttc     600
taccccagcg acatcgccgt ggagtgggag agcaatgggc agccggagaa caactacaag     660
accacgcctc ccgtgctgga ctccgacggc tccttcttcc tctacagcag gctaaccgtg     720
```

```
gacaagagca ggtggcagga ggggaatgtc ttctcatgct ccgtgatgca tgaggctctg    780
cacaaccact acacacagaa aagcttgtcc ctgtctctgg gtaaatga               828
```

```
<210> SEQ ID NO 6
<211> LENGTH: 30
<212> TYPE: PRT
<213> ORGANISM: Artificial sequence
<220> FEATURE:
<223> OTHER INFORMATION: GLP-1 variants
<220> FEATURE:
<221> NAME/KEY: MOD_RES
<222> LOCATION: (2)
<223> OTHER INFORMATION: Ala, Gly or Ser
<220> FEATURE:
<221> NAME/KEY: MOD_RES
<222> LOCATION: (3)
<223> OTHER INFORMATION: Glu or Asp
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (6)
<223> OTHER INFORMATION: Phe, His, Trp or Tyr
<220> FEATURE:
<221> NAME/KEY: MOD_RES
<222> LOCATION: (7)
<223> OTHER INFORMATION: Thr or Asn
<220> FEATURE:
<221> NAME/KEY: MOD_RES
<222> LOCATION: (8)
<223> OTHER INFORMATION: Ala, Ser or Thr
<220> FEATURE:
<221> NAME/KEY: MOD_RES
<222> LOCATION: (9)
<223> OTHER INFORMATION: Glu or Asp
<220> FEATURE:
<221> NAME/KEY: MOD_RES
<222> LOCATION: (10)
<223> OTHER INFORMATION: Val, Gln, His, Glu or Lys
<220> FEATURE:
<221> NAME/KEY: MOD_RES
<222> LOCATION: (12)
<223> OTHER INFORMATION: Ser or Lys
<220> FEATURE:
<221> NAME/KEY: MOD_RES
<222> LOCATION: (13)
<223> OTHER INFORMATION: Tyr, Gln, His, Glu or Lys
<220> FEATURE:
<221> NAME/KEY: MOD_RES
<222> LOCATION: (14)
<223> OTHER INFORMATION: Leu, Gln, His, Glu or Lys
<220> FEATURE:
<221> NAME/KEY: MOD_RES
<222> LOCATION: (16)
<223> OTHER INFORMATION: Gly, Ala, Glu or Asp
<220> FEATURE:
<221> NAME/KEY: MOD_RES
<222> LOCATION: (17)
<223> OTHER INFORMATION: Gln or Glu
<220> FEATURE:
<221> NAME/KEY: MOD_RES
<222> LOCATION: (18)
<223> OTHER INFORMATION: Ala or Lys
<220> FEATURE:
<221> NAME/KEY: MOD_RES
<222> LOCATION: (19)
<223> OTHER INFORMATION: Ala, Leu, Ile, Val or Met
<220> FEATURE:
<221> NAME/KEY: MOD_RES
<222> LOCATION: (21)
<223> OTHER INFORMATION: Glu or Leu
<220> FEATURE:
<221> NAME/KEY: MOD_RES
<222> LOCATION: (23)
<223> OTHER INFORMATION: Ala, Val, Ile, Leu or Glu
<220> FEATURE:
```

```
<221> NAME/KEY: MOD_RES
<222> LOCATION: (24)
<223> OTHER INFORMATION: Ala, Gln, His, Glu or Lys
<220> FEATURE:
<221> NAME/KEY: MOD_RES
<222> LOCATION: (27)
<223> OTHER INFORMATION: Val, Gln, His, Glu or Lys
<220> FEATURE:
<221> NAME/KEY: MOD_RES
<222> LOCATION: (28)
<223> OTHER INFORMATION: Lys or Asn
<220> FEATURE:
<221> NAME/KEY: MOD_RES
<222> LOCATION: (30)
<223> OTHER INFORMATION: Arg or Glu

<400> SEQUENCE: 6

His Xaa Xaa Gly Xaa Xaa Xaa Xaa Xaa Ser Xaa Xaa Xaa Glu Xaa
1               5                   10                  15

Xaa Xaa Xaa Lys Xaa Phe Xaa Xaa Trp Leu Xaa Xaa Gly Xaa
            20                  25                  30

<210> SEQ ID NO 7
<211> LENGTH: 63
<212> TYPE: PRT
<213> ORGANISM: Artificial sequence
<220> FEATURE:
<223> OTHER INFORMATION: Fusion protein of GLP-1 variant-Linker 3-J
      region-Hinge

<400> SEQUENCE: 7

His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly Gly
            20                  25                  30

Gly Ser Gly Gly Gly Ser Gly Thr Leu Val Thr Asn Ser Ser Glu Ser
        35                  40                  45

Lys Tyr Gly Pro Pro Cys Pro Pro Cys Pro Ala Pro Glu Ala Ala
    50                  55                  60

<210> SEQ ID NO 8
<211> LENGTH: 63
<212> TYPE: PRT
<213> ORGANISM: Artificial sequence
<220> FEATURE:
<223> OTHER INFORMATION: Fusion protein of GLP-1 variant-Linker-J
      region-Hinge

<400> SEQUENCE: 8

His Gly Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly Gly
            20                  25                  30

Gly Ser Gly Gly Gly Ser Gly Thr Leu Val Thr Asn Ser Ser Glu Ser
        35                  40                  45

Lys Tyr Gly Pro Pro Cys Pro Pro Cys Pro Ala Pro Glu Ala Ala
    50                  55                  60

<210> SEQ ID NO 9
<211> LENGTH: 63
<212> TYPE: PRT
<213> ORGANISM: Artificial sequence
<220> FEATURE:
<223> OTHER INFORMATION: Fusion protein of GLP-1 variant-Linker-J
      region-Hinge

<400> SEQUENCE: 9
```

His Asp Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly Gly
            20                  25                  30

Gly Ser Gly Gly Gly Ser Gly Thr Leu Val Thr Asn Ser Ser Glu Ser
        35                  40                  45

Lys Tyr Gly Pro Pro Cys Pro Pro Cys Pro Ala Pro Glu Ala Ala
50                  55                  60

<210> SEQ ID NO 10
<211> LENGTH: 63
<212> TYPE: PRT
<213> ORGANISM: Artificial sequence
<220> FEATURE:
<223> OTHER INFORMATION: Fusion protein of GLP-1 variant-Linker-J
      region-Hinge

<400> SEQUENCE: 10

His Thr Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly Gly
            20                  25                  30

Gly Ser Gly Gly Gly Ser Gly Thr Leu Val Thr Asn Ser Ser Glu Ser
        35                  40                  45

Lys Tyr Gly Pro Pro Cys Pro Pro Cys Pro Ala Pro Glu Ala Ala
50                  55                  60

<210> SEQ ID NO 11
<211> LENGTH: 63
<212> TYPE: PRT
<213> ORGANISM: Artificial sequence
<220> FEATURE:
<223> OTHER INFORMATION: Fusion protein of GLP-1 variant-Linker-J
      region-Hinge

<400> SEQUENCE: 11

His Val Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly Gly
            20                  25                  30

Gly Ser Gly Gly Gly Ser Gly Thr Leu Val Thr Asn Ser Ser Glu Ser
        35                  40                  45

Lys Tyr Gly Pro Pro Cys Pro Pro Cys Pro Ala Pro Glu Ala Ala
50                  55                  60

<210> SEQ ID NO 12
<211> LENGTH: 52
<212> TYPE: PRT
<213> ORGANISM: Artificial sequence
<220> FEATURE:
<223> OTHER INFORMATION: Fusion protein of GLP-1 variant-Linker-J
      region-Hinge

<400> SEQUENCE: 12

His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Thr Gly
            20                  25                  30

Gly Gly Ser Glu Ser Lys Tyr Gly Pro Pro Cys Pro Pro Cys Pro Ala
        35                  40                  45

Pro Glu Ala Ala

```
<210> SEQ ID NO 13
<211> LENGTH: 43
<212> TYPE: PRT
<213> ORGANISM: Artificial sequence
<220> FEATURE:
<223> OTHER INFORMATION: Fusion protein of GLP-1 variant-Linker-J
      region-Hinge

<400> SEQUENCE: 13

His Ser Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Thr Gly
            20                  25                  30

Ser Cys Pro Pro Cys Pro Ala Pro Glu Ala Asn
        35                  40

<210> SEQ ID NO 14
<211> LENGTH: 72
<212> TYPE: PRT
<213> ORGANISM: Artificial sequence
<220> FEATURE:
<223> OTHER INFORMATION: Fusion protein of GLP-1 variant-Linker-J
      region-Hinge

<400> SEQUENCE: 14

His Gly Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Gly Pro Ser
            20                  25                  30

Ser Gly Ala Pro Pro Pro Ser Gly Gly Gly Ser Gly Gly Gly Ser Gly
        35                  40                  45

Thr Leu Val Thr Asn Ser Ser Glu Ser Lys Tyr Gly Pro Pro Cys Pro
    50                  55                  60

Pro Cys Pro Ala Pro Glu Ala Ala
65                  70

<210> SEQ ID NO 15
<211> LENGTH: 31
<212> TYPE: PRT
<213> ORGANISM: Homo sapiens

<400> SEQUENCE: 15

His Ala Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly
            20                  25                  30

<210> SEQ ID NO 16
<211> LENGTH: 4
<212> TYPE: PRT
<213> ORGANISM: Artificial Sequence
<220> FEATURE:
<223> OTHER INFORMATION: Peptide linker

<400> SEQUENCE: 16

Gly Gly Gly Ser
1

<210> SEQ ID NO 17
<211> LENGTH: 6
<212> TYPE: PRT
<213> ORGANISM: Artificial Sequence
```

```
<220> FEATURE:
<223> OTHER INFORMATION: Peptide linker

<400> SEQUENCE: 17

Gly Ser Gly Gly Gly Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Peptide linker

<400> SEQUENCE: 18

Gly Gly Ser Gly Gly Gly Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Peptide linker

<400> SEQUENCE: 19

Gly Gly Ser Gly Gly Gly Ser Gly Gly
1               5

<210> SEQ ID NO 20
<211> LENGTH: 10
<212> TYPE: PRT
<213> ORGANISM: Artificial Sequence
<220> FEATURE:
<223> OTHER INFORMATION: Peptide linker

<400> SEQUENCE: 20

Gly Gly Gly Ser Gly Gly Gly Ser Gly Gly
1               5                   10

<210> SEQ ID NO 21
<211> LENGTH: 8
<212> TYPE: PRT
<213> ORGANISM: Artificial Sequence
<220> FEATURE:
<223> OTHER INFORMATION: Synthetic peptide

<400> SEQUENCE: 21

Gly Thr Leu Val Thr Val Ser Ser
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic
      peptide

<400> SEQUENCE: 22

Gly Thr Leu Val Ala Val Ser Ser
1               5

<210> SEQ ID NO 23
<211> LENGTH: 8
<212> TYPE: PRT
<213> ORGANISM: Artificial Sequence
<220> FEATURE:
```

```
<223> OTHER INFORMATION: Synthetic
      peptide

<400> SEQUENCE: 23

Gly Thr Ala Val Thr Val Ser Ser
1               5

<210> SEQ ID NO 24
<211> LENGTH: 4
<212> TYPE: PRT
<213> ORGANISM: Artificial Sequence
<220> FEATURE:
<223> OTHER INFORMATION: Synthetic
      peptide

<400> SEQUENCE: 24

Thr Val Ser Ser
1

<210> SEQ ID NO 25
<211> LENGTH: 4
<212> TYPE: PRT
<213> ORGANISM: Artificial Sequence
<220> FEATURE:
<223> OTHER INFORMATION: Synthetic
      peptide

<400> SEQUENCE: 25

Ala Val Ser Ser
1

<210> SEQ ID NO 26
<211> LENGTH: 23
<212> TYPE: PRT
<213> ORGANISM: Homo sapiens

<400> SEQUENCE: 26

Glu Pro Lys Ser Cys Asp Lys Thr His Thr Cys Pro Pro Cys Pro Ala
1               5                   10                  15

Pro Glu Leu Leu Gly Gly Pro
            20

<210> SEQ ID NO 27
<211> LENGTH: 20
<212> TYPE: PRT
<213> ORGANISM: Homo sapiens

<400> SEQUENCE: 27

Glu Ser Lys Tyr Gly Pro Pro Cys Pro Ser Cys Pro Ala Pro Glu Phe
1               5                   10                  15

Leu Gly Gly Pro
            20

<210> SEQ ID NO 28
<211> LENGTH: 20
<212> TYPE: PRT
<213> ORGANISM: Homo sapiens

<400> SEQUENCE: 28

Glu Ser Lys Tyr Gly Pro Pro Cys Pro Pro Cys Pro Ala Pro Glu Ala
1               5                   10                  15

Ala Gly Gly Pro
            20

<210> SEQ ID NO 29
```

```
<211> LENGTH: 23
<212> TYPE: PRT
<213> ORGANISM: Homo sapiens

<400> SEQUENCE: 29

Glu Pro Lys Ser Ala Asp Lys Thr His Thr Cys Pro Pro Cys Pro Ala
1               5                   10                  15

Pro Glu Ala Ala Gly Gly Pro
            20

<210> SEQ ID NO 30
<211> LENGTH: 23
<212> TYPE: PRT
<213> ORGANISM: Homo sapiens

<400> SEQUENCE: 30

Glu Pro Lys Ser Ala Asp Lys Thr His Thr Cys Pro Pro Cys Pro Ala
1               5                   10                  15

Pro Glu Leu Ala Gly Gly Pro
            20

<210> SEQ ID NO 31
<211> LENGTH: 23
<212> TYPE: PRT
<213> ORGANISM: Homo sapiens

<400> SEQUENCE: 31

Glu Pro Lys Ser Ala Asp Lys Thr His Thr Cys Pro Pro Cys Pro Ala
1               5                   10                  15

Pro Glu Ala Leu Gly Gly Pro
            20

<210> SEQ ID NO 32
<211> LENGTH: 23
<212> TYPE: PRT
<213> ORGANISM: Homo sapiens

<400> SEQUENCE: 32

Glu Pro Lys Ser Ala Asp Lys Thr His Thr Cys Pro Pro Cys Pro Ala
1               5                   10                  15

Pro Glu Leu Glu Gly Gly Pro
            20

<210> SEQ ID NO 33
<211> LENGTH: 23
<212> TYPE: PRT
<213> ORGANISM: Homo sapiens

<400> SEQUENCE: 33

Glu Pro Lys Ser Ser Asp Lys Thr His Thr Cys Pro Pro Cys Pro Ala
1               5                   10                  15

Pro Glu Phe Leu Gly Gly Pro
            20

<210> SEQ ID NO 34
<211> LENGTH: 23
<212> TYPE: PRT
<213> ORGANISM: Homo sapiens

<400> SEQUENCE: 34

Glu Pro Lys Ser Ala Asp Lys Thr His Ala Cys Pro Pro Cys Pro Ala
1               5                   10                  15

Pro Glu Leu Leu Gly Gly Pro
```

```
                20

<210> SEQ ID NO 35
<211> LENGTH: 23
<212> TYPE: PRT
<213> ORGANISM: Homo sapiens

<400> SEQUENCE: 35

Glu Pro Lys Ser Ala Asp Lys Ala His Thr Cys Pro Pro Cys Pro Ala
1               5                   10                  15

Pro Glu Leu Leu Gly Gly Pro
            20

<210> SEQ ID NO 36
<211> LENGTH: 23
<212> TYPE: PRT
<213> ORGANISM: Homo sapiens

<400> SEQUENCE: 36

Glu Pro Lys Ser Ala Asp Lys Thr His Thr Cys Pro Pro Cys Pro Ala
1               5                   10                  15

Pro Glu Leu Leu Gly Gly Pro
            20

<210> SEQ ID NO 37
<211> LENGTH: 19
<212> TYPE: PRT
<213> ORGANISM: Homo sapiens

<400> SEQUENCE: 37

Ala Asp Lys Thr His Thr Cys Pro Pro Cys Pro Ala Pro Glu Leu Leu
1               5                   10                  15

Gly Gly Pro

<210> SEQ ID NO 38
<211> LENGTH: 16
<212> TYPE: PRT
<213> ORGANISM: Homo sapiens

<400> SEQUENCE: 38

Thr His Thr Cys Pro Pro Cys Pro Ala Pro Glu Leu Leu Gly Gly Pro
1               5                   10                  15

<210> SEQ ID NO 39
<211> LENGTH: 20
<212> TYPE: PRT
<213> ORGANISM: Homo sapiens

<400> SEQUENCE: 39

Glu Ser Lys Tyr Gly Pro Pro Cys Pro Ser Cys Pro Ala Pro Glu Ala
1               5                   10                  15

Ala Gly Gly Pro
            20

<210> SEQ ID NO 40
<211> LENGTH: 20
<212> TYPE: PRT
<213> ORGANISM: Homo sapiens

<400> SEQUENCE: 40

Glu Ser Lys Tyr Gly Pro Pro Cys Pro Pro Cys Pro Ala Pro Glu Leu
1               5                   10                  15

Leu Gly Gly Pro
```

-continued

```
                20

<210> SEQ ID NO 41
<211> LENGTH: 13
<212> TYPE: PRT
<213> ORGANISM: Homo sapiens

<400> SEQUENCE: 41

Cys Pro Pro Cys Pro Ala Pro Glu Leu Leu Gly Gly Pro
1               5                   10

<210> SEQ ID NO 42
<211> LENGTH: 13
<212> TYPE: PRT
<213> ORGANISM: Homo sapiens

<400> SEQUENCE: 42

Cys Pro Pro Cys Pro Ala Pro Glu Ala Ala Gly Gly Pro
1               5                   10

<210> SEQ ID NO 43
<211> LENGTH: 102
<212> TYPE: PRT
<213> ORGANISM: Homo sapiens

<400> SEQUENCE: 43

Ser Val Phe Leu Phe Pro Pro Lys Pro Lys Asp Thr Leu Met Ile Ser
1               5                   10                  15

Arg Thr Pro Glu Val Thr Cys Val Val Val Asp Val Ser His Glu Asp
            20                  25                  30

Pro Glu Val Lys Phe Asn Trp Tyr Val Asp Gly Val Glu Val His Asn
        35                  40                  45

Ala Lys Thr Lys Pro Arg Glu Glu Gln Tyr Asn Ser Thr Tyr Arg Asn
    50                  55                  60

Val Ser Val Leu Thr Val Leu His Gln Asp Trp Leu Asn Gly Lys Glu
65                  70                  75                  80

Tyr Lys Cys Lys Val Ser Asn Lys Ala Leu Pro Ala Pro Ile Glu Lys
                85                  90                  95

Thr Ile Ser Lys Ala Lys
            100

<210> SEQ ID NO 44
<211> LENGTH: 107
<212> TYPE: PRT
<213> ORGANISM: Homo sapiens

<400> SEQUENCE: 44

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Asn Phe Ser Cys Ser Val Met His Glu Ala Leu His Asn His Tyr
                85                  90                  95

Thr Gln Lys Ser Leu Ser Leu Ser Pro Gly Lys
```

<210> SEQ ID NO 45
<211> LENGTH: 102
<212> TYPE: PRT
<213> ORGANISM: Homo sapiens

<400> SEQUENCE: 45

Ser Val Phe Leu Phe Pro Pro Lys Pro Lys Asp Thr Leu Met Ile Ser
1               5                   10                  15

Arg Thr Pro Glu Val Thr Cys Val Val Val Asp Val Ser Gln Glu Asp
            20                  25                  30

Pro Glu Val Gln Phe Asn Trp Tyr Val Asp Gly Val Glu Val His Asn
        35                  40                  45

Ala Lys Thr Lys Pro Arg Glu Glu Gln Phe Asn Ser Thr Tyr Arg Asn
    50                  55                  60

Val Ser Val Leu Thr Val Leu His Gln Asp Trp Leu Asn Gly Lys Glu
65                  70                  75                  80

Tyr Lys Cys Lys Val Ser Asn Lys Gly Leu Pro Ser Ser Ile Glu Lys
                85                  90                  95

Thr Ile Ser Lys Ala Lys
            100

<210> SEQ ID NO 46
<211> LENGTH: 107
<212> TYPE: PRT
<213> ORGANISM: Homo sapiense

<400> SEQUENCE: 46

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Asn Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 47
<211> LENGTH: 125
<212> TYPE: PRT
<213> ORGANISM: Homo sapiens
<220> FEATURE:
<221> NAME/KEY: MOD_RES
<222> LOCATION: (32)
<223> OTHER INFORMATION: Variable amino acid
<220> FEATURE:
<221> NAME/KEY: MOD_RES
<222> LOCATION: (47)
<223> OTHER INFORMATION: Variable amino acid
<220> FEATURE:
<221> NAME/KEY: MOD_RES
<222> LOCATION: (80)
<223> OTHER INFORMATION: Variable amino acid

<400> SEQUENCE: 47

```
Gln Val Gln Leu Leu Val Gln Ser Gly Ala Glu Val Lys Lys Pro Gly
1               5                   10                  15

Ala Ser Val Lys Val Ser Cys Lys Ala Ser Gly Tyr Thr Phe Thr Xaa
            20                  25                  30

Trp Val Arg Gln Ala Pro Gly Gln Gly Leu Glu Trp Met Gly Xaa Arg
            35                  40                  45

Val Thr Met Thr Arg Asp Thr Ser Ser Thr Ala Tyr Met Glu Leu
50                  55                  60

Ser Ser Leu Arg Ser Glu Asp Thr Ala Val Tyr Tyr Cys Ala Arg Xaa
65              70                  75                  80

Trp Gly Gln Gly Thr Leu Val Thr Asn Ser Ser Gly Ser Thr Lys Gly
            85                  90                  95

Pro Ser Val Phe Pro Leu Ala Pro Ser Ser Lys Ser Thr Ser Gly Gly
            100                 105                 110

Thr Ala Ala Leu Gly Cys Leu Val Lys Asp Tyr Phe Pro
            115                 120                 125

<210> SEQ ID NO 48
<211> LENGTH: 124
<212> TYPE: PRT
<213> ORGANISM: Homo sapiens
<220> FEATURE:
<221> NAME/KEY: MOD_RES
<222> LOCATION: (31)
<223> OTHER INFORMATION: Variable amino acid
<220> FEATURE:
<221> NAME/KEY: MOD_RES
<222> LOCATION: (46)
<223> OTHER INFORMATION: Variable amino acid
<220> FEATURE:
<221> NAME/KEY: MOD_RES
<222> LOCATION: (79)
<223> OTHER INFORMATION: Variable amino acid

<400> SEQUENCE: 48

Gln Ile Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Xaa Trp
            20                  25                  30

Ile Arg Gln Pro Pro Gly Lys Ala Leu Glu Trp Leu Ala Xaa Arg Leu
            35                  40                  45

Thr Ile Thr Lys Asp Thr Ser Lys Asn Gln Val Val Leu Thr Met Thr
50                  55                  60

Asn Met Asp Pro Val Asp Thr Ala Thr Tyr Tyr Cys Ala Arg Xaa Trp
65                  70                  75                  80

Gly Gln Gly Thr Leu Val Thr Asn Ser Ser Ala Ser Pro Thr Ser Pro
            85                  90                  95

Lys Val Phe Pro Leu Ser Leu Ser Ser Lys Ser Thr Ser Gly Gly Thr
            100                 105                 110

Ala Ala Leu Gly Cys Leu Val Lys Asp Tyr Phe Pro
            115                 120

<210> SEQ ID NO 49
<211> LENGTH: 100
<212> TYPE: PRT
<213> ORGANISM: Homo sapiens
<220> FEATURE:
<221> NAME/KEY: MOD_RES
<222> LOCATION: (32)
<223> OTHER INFORMATION: Variable amino acid
<220> FEATURE:
<221> NAME/KEY: MOD_RES
<222> LOCATION: (47)
```

```
<223> OTHER INFORMATION: Variable amino acid
<220> FEATURE:
<221> NAME/KEY: MOD_RES
<222> LOCATION: (80)
<223> OTHER INFORMATION: Variable amino acid

<400> SEQUENCE: 49

Glu Val Val Gln Leu Val Glu Ser Gly Gly Leu Val Gln Pro Gly
1               5                   10                  15

Gly Ser Leu Arg Leu Ser Cys Ala Ala Ser Gly Phe Thr Phe Ser Xaa
                20                  25                  30

Trp Val Arg Gln Ala Pro Gly Lys Gly Leu Glu Trp Val Ser Xaa Arg
                35                  40                  45

Phe Thr Ile Ser Arg Asp Asn Ser Lys Asn Thr Leu Tyr Leu Gln Met
            50                  55                  60

Asn Ser Leu Arg Ala Glu Asp Thr Ala Val Tyr Tyr Cys Ala Arg Xaa
65                  70                  75                  80

Trp Gly Gln Gly Thr Leu Val Thr Asn Ser Ser Gly Thr Lys Ala
                85                  90                  95

Pro Ser Val Phe
            100

<210> SEQ ID NO 50
<211> LENGTH: 102
<212> TYPE: PRT
<213> ORGANISM: Homo sapiens
<220> FEATURE:
<221> NAME/KEY: MOD_RES
<222> LOCATION: (31)
<223> OTHER INFORMATION: Variable amino acid
<220> FEATURE:
<221> NAME/KEY: MOD_RES
<222> LOCATION: (46)
<223> OTHER INFORMATION: Variable amino acid
<220> FEATURE:
<221> NAME/KEY: MOD_RES
<222> LOCATION: (79)
<223> OTHER INFORMATION: Variable amino acid

<400> SEQUENCE: 50

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Xaa Trp
                20                  25                  30

Val Arg Gln Ala Pro Gly Lys Gly Leu Glu Trp Val Gly Xaa Arg Phe
                35                  40                  45

Thr Ile Ser Arg Asp Asp Ser Lys Asn Thr Leu Tyr Leu Gln Met Asn
        50                  55                  60

Ser Leu Lys Thr Glu Asp Thr Ala Val Tyr Tyr Cys Thr Thr Xaa Trp
65                  70                  75                  80

Gly Gln Gly Thr Leu Val Thr Asn Ser Ser Ala Ser Thr Lys Gly Pro
                85                  90                  95

Ser Val Phe Pro Leu Ala
            100

<210> SEQ ID NO 51
<211> LENGTH: 101
<212> TYPE: PRT
<213> ORGANISM: Homo sapiens
<220> FEATURE:
<221> NAME/KEY: MOD_RES
<222> LOCATION: (31)
<223> OTHER INFORMATION: Variable amino acid
<220> FEATURE:
```

```
<221> NAME/KEY: MOD_RES
<222> LOCATION: (46)
<223> OTHER INFORMATION: Variable amino acid
<220> FEATURE:
<221> NAME/KEY: MOD_RES
<222> LOCATION: (80)
<223> OTHER INFORMATION: Variable amino acid

<400> SEQUENCE: 51
```

| Glu | Val | Gln | Leu | Val | Glu | Ser | Gly | Gly | Gly | Leu | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Thr | Ala | Ser | Gly | Phe | Thr | Phe | Gly | Xaa | Trp |
|---|---|---|---|---|---|---|---|---|---|---|---|---|---|---|---|
| | | | 20 | | | | | 25 | | | | | 30 | | |

| Val | Arg | Gln | Ala | Pro | Gly | Lys | Gly | Leu | Glu | Trp | Val | Gly | Xaa | Arg | Phe |
|---|---|---|---|---|---|---|---|---|---|---|---|---|---|---|---|
| | | 35 | | | | | 40 | | | | | 45 | | | |

| Thr | Ile | Ser | Arg | Asp | Asp | Ser | Lys | Ser | Ile | Ala | Tyr | Leu | Gln | Met | Asn |
|---|---|---|---|---|---|---|---|---|---|---|---|---|---|---|---|
| | 50 | | | | | 55 | | | | | 60 | | | | |

| Ser | Leu | Lys | Thr | Glu | Asp | Thr | Ala | Val | Tyr | Tyr | Cys | Thr | Arg | Asn | Xaa |
|---|---|---|---|---|---|---|---|---|---|---|---|---|---|---|---|
| 65 | | | | | 70 | | | | | 75 | | | | | 80 |

| Trp | Gly | Gln | Gly | Thr | Leu | Val | Thr | Asn | Ser | Ser | Gly | Ser | Thr | Lys | Gly |
|---|---|---|---|---|---|---|---|---|---|---|---|---|---|---|---|
| | | | | 85 | | | | | 90 | | | | | 95 | |

| Pro | Ser | Val | Leu | Pro |
|---|---|---|---|---|
| | | | 100 | |

```
<210> SEQ ID NO 52
<211> LENGTH: 108
<212> TYPE: PRT
<213> ORGANISM: Homo sapiens
<220> FEATURE:
<221> NAME/KEY: MOD_RES
<222> LOCATION: (34)
<223> OTHER INFORMATION: Variable amino acid
<220> FEATURE:
<221> NAME/KEY: MOD_RES
<222> LOCATION: (49)
<223> OTHER INFORMATION: Variable amino acid
<220> FEATURE:
<221> NAME/KEY: MOD_RES
<222> LOCATION: (82)
<223> OTHER INFORMATION: Variable amino acid

<400> SEQUENCE: 52
```

| Gln | Val | Gln | Leu | Gln | Glu | Ser | Gly | Pro | Gly | Leu | Val | Lys | Pro | Ser | Glu |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Thr | Val | Ser | Gly | Gly | Ser | Ile | Ser | Ser | Ser |
|---|---|---|---|---|---|---|---|---|---|---|---|---|---|---|---|
| | | | 20 | | | | | 25 | | | | | 30 | | |

| Ser | Xaa | Trp | Ile | Arg | Gln | Pro | Pro | Gly | Lys | Gly | Leu | Glu | Trp | Ile | Gly |
|---|---|---|---|---|---|---|---|---|---|---|---|---|---|---|---|
| | | 35 | | | | | 40 | | | | | 45 | | | |

| Xaa | Arg | Val | Thr | Ile | Ser | Val | Asp | Thr | Ser | Lys | Asn | Gln | Phe | Ser | Leu |
|---|---|---|---|---|---|---|---|---|---|---|---|---|---|---|---|
| | 50 | | | | | 55 | | | | | 60 | | | | |

| Lys | Leu | Ser | Ser | Val | Thr | Ala | Ala | Asp | Thr | Ala | Val | Tyr | Tyr | Cys | Ala |
|---|---|---|---|---|---|---|---|---|---|---|---|---|---|---|---|
| 65 | | | | | 70 | | | | | 75 | | | | | 80 |

| Arg | Xaa | Trp | Gly | Gln | Gly | Thr | Leu | Val | Thr | Asn | Ser | Ser | Ala | Pro | Thr |
|---|---|---|---|---|---|---|---|---|---|---|---|---|---|---|---|
| | | | | 85 | | | | | 90 | | | | | 95 | |

| Lys | Ala | Pro | Asp | Val | Phe | Pro | Ile | Ile | Ser | Gly | Cys |
|---|---|---|---|---|---|---|---|---|---|---|---|
| | | | 100 | | | | | 105 | | | |

```
<210> SEQ ID NO 53
<211> LENGTH: 132
<212> TYPE: PRT
<213> ORGANISM: Homo sapiens
<220> FEATURE:
<221> NAME/KEY: MOD_RES
<222> LOCATION: (32)
```

-continued

<223> OTHER INFORMATION: Variable amino acid
<220> FEATURE:
<221> NAME/KEY: MOD_RES
<222> LOCATION: (47)
<223> OTHER INFORMATION: Variable amino acid
<220> FEATURE:
<221> NAME/KEY: MOD_RES
<222> LOCATION: (80)
<223> OTHER INFORMATION: Variable amino acid

<400> SEQUENCE: 53

```
Glu Glu Val Gln Leu Val Gln Ser Gly Ala Glu Val Lys Lys Pro Gly
1               5                   10                  15

Glu Ser Leu Lys Ile Ser Cys Lys Gly Ser Gly Tyr Ser Phe Thr Xaa
            20                  25                  30

Trp Val Arg Gln Met Pro Gly Lys Gly Leu Glu Trp Met Gly Xaa Gln
        35                  40                  45

Val Thr Ile Ser Ala Asp Lys Ser Ile Ser Thr Ala Tyr Leu Gln Trp
    50                  55                  60

Ser Ser Leu Lys Ala Ser Asp Thr Ala Met Tyr Tyr Cys Ala Arg Xaa
65                  70                  75                  80

Trp Gly Gln Gly Thr Leu Val Thr Asn Ser Ser Ala Ser Thr Lys Ala
                85                  90                  95

Pro Ser Val Phe Pro Leu Val Ser Cys Glu Asn Ser Pro Ser Asp Thr
            100                 105                 110

Ser Ser Val Ala Val Gly Cys Leu Ala Gln Asp Phe Leu Pro Asp Ser
        115                 120                 125

Ile Thr Phe Ser
    130
```

<210> SEQ ID NO 54
<211> LENGTH: 125
<212> TYPE: PRT
<213> ORGANISM: Homo sapiens
<220> FEATURE:
<221> NAME/KEY: MOD_RES
<222> LOCATION: (31)
<223> OTHER INFORMATION: Variable amino acid
<220> FEATURE:
<221> NAME/KEY: MOD_RES
<222> LOCATION: (46)
<223> OTHER INFORMATION: Variable amino acid
<220> FEATURE:
<221> NAME/KEY: MOD_RES
<222> LOCATION: (79)
<223> OTHER INFORMATION: Variable amino acid

<400> SEQUENCE: 54

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Xaa Trp
            20                  25                  30

Ile Arg Gln Ser Pro Ser Arg Gly Leu Glu Trp Leu Gly Xaa Arg Ile
        35                  40                  45

Thr Ile Asn Pro Asp Thr Ser Lys Asn Gln Phe Ser Leu Gln Leu Asn
    50                  55                  60

Ser Val Thr Pro Glu Asp Thr Ala Val Tyr Tyr Cys Ala Arg Xaa Trp
65                  70                  75                  80

Gly Gln Gly Thr Leu Val Thr Asn Ser Ser Gly Ser Ala Ser Ala Pro
                85                  90                  95

Thr Leu Phe Pro Leu Val Ser Cys Glu Asn Ser Pro Ser Asp Thr Ser
            100                 105                 110
```

```
Ser Val Ala Val Gly Cys Leu Ala Gln Asp Phe Leu Pro
        115                 120                 125
```

<210> SEQ ID NO 55
<211> LENGTH: 91
<212> TYPE: PRT
<213> ORGANISM: Homo sapiens
<220> FEATURE:
<221> NAME/KEY: MOD_RES
<222> LOCATION: (31)
<223> OTHER INFORMATION: Variable amino acid
<220> FEATURE:
<221> NAME/KEY: MOD_RES
<222> LOCATION: (46)
<223> OTHER INFORMATION: Variable amino acid
<220> FEATURE:
<221> NAME/KEY: MOD_RES
<222> LOCATION: (79)
<223> OTHER INFORMATION: Variable amino acid

<400> SEQUENCE: 55

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Xaa Trp
            20                  25                  30

Val Arg Gln Ala Pro Gly Gln Gly Leu Glu Trp Met Gly Xaa Arg Phe
        35                  40                  45

Val Phe Ser Leu Asp Thr Ser Val Ser Thr Ala Tyr Leu Gln Ile Ser
    50                  55                  60

Ser Leu Lys Ala Glu Asp Thr Ala Val Tyr Tyr Cys Ala Arg Xaa Trp
65                  70                  75                  80

Gly Gln Gly Thr Leu Val Thr Asn Ser Ser Ser
                85                  90
```

<210> SEQ ID NO 56
<211> LENGTH: 354
<212> TYPE: PRT
<213> ORGANISM: Homo sapiens

<400> SEQUENCE: 56

```
Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Asn Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
```

Arg Asp Leu Cys Gly Cys Tyr Ser Asn Ser Val Leu Pro Gly Cys
              180                 185                 190

Ala Glu Pro Trp Asn His Gly Lys Thr Phe Thr Cys Thr Ala Ala Tyr
          195                 200                 205

Pro Glu Ser Lys Thr Pro Leu Thr Ala Thr Leu Ser Lys Ser Gly Asn
      210                 215                 220

Thr Phe Arg Pro Glu Val His Leu Leu Pro Pro Ser Glx Glu Glu
225                 230                 235                 240

Leu Ala Leu Asn Glu Leu Val Thr Leu Thr Cys Leu Ala Arg Gly Phe
                  245                 250                 255

Ser Pro Lys Asp Val Leu Val Arg Trp Leu Gln Gly Ser Gln Glu Leu
              260                 265                 270

Pro Arg Glu Lys Tyr Leu Thr Trp Ala Ser Arg Gln Glu Pro Ser Gln
          275                 280                 285

Gly Thr Thr Thr Phe Ala Val Thr Ser Ile Leu Arg Val Ala Ala Glu
      290                 295                 300

Asp Trp Lys Lys Gly Asp Thr Phe Ser Cys Met Val Gly His Glu Ala
305                 310                 315                 320

Leu Pro Leu Ala Phe Thr Gln Lys Thr Ile Asp Arg Leu Ala Gly Lys
                  325                 330                 335

Pro Thr His Val Asn Val Ser Val Val Met Ala Glu Val Asp Gly Thr
              340                 345                 350

Cys Tyr

<210> SEQ ID NO 57
<211> LENGTH: 340
<212> TYPE: PRT
<213> ORGANISM: Homo sapiens

<400> SEQUENCE: 57

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

```
Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Leu Ala
305                 310                 315                 320

Gly Lys Pro Thr His Val Asn Val Ser Val Val Met Ala Glu Val Asp
                325                 330                 335

Gly Thr Cys Tyr
        340

<210> SEQ ID NO 58
<211> LENGTH: 384
<212> TYPE: PRT
<213> ORGANISM: Homo sapiens

<400> SEQUENCE: 58

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205

Lys Val Pro Thr Gly Gly Val Glu Glu Gly Leu Leu Glu Arg His Ser
    210                 215                 220
```

```
Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
            245                 250                 255

Pro Pro Gln Arg Leu Met Ala Leu Arg Glu Pro Ala Ala Gln Ala Pro
                260                 265                 270

Val Lys Leu Ser Leu Asn Leu Leu Ala Ser Ser Asp Pro Pro Glu Ala
            275                 280                 285

Ala Ser Trp Leu Leu Cys Glu Val Ser Gly Phe Ser Pro Pro Asn Ile
290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Arg Ser Thr Thr Phe Trp Ala
                325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met Lys
370                 375                 380

<210> SEQ ID NO 59
<211> LENGTH: 497
<212> TYPE: PRT
<213> ORGANISM: Homo sapiens

<400> SEQUENCE: 59

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly Gly His Phe Pro
        115                 120                 125

Pro Thr Ile Gln Leu Leu Cys Leu Val Ser Gly Tyr Thr Pro Gly Thr
130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
                165                 170                 175

Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys
        195                 200                 205

Cys Ala Asp Ser Asn Pro Arg Gly Val Ser Ala Tyr Leu Ser Arg Pro
    210                 215                 220
```

```
Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
            245                 250                 255

Arg Ala Ser Gly Lys Pro Val Asn His Ser Thr Arg Lys Glu Glu Lys
                260                 265                 270

Gln Arg Asn Gly Thr Leu Thr Val Thr Ser Thr Leu Pro Val Gly Thr
            275                 280                 285

Arg Asp Trp Ile Glu Gly Glu Thr Tyr Gln Cys Arg Val Thr His Pro
290                 295                 300

His Leu Pro Arg Ala Leu Met Arg Ser Thr Thr Lys Thr Ser Gly Pro
305                 310                 315                 320

Val Gly Pro Arg Ala Ala Pro Glu Val Tyr Ala Phe Ala Thr Pro Glu
                325                 330                 335

Trp Pro Gly Ser Arg Asp Lys Arg Thr Leu Ala Cys Leu Ile Gln Asn
                340                 345                 350

Phe Met Pro Glu Asp Ile Ser Val Gln Trp Leu His Asn Glu Val Gln
            355                 360                 365

Leu Pro Asp Ala Arg His Ser Thr Thr Gln Pro Arg Lys Thr Lys Gly
370                 375                 380

Ser Gly Phe Phe Val Phe Ser Arg Leu Glu Val Thr Arg Ala Glu Trp
385                 390                 395                 400

Glu Gln Lys Asp Glu Phe Ile Cys Arg Ala Val His Glu Ala Ala Ser
                405                 410                 415

Pro Ser Gln Thr Val Gln Arg Ala Val Ser Val Asn Pro Gly Lys Asp
                420                 425                 430

Val Cys Val Glu Glu Ala Glu Gly Glu Ala Pro Trp Thr Trp Thr Gly
            435                 440                 445

Leu Cys Ile Phe Ala Ala Leu Phe Leu Leu Ser Val Ser Tyr Ser Ala
450                 455                 460

Ala Leu Thr Leu Leu Met Val Gln Arg Phe Leu Ser Ala Thr Arg Gln
465                 470                 475                 480

Gly Arg Pro Gln Thr Ser Leu Asp Tyr Thr Asn Val Leu Gln Pro His
                485                 490                 495

Ala

<210> SEQ ID NO 60
<211> LENGTH: 339
<212> TYPE: PRT
<213> ORGANISM: Homo sapiens

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asx Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys Thr His Thr Cys Pro
                325                 330                 335

Pro Cys Pro

<210> SEQ ID NO 61
<211> LENGTH: 326
<212> TYPE: PRT
<213> ORGANISM: Homo sapiens

<400> SEQUENCE: 61

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
```

```
                130                 135                 140
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Asn Val Ser Val Leu Thr Val Val His Gln Asp Trp
                180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 62
<211> LENGTH: 377
<212> TYPE: PRT
<213> ORGANISM: Homo sapiens

<400> SEQUENCE: 62

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
```

-continued

```
                180                 185                 190
Val Val Asp Val Ser His Glu Asp Pro Glu Val Gln Phe Lys Trp Tyr
                195                 200                 205
Val Asp Gly Val Glu Val His Asn Ala Lys Thr Lys Pro Arg Glu Glu
            210                 215                 220
Gln Tyr Asn Ser Thr Phe Arg Asn Val Ser Val Leu Thr Val Leu His
225                 230                 235                 240
Gln Asp Trp Leu Asn Gly Lys Glu Tyr Lys Cys Lys Val Ser Asn Lys
                245                 250                 255
Ala Leu Pro Ala Pro Ile Glu Lys Thr Ile Ser Lys Thr Lys Gly Gln
            260                 265                 270
Pro Arg Glu Pro Gln Val Tyr Thr Leu Pro Pro Ser Arg Glu Glu Met
        275                 280                 285
Thr Lys Asn Gln Val Ser Leu Thr Cys Leu Val Lys Gly Phe Tyr Pro
        290                 295                 300
Ser Asp Ile Ala Val Glu Trp Glu Ser Ser Gly Gln Pro Glu Asn Asn
305                 310                 315                 320
Tyr Asn Thr Thr Pro Pro Met Leu Asp Ser Asp Gly Ser Phe Phe Leu
                325                 330                 335
Tyr Ser Lys Leu Thr Val Asp Lys Ser Arg Trp Gln Gln Gly Asn Ile
            340                 345                 350
Phe Ser Cys Ser Val Met His Glu Ala Leu His Asn Arg Phe Thr Gln
        355                 360                 365
Lys Ser Leu Ser Leu Ser Pro Gly Lys
        370                 375

<210> SEQ ID NO 63
<211> LENGTH: 327
<212> TYPE: PRT
<213> ORGANISM: Homo sapiens

<400> SEQUENCE: 63

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
        130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Asn Val Ser Val Leu Thr Val Leu His Gln Asp
```

```
                    180                 185                 190
Trp Leu Asn Gly Lys Glu Tyr Lys Cys Lys Val Ser Asn Lys Gly Leu
                195                 200                 205
Pro Ser Ser Ile Glu Lys Thr Ile Ser Lys Ala Lys Gly Gln Pro Arg
            210                 215                 220
Glu Pro Gln Val Tyr Thr Leu Pro Pro Ser Gln Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 64
<211> LENGTH: 476
<212> TYPE: PRT
<213> ORGANISM: Homo sapiens

<400> SEQUENCE: 64

Gly Ser Ala Ser Ala Pro Thr Leu Phe Pro Leu Val Ser Cys Glu Asn
1               5                   10                  15
Ser Pro Ser Asp Thr Ser Ser Val Ala Val Gly Cys Leu Ala Gln Asp
                20                  25                  30
Phe Leu Pro Asp Ser Ile Thr Phe Ser Trp Lys Tyr Lys Asn Asn Ser
            35                  40                  45
Asp Ile Ser Ser Thr Arg Gly Phe Pro Ser Val Leu Arg Gly Gly Lys
        50                  55                  60
Tyr Ala Ala Thr Ser Gln Val Leu Leu Pro Ser Lys Asp Val Met Gln
65                  70                  75                  80
Gly Thr Asp Glu His Val Val Cys Lys Val Gln His Pro Asn Gly Asn
                85                  90                  95
Lys Glu Lys Asn Val Pro Leu Pro Val Ile Ala Glu Leu Pro Pro Lys
            100                 105                 110
Val Ser Val Phe Val Pro Pro Arg Asp Gly Phe Phe Gly Asn Pro Arg
        115                 120                 125
Ser Lys Ser Lys Leu Ile Cys Gln Ala Thr Gly Phe Ser Pro Arg Gln
    130                 135                 140
Ile Gln Val Ser Trp Leu Arg Glu Gly Lys Gln Asn Gly Ser Gly Val
145                 150                 155                 160
Thr Thr Asp Gln Val Gln Ala Glu Ala Lys Glu Ser Gly Pro Thr Thr
                165                 170                 175
Tyr Lys Val Thr Ser Thr Leu Thr Ile Lys Glu Ser Asp Trp Leu Ser
            180                 185                 190
Gln Ser Met Phe Thr Cys Arg Val Asp His Arg Gly Leu Thr Phe Gln
        195                 200                 205
Gln Asn Ala Ser Ser Met Cys Val Pro Asp Gln Asp Thr Ala Ile Arg
    210                 215                 220
Val Phe Ala Ile Pro Pro Ser Phe Ala Ser Ile Phe Leu Thr Lys Ser
```

```
                    225                 230                 235                 240

Thr Lys Leu Thr Cys Leu Val Thr Asp Leu Thr Thr Tyr Asp Ser Val
                245                 250                 255

Thr Ile Ser Trp Thr Arg Gln Asn Gly Glu Ala Val Lys Thr His Thr
                260                 265                 270

Asn Ile Ser Glu Ser His Pro Asn Ala Thr Phe Ser Ala Val Gly Glu
                275                 280                 285

Ala Ser Ile Cys Glu Asp Asp Trp Asn Ser Gly Glu Arg Phe Thr Cys
                290                 295                 300

Thr Val Thr His Thr Asp Leu Pro Ser Pro Leu Lys Gln Thr Ile Ser
305                 310                 315                 320

Arg Pro Lys Gly Val Ala Leu His Arg Pro Asp Val Tyr Leu Leu Pro
                325                 330                 335

Pro Ala Arg Glu Gln Leu Asn Leu Arg Glu Ser Ala Thr Ile Thr Cys
                340                 345                 350

Leu Val Thr Gly Phe Ser Pro Ala Asp Val Phe Val Gln Trp Gln Met
                355                 360                 365

Gln Arg Gly Gln Pro Leu Ser Pro Glu Lys Tyr Val Thr Ser Ala Pro
                370                 375                 380

Met Pro Glu Pro Gln Ala Pro Gly Arg Tyr Phe Ala His Ser Ile Leu
385                 390                 395                 400

Thr Val Ser Glu Glu Glu Trp Asn Thr Gly Glu Thr Tyr Thr Cys Val
                405                 410                 415

Val Ala His Glu Ala Leu Pro Asn Arg Val Thr Glu Arg Thr Val Asp
                420                 425                 430

Lys Ser Thr Gly Lys Pro Thr Ser Ala Asp Glu Glu Gly Phe Glu Asn
                435                 440                 445

Leu Trp Ala Thr Ala Ser Thr Phe Ile Val Leu Tyr Asn Val Ser Leu
                450                 455                 460

Val Met Ser Asp Thr Ala Gly Thr Cys Tyr Val Lys
465                 470                 475
```

PHARMACEUTICAL COMPOSITION COMPRISING A HUMAN GLP-1 MIMETIBODY

CROSS REFERENCE TO RELATED APPLICATIONS

This application claims priority of the benefits of the filing of U.S. Provisional Application Ser. No. 60/831,704, filed Jul. 18, 2006. The complete disclosures of the aforementioned related U.S. patent application is hereby incorporated herein by reference for all purposes.

BACKGROUND OF THE INVENTION

1. Field of the Invention

The present invention relates to improved mammalian GLP-1 mimetibodies, specified portions and variants specific for biologically active proteins, fragment or ligands, GLP-1 mimetibody encoding and complementary nucleic acids, host cells, and methods of making and using thereof, including therapeutic formulations, administration and devices.

2. Related Art

Recombinant proteins are an emerging class of therapeutic agents. Such recombinant therapeutics have engendered advances in protein formulation and chemical modification. Such modifications can potentially enhance the therapeutic utility of therapeutic proteins, such as by increasing half lives (e.g., by blocking their exposure to proteolytic enzymes), enhancing biological activity, or reducing unwanted side effects. One such modification is the use of immunoglobulin fragments fused to receptor proteins, such as enteracept. Therapeutic proteins have also been constructed using the Fc domain to attempt to provide a longer half-life or to incorporate functions such as Fc receptor binding, protein A binding, and complement fixation.

Diabetes is a growing epidemic that is estimated to affect over 300 million people by the year 2025 pending an effective pharmaceutical cure. Type 2 diabetes accounts for 90-95% of all cases. Complications resulting from sustained elevated plasma glucose levels include cardiovascular disease, nephropathy, neuropathy, and retinopathy. In addition, the β-cells of the pancreas die and therefore cease to secrete insulin during the later stages of type 2 diabetes. Current treatments for diabetes are associated with a variety of deleterious side effects including hypoglycemia and weight gain. In addition, current treatments for type 2 diabetes do not cure the disease but simply prolong the time until patients require insulin therapy.

Glucagon like peptide-1 (GLP-1) is a 37-amino acid peptide secreted from the L-cells of the intestine following an oral glucose challenge. A subsequent endogenous cleavage between the 6th and 7th position produces the biologically active GLP-1 (7-37) peptide. The GLP-1 (7-37) peptide sequence can be divided into 2 structural domains. The amino terminal domain of the peptide is involved in signaling while the remainder of the peptide appears to bind to the extracellular loops of the GLP-1 receptor in a helical conformation. In response to glucose, the active GLP-1 binds to the GLP-1 receptor on the pancreas and causes an increase in insulin secretion (insulinotropic action). In addition, it has been shown that GLP-1 reduces gastric emptying which decreases the bolus of glucose that is released into the circulation and may reduce food intake. These actions in combination lower blood glucose levels. GLP-1 has also been shown to inhibit apoptosis and increase proliferation of the β-cells in the pancreas. Thus, GLP-1 is an attractive therapeutic to lower blood glucose and preserve the β-cells of the pancreas of diabetic patients. In addition, GLP-1 activity is controlled by blood glucose levels. When blood glucose levels drop to a certain threshold level, GLP-1 is not active. Therefore, there is no risk of hypoglycemia associated with treatment involving GLP-1.

The viability of GLP-1 therapy has been demonstrated in the clinic. A six-week GLP-1 infusion lowered fasting and 8-hour mean plasma glucose levels effectively in type 2 diabetic patients. GLP-1 therapy also resulted in an improvement in β-cell function. Exenatide is a GLP-1 analogue currently in clinical trials. Exenatide was first identified in the saliva of the gila monster lizard, and is 53% identical to GLP-1. Exenatide can bind the GLP-1 receptor and initiate the signal transduction cascade responsible for the numerous activities that have been attributed to GLP-1 (7-37). To date, it has been shown to reduce HbA1c levels and serum fructosamine levels in patients with type 2 diabetes. In addition, it delayed gastric emptying and inhibited food intake in healthy volunteers.

However, GLP-1 is rapidly inactivated in vivo by the protease dipeptidyl-peptidase IV (DPP-IV). Therefore, the usefulness of therapy involving GLP-1 peptides has been limited by their fast clearance and short half-lives. For example, GLP-1 (7-37) has a serum half-life of only 3 to 5 minutes. GLP-1 (7-36) amide has a time action of about 50 minutes when administered subcutaneously. Even analogs and derivatives that are resistant to endogenous protease cleavage, do not have half-lives long enough to avoid repeated administrations over a 24 hour period. For example, exenatide is resistant to DPP-IV, yet it still requires twice daily preprandial dosing because of the short half-life and significant variability in in vivo pharmacokinetics. NN2211, another compound currently in clinical trials, is a lipidated GLP-1 analogue. It is expected to be dosed once daily.

Fast clearance of a therapeutic agent is inconvenient in cases where it is desired to maintain a high blood level of the agent over a prolonged period of time since repeated administrations will then be necessary. Furthermore, a long-acting compound is particularly important for diabetic patients whose past treatment regimen has involved taking only oral medication. These patients often have an extremely difficult time transitioning to a regimen that involves multiple injections of medication. A GLP-1 therapy that has an increased half-life would have a significant advantage over other GLP-1 peptides and compounds in development.

Accordingly, there is a need to provide improved and/or modified versions of GLP-1 therapeutic proteins, which overcome one more of these and other problems known in the art. The mimetibody technology provides a novel delivery platform for peptide therapeutics. A GLP-1 mimetibody may provide a means of delivering the GLP-1 peptide in a sustained manner, providing an improvement over GLP-1 peptides currently in development. Furthermore, based upon its dimeric structure and its tissue distribution characteristics, a GLP-1 mimetibody could have differentiable features with regard to insulin secretion, β-cell preservation, and food intake.

SUMMARY OF THE INVENTION

The present invention provides improved human GLP-1 mimetibodies, including modified immunoglobulins, cleavage products and other specified portions and variants thereof, as well as GLP-1 mimetibody compositions, encoding or complementary nucleic acids, vectors, host cells, compositions, formulations, devices, transgenic animals, transgenic plants, and methods of making and using thereof, as described and/or enabled herein, in combination with what is known in the art.

Preferably, such GLP-1 mimetibodies are improved for expression, purification and/or stability by changing O-linked glycosylation sites (such as but not limited to Val-Xaa-Ser) to N-linked glycosylation sites (such as, but not limited to, Asn-Xaa-Ser or Gln-Xaa-Ser). The present invention provides such improvements to GLP-1 CH1 deleted mimetibodies (e.g., alanine) or o-glycosylation sites, such as but not limited to the sequence Val-Xaa-Ser, can be substituted with N-glycosylation sites, such as Asn-Xaa-Ser or Gln-Xaa-Ser, as may be preferred, e.g., but not limited to, as done at the following residues presented in the Sequence Listing: Val-Xaa-Ser (O-glycosylation site) changes to N-glycosylation site Asn-Xaa-Ser at: position 44 in SEQ ID NOS:2, 4, 7-14, position 64 in SEQ ID NOS:43, 45, position 82 in SEQ ID NOS:44, 46 and 51; position 88 in SEQ ID NOS:48, 50, 53-55, position 89 in SEQ ID NO:47, position 90 in SEQ ID NO:49; position 103 and/or 185 in SEQ ID NOS: 56 and 63; or position 39 in SEQ ID NOS:60 and 61; position 79 in SEQ ID NO:64 or any other suitable position as disclosed herein or as known in the art).

The present invention also provides at least one isolated GLP-1 mimetibody or specified portion or variant as described herein and/or as known in the art. The GLP-1 mimetibody can optionally comprise at least one CH3 region directly linked with at least one CH2 region directly linked with at least one portion of at least one hinge region or fragment thereof (H), directly linked with at least one partial variable region (V), directly linked with an optional linker sequence (L), directly linked to at least one GLP-1 therapeutic peptide (P).

In a preferred embodiment a pair of a CH3-CH2-hinge-partial V region sequence-linker-therapeutic peptide sequence, the pair optionally linked by association or covalent linkage, such as, but not limited to, at least one Cys-Cys disulfide bond or at least one CH4 or other immunoglobulin sequence. In one embodiment, a GLP-1 mimetibody comprises formula (I):

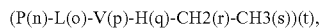

(P(n)-L(o)-V(p)-H(q)-CH2(r)-CH3(s))(t), wherein P is at least one bioactive GLP-1 peptide, variant or derivative, L is at least one linker sequence, which can be a polypeptide that provides structural flexibility by allowing the mimetibody to have alternative orientations and binding properties, V is at least one portion of a C-terminus of an immunoglobulin variable region, H is at least one portion of an immunoglobulin variable hinge region, CH2 is at least a portion of an immunoglobulin CH2 constant region, CH3 is at least a portion of an immunoglobulin CH3 constant region, n is an integer from 1 to 10, and o, p, q, r, s, and t can be independently an integer from 0 to 10, mimicing different types of immunoglobulin molecules, e.g., but not limited to IgG1, IgG2, IgG3, IgG4, IgA1, IgA2, IgM, IgD, IgE, or any subclass thereof, and the like, or any combination thereof.

The variable region of the antibody sequence can be, but not limited to, at least one portion of at least one of SEQ ID NOS:47-55, or fragment thereof as described in Table 1 or SEQ ID NOS:47-64, further optionally comprising at least one substitution, insertion or deletion as further described in FIGS. 1-9 of PCT publication WO 05/05604 (PCT US04/19898) filed Jun. 24, 2004 and published Jan. 20, 2005, with corresponding SEQ ID NOS: 1-9. The CH2, CH3 and hinge region can be, but not limited to, at least one portion of at least one of SEQ ID NOS:56-64, or fragment thereof as described in Table 1, further optionally comprising at least one substitution, insertion or deletion as further described in FIGS. 32-40 of PCT publication WO 05/05604 (PCT US04/19898) filed Jun. 24, 2004 and published Jan. 20, 2005, with corresponding SEQ ID NOS:32-40.

Thus, a GLP-1 mimetibody of the present invention mimics at least a portion of an antibody or immunoglobulin structure or function with its inherent properties and functions, while providing a GLP-1 therapeutic peptide and its inherent or acquired in vitro, in vivo or in situ properties or activities. The various portions of the antibody and therapeutic peptide portions of GLP-1 mimetibody of the present invention can vary as described herein in combination with what is known in the art.

The present invention also provides at least one isolated GLP-1 mimetibody or specified portion or variant that has at least one activity, such as, but not limited to known biological activities of at least one bioactive GLP-1 peptide or polypeptide corresponding to the P portion of formula (I), as described herein or known in the art.

In one aspect, the present invention provides at least one isolated human GLP-1 mimetibody comprising at least one polypeptide sequence of SEQ ID NO: 1, or optionally with one or more substitutions, deletions or insertions as described herein or as known in the art. In another aspect, at least one GLP-1 mimetibody or specified portion or variant of the invention mimics the binding of at least one GLP-1 peptide or polypeptide corresponding to the P portion of the mimetibody in formula (I), to at least one epitope comprising at least 1-3, to the entire amino acid sequence of at least one ligand, e.g., but not limited to, a GLP-1 receptor, or fragment thereof, wherein the ligand binds to at least a portion of SEQ ID NO: 1, or optionally with one or more substitutions, deletions or insertions as described herein or as known in the art. The at least one GLP-1 mimetibody can optionally bind GLP-1 receptor with an affinity of at least $10^{-7}$, at least $10^{-8}$, at least $10^{-9}$ M, at least $10^{-10}$ M, at least $10^{-11}$ M, or at least $10^{-12}$ M. A GLP-1 mimetibody can thus be screened for a corresponding activity according to known methods, such as, but not limited to the binding activity towards a receptor or fragment thereof.

The present invention further provides at least one anti-idiotype antibody to at least one GLP-1 mimetibody of the present invention. The anti-idiotype antibody or fragment specifically binds at least one GLP-1 mimetibody of the present invention. The anti-idiotype antibody includes any protein or peptide containing molecule that comprises at least a portion of an immunoglobulin molecule, such as but not limited to at least one complimetarity determining region (CDR) of a heavy or light chain or a ligand binding portion thereof, a heavy chain or light chain variable region, a heavy chain or light chain constant region, a framework region, or any portion thereof, that competitively binds a GLP-1 ligand binding region of at least one GLP-1 mimetibody of the present invention. Such idiotype antibodies of the invention can include or be derived from any mammal, such as but not limited to a human, a mouse, a rabbit, a rat, a rodent, a primate, and the like.

The present invention provides, in one aspect, isolated nucleic acid molecules comprising, complementary, having significant identity or hybridizing to, a polynucleotide encoding at least one GLP-1 mimetibody or GLP-1 mimetibody anti-idiotype antibody, or specified portions or variants thereof, comprising at least one specified sequence, domain, portion or variant thereof. The present invention further provides recombinant vectors comprising at least one of said isolated GLP-1 mimetibody or GLP-1 mimetibody anti-idiotype antibody encoding nucleic acid molecules, host cells containing such nucleic acids and/or recombinant vectors, as well as methods of making and/or using such GLP-1 mimetibody or GLP-1 mimetibody anti-idiotype antibody nucleic acids, vectors and/or host cells.

Also provided is an isolated nucleic acid encoding at least one isolated mammalian GLP-1 mimetibody or GLP-1 mimetibody anti-idiotype antibody; an isolated nucleic acid vector comprising the isolated nucleic acid, and/or a prokaryotic or eukaryotic host cell comprising the isolated nucleic acid. The host cell can optionally be at least one selected from COS-1, COS-7, HEK293, BHK21, CHO, BSC-1, Hep G2, 653, SP2/0, 293, HeLa, myeloma, or lymphoma cells, or any derivative, immortalized or transformed cell thereof.

The present invention also provides at least one method for expressing at least one GLP-1 mimetibody or GLP-1 mimetibody anti-idiotype antibody, or specified portion or variant in a host cell, comprising culturing a host cell as described herein and/or as known in the art under conditions wherein at least one GLP-1 mimetibody or GLP-1 mimetibody anti-idiotype antibody, or specified portion or variant is expressed in detectable and/or recoverable amounts. Also provided is a method for producing at least one GLP-1 mimetibody or GLP-1 mimetibody anti-idiotype antibody, comprising translating the GLP-1 mimetibody or GLP-1 mimetibody anti-idiotype antibody encoding nucleic acid under conditions in vitro, in vivo or in situ, such that the GLP-1 mimetibody or GLP-1 mimetibody anti-idiotype antibody is expressed in detectable or recoverable amounts.

Also provided is a method for producing at least one isolated human GLP-1 mimetibody or GLP-1 anti-idiotype antibody of the present invention, comprising providing a host cell or transgenic animal or transgenic plant capable of expressing in recoverable amounts the GLP-1 mimetibody or GLP-1 anti-idiotype antibody.

Further provided in the present invention is at least one GLP-1 mimetibody produced by the above methods.

The present invention also provides at least one composition comprising (a) an isolated GLP-1 mimetibody or specified portion or variant encoding nucleic acid and/or GLP-1 mimetibody as described herein; and (b) a suitable carrier or diluent. The carrier or diluent can optionally be pharmaceutically acceptable, according to known methods. The composition can optionally further comprise at least one further compound, protein or composition.

Also provided is a composition comprising at least one isolated human GLP-1 mimetibody and at least one pharmaceutically acceptable carrier or diluent. The composition can optionally further comprise an effective amount of at least one compound or protein selected from at least one of a detectable label or reporter, an anti-infective drug, a diabetes or insuling metabolism related drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplactic, an immunomodulation drug, an ophthalmic, otic or nasal drug, a topical drug, a nutritional drug, a TNF antagonist, an antirheumatic, a muscle relaxant, a narcotic, a non-steroid anti-inflammatory drug (NTHE), an analgesic, an anesthetic, a sedative, a local anethetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

The present invention also provides at least one composition, device and/or method of delivery of a therapeutically or prophylactically effective amount of at least one GLP-1 mimetibody or specified portion or variant, according to the present invention.

The present invention further provides at least one GLP-1 mimetibody method or composition, for administering a therapeutically effective amount to modulate or treat at least one GLP-1 related condition in a cell, tissue, organ, animal or patient and/or, prior to, subsequent to, or during a related condition, as known in the art and/or as described herein.

The present invention further provides at least one GLP-1 mimetibody, specified portion or variant in a method or composition, when administered in a therapeutically effective amount, for modulation, for treating or reducing the symptoms of, at least one metabolic, immune, cardiovascular, infectious, malignant, and/or neurologic disease in a cell, tissue, organ, animal or patient and/or, as needed in many different conditions, such as but not limited to, prior to, subsequent to, or during a related disease or treatment condition, as known in the art.

The present invention further provides at least one GLP-1 mimetibody, specified portion or variant in a method or composition, when administered in a therapeutically effective amount, for modulation, for treating or reducing the symptoms of at least one of a diabetes or insuling metabolism related disorder, a bone and joint disorder, cardiovascular disorder, a dental or oral disorder, a dermatologic disorder, an ear, nose or throat disorder, an endocrine or metabolic disorder, a gastrointestinal disorder, a gynecologic disorder, a hepatic or biliary disorder, a an obstetric disorder, a hematologic disorder, an immunologic or allergic disorder, an infectious disease, a musculoskeletal disorder, a oncologic disorder, a neurologic disorder, a nutritional disorder, an opthalmologic disorder, a pediatric disorder, a poisoning disorder, a psychiatric disorder, a renal disorder, a pulmonary disorder, or any other known disorder, (See, e.g., The Merck Manual, 17th ed., Merck Research Laboratories, Merck and Co., Whitehouse Station, N.J. (1999), entirely incorporated herein by reference), as needed in many different conditions, such as but not limited to, prior to, subsequent to, or during a related disease or treatment condition, as known in the art.

The present invention also provides at least one composition, device and/or method of delivery, for diagnosing GLP-1 related conditions, of at least one GLP-1 mimetibody, according to the present invention.

The present invention further provides at least one GLP-1 mimetibody method or composition, for diagnosing at least one GLP-1 related condition in a cell, tissue, organ, animal or patient and/or, prior to, subsequent to, or during a related condition, as known in the art and/or as described herein.

Also provided is a method for diagnosing or treating a disease condition in a cell, tissue, organ or animal, comprising: (a) contacting or administering a composition comprising an effective amount of at least one isolated human GLP-1 mimetibody of the invention with, or to, the cell, tissue, organ or animal. The method can optionally further comprise using an effective amount of 0.001-50 mg/kilogram of the cells, tissue, organ or animal per 0-24 hours, 1-7 days, 1-52 weeks, 1-24 months, 1-30 years or any range or value therein. The method can optionally further comprise using the contacting or the administrating by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal. The method can optionally further comprise administering, prior, concurrently or after the (a) contacting or administering, at least one composition comprising an effective amount of at least one compound or protein selected from at least one of a detectable label or reporter, an anti-infective drug, a diabetes or insuling metabolism related drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplactic, an immunomodulation drug, an ophthalmic, otic or nasal drug, a topical drug, a nutritional drug, a TNF antagonist, an antirheumatic, a muscle relaxant, a narcotic, a non-steroid anti-inflammatory drug (NSAID), an analgesic, an anesthetic, a sedative, a local anethetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

Also provided is a medical device, comprising at least one isolated human GLP-1 mimetibody of the invention, wherein the device is suitable to contacting or administering the at least one GLP-1 mimetibody by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

Also provided is an article of manufacture for human pharmaceutical or diagnostic use, comprising packaging material and a container comprising a solution or a lyophilized form of at least one isolated human GLP-1 mimetibody of the present invention. The article of manufacture can optionally comprise having the container as a component of a parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

The present invention further provides any invention described herein.

DESCRIPTION OF THE FIGURES

FIG. 1 illustrates the nucleotide (SEQ ID NO: 75) and peptide (SEQ ID NO: 76) sequences of GLP-1 MMB in an IgG4scaffold showing important functional domains.

FIG. 2A shows that GLP-1 MMB binds to HEK293 cells over-expressing the GLP-1R. Grey area: GLP-1 MMB but no secondary; grey line: secondary only; dotted line, negative control MMB and secondary; black line: GLP-1 MMB and secondary. FIG. 2B shows that the GLP-1 MMB does not bind to the control HEK293 cells. Grey area: GLP-1 MMB but no secondary; black line: secondary only; grey line: GLP-1 MMB and secondary. FIG. 2C shows that a GLP-1 peptide analogue (A2S) is able to compete with GLP-1 MMB for binding to HEK293 cells over-expressing the GLP-1 R. Grey area: GLP-1 MMB but no secondary; black line: GLP-1 MMB and secondary; break line: GLP-1 MMB, 0.2 nM competitor, secondary; dotted line: GLP-1 MMB, 20 nM competitor, secondary; grey line: GLP-1 MMB, 100 nM competitor, secondary).

FIG. 3A: wt GLP-1 MMB in IgG1 scaffold; FIG. 3B: GLP-1 peptide; FIG. 3C: GLP-1 (A2G) MMB in IgG4 (Ala/Ala, Ser->Pro) scaffold; FIG. 3D: GLP-1 (A2S) MMB in IgG4 (Ala/Ala, Ser->Pro) scaffold; FIG. 3E: wt GLP-1 MMB in IgG4 (Ala/Ala, Ser->Pro) scaffold.

FIG. 6 demonstrates that GLP-1 MMBs cause insulin secretion in RINm cells.

DESCRIPTION OF THE INVENTION

Figure 2A:
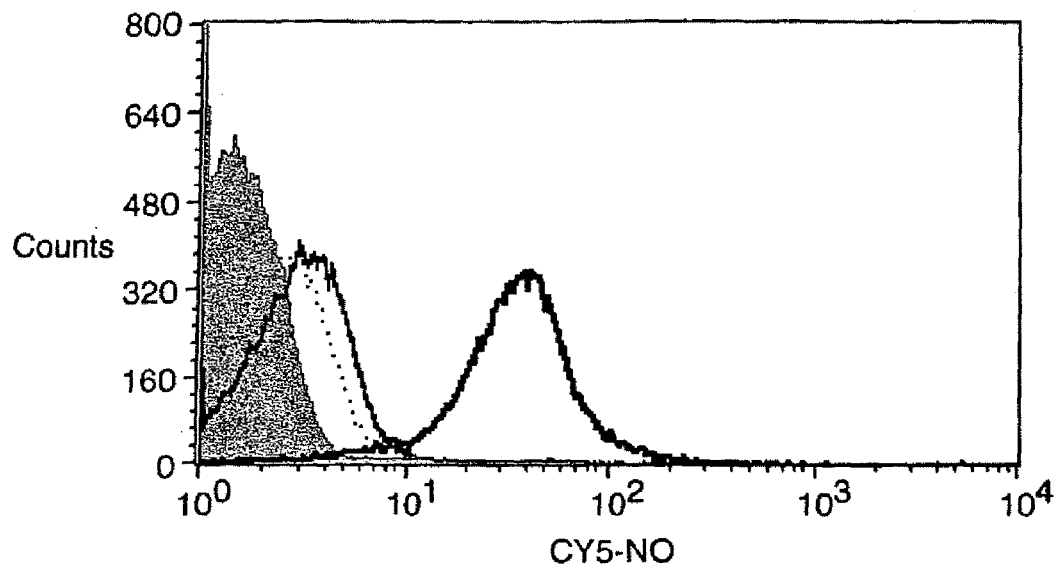
FIGS. 2A-2C illustrate FACS binding assays of GLP-1 MMB.

The present invention provides isolated, recombinant and/or synthetic mimetibodies or specified portions or variants, as well as compositions and encoding nucleic acid molecules comprising at least one polynucleotide encoding at least one GLP-1 mimetibody. Such mimetibodies or specified portions or variants of the present invention comprise specific GLP-1 mimetibody sequences, domains, fragments and specified variants thereof, and methods of making and using said nucleic acids and mimetibodies or specified portions or variants, including therapeutic compositions, methods and devices.

Preferably, such GLP-1 mimetibodies are improved for expression, purification and/or stability by changing O-linked glycosylation sites (such as but not limited to Val-Xaa-Ser) to N-linked glycosylation sites (such as, but not limited to, Asn-Xaa-Ser or Gln-Xaa-Ser). The present invention provides such improvements to GLP-1 CH1 deleted mimetibodies.

The present invention also provides at least one isolated GLP-1 mimetibody or specified portion or variant as described herein and/or as known in the art. The GLP-1 mimetibody can optionally comprise at least one CH3 region directly linked with at least one CH2 region directly linked with at least one hinge region or fragment thereof (H), directly linked with at least one partial variable region (V), directly linked with an optional linker sequence (L), directly linked to at least one GLP-1 therapeutic peptide (P).

In a preferred embodiment a GLP-1 mimetibody comprises formula (I):

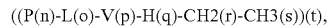

((P(n)-L(o)-V(p)-H(q)-CH2(r)-CH3(s))(t), where P is at least one bioactive GLP-1 polypeptide, L is at least one linker sequence, which can be a polypeptide that provides structural flexibility by allowing the mimetibody to have alternative orientations and binding properties, V is at least one portion of a C-terminus of an immunoglobulin variable region, H is at least one portion of an immunoglobulin variable hinge region, CH2 is at least a portion of an immunoglobulin CH2 constant region, CH3 is at least a portion of an immunoglobulin CH3 constant region, m, n, o, p, q, r, s and t can be independently an integer between and including 0 and 10, mimicing different types of immunoglobulin molecules, e.g., but not limited to IgG1, IgG2, IgG3, IgG4, IgA1, IgA2, IgM, IgD, IgE, or any subclass thereof, and the like, or any combination thereof.

Preferably, such GLP-1 mimetibodies are improved for expression, purification and/or stability by changing O-linked glycosylation sites (such as but not limited to Val-Xaa-Ser) to N-linked glycosylation sites (such as, but not limited to, Asn-Xaa-Ser or Gln-Xaa-Ser). The present invention provides such improvements to GLP-1 CH 1 deleted mimetibodies.

Thus, a GLP-1 mimetibody of the present invention mimics an antibody structure with its inherent properties and functions, while providing a therapeutic peptide and its inherent or acquired in vitro, in vivo or in situ properties or activities. In a preferred embodiment where t=1, the monomer CH3-CH2-hinge-partial J sequence-linker-therapeutic peptide can be linked to other monomers by association or covalent linkage, such as, but not limited to, a Cys-Cys disulfide bond. The various portions of the antibody and the GLP-1 therapeutic peptide portions of at least one GLP-1 mimetibody of the present invention can vary as described herein in combination with what is known in the art.

The portion of CH3-CH2-hinge may be extensively modified to form a variant in accordance with this invention, provided binding to the salvage receptor is maintained. In such variants, one may remove one or more native sites that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. A variant of CH3-CH2-hinge may lack one or more native sites or residues that affect or are involved in (1) disulfide bond formation, (2) incompatibility with a selected host cell, (3) heterogeneity upon expression in a selected host cell, (4) glycosylation, (5) interaction with complement, (6) binding to an Fc receptor other than a salvage receptor, or (7) antibody-dependent cellular cytotoxicity (ADCC). Exemplary CH3-CH2-hinge variants include molecules and sequences in which: 1. Sites involved in disulfide bond formation are removed. Such removal may avoid reaction with other cysteine-containing proteins present in the host cell used to produce the molecules of the invention. For this purpose, the cysteine residues may be deleted or substituted with other amino acids (e.g., alanyl, seryl). Even when cysteine residues are removed, the single chain CH3-CH2-hinge domains can still form a dimeric CH3-CH2-hinge domain that is held together non-covalently; 2. The CH3-CH2-hinge region is modified to make it more compatible with a selected host cell. For example, when the molecule is expressed recombinantly in a bacterial cell such as E. coli, one may remove the PA sequence in the hinge, which may be recognized by a digestive enzyme in *E. coli* such as proline iminopeptidase; 3. A portion of the hinge region is deleted or substituted with other amino acids to prevent heterogeneity when expressed in a selected host cell; 4. One or more glycosylation sites are removed. Residues that are typically glycosylated (e.g., valine or asparagine) may confer cytolytic response. Such residues may be deleted or substituted with unglycosylated residues (e.g., alanine) or o-glycosylation sites, such as but not limited to the sequence Val-Xaa-Ser, can be substituted with N-glycosylation sites, such as Asn-Xaa-Ser or Gln-Xaa-Ser, as may be preferred, e.g., as done at the following residues presented in the Sequence Listing: Val-Xaa-Ser (O-glycosylation site) changes to N-glycosylation site Asn-Xaa-Ser at: position 44 in SEQ ID NOS:2, 4, 7-14, position 64 in SEQ ID NOS:43, 45, position 82 in SEQ ID NOS:44, 46 and 51; position 88 in SEQ ID NOS:48, 50, 53-55, position 89 in SEQ ID NO:47, position 90 in SEQ ID NO:49; position 103 and/or 185 in SEQ ID NOS:56 and 63; or position 39 in SEQ ID NOS:60 and 61; position 79 in SEQ ID NO:64 or any other suitable position as disclosed herein or as known in the art); 5. Sites involved in interaction with complement, such as the C1q binding site, are removed. Complement recruitment may not be advantageous for the molecules of this invention and so may be avoided with such a variant; 6. Sites are removed that affect binding to Fc receptors other than a salvage receptor. The CH3-CH2-hinge region may have sites for interaction with certain white blood cells that are not required for the fusion molecules of the present invention and so may be removed; 7. The ADCC site is removed. ADCC sites are known in the art; see, for example, Molec. Immunol. 29 (5): 633-9 (1992) with regard to ADCC sites in IgG1. These sites, as well, are not required for the fusion molecules of the present invention and so may be removed.

Linker polypeptide provides structural flexibility by allowing the mimetibody to have alternative orientations and binding properties. When present, its chemical structure is not critical. The linker is preferably made up of amino acids linked together by peptide bonds. Thus, in preferred embodiments, the linker is made up of from 1 to 20 amino acids linked by peptide bonds, wherein the amino acids are selected from the 20 naturally occurring amino acids. Some of these amino acids may be glycosylated, as is well understood by those in the art. In a more preferred embodiment, the 1 to 20 amino acids are selected from glycine, alanine, serine, proline, asparagine, glutamine, and lysine. Even more preferably, a linker is made up of a majority of amino acids that are sterically unhindered, such as glycine and alanine. Thus, preferred linkers are poly(Gly-Ser), polyglycines (particularly (Gly)$_4$ (SEQ ID NO: 73), (Gly)$_5$ (SEQ ID NO: 74)), poly(Gly-Ala), and polyalanines. Other specific examples of linkers are: (Gly)$_3$Lys(Gly)$_4$ (SEQ ID NO:65), (Gly)$_3$AsnGlySer(Gly)$_2$ (SEQ ID NO:66), (Gly)$_3$Cys(Gly)$_4$ (SEQ ID NO:67), and GlyProAsnGlyGly (SEQ ID NO:68).

To explain the above nomenclature, for example, (Gly)$_3$Lys(Gly)$_4$ (SEQ ID NO: 65) means Gly-Gly-Gly-Lys-Gly-Gly-Gly-Gly (SEQ ID NO: 65). Combinations of Gly and Ala are also preferred. The linkers shown here are exemplary; linkers within the scope of this invention may be much longer and may include other residues.

Non-peptide linkers are also possible. For example, alkyl linkers such as —NH—(CH$_2$)s-C(O)—, wherein s=2-20 could be used. These alkyl linkers may further be substituted by any non-sterically hindering group such as lower alkyl (e.g., C$_1$-C$_6$) lower acyl, halogen (e.g., Cl, Br), CN, NH2, phenyl, etc. An exemplary non-peptide linker is a PEG linker which has a molecular weight of 100 to 5000 kD, preferably 100 to 500 kD. The peptide linkers may be altered to form derivatives in the same manner as described above.

As used herein, a "GLP-1 peptide," or "GLP-1 peptide, variant, or derivative" can be at least one GLP-1 peptide, GLP-1 fragment, GLP-1 homolog, GLP-1 analog, or GLP-1 derivative. A GLP-1 peptide has from about twenty-five to about forty-five naturally occurring or non-naturally occurring amino acids that have sufficient homology to native GLP-1 (7-37) such that they exhibit insulinotropic activity by binding to the GLP-1 receptor on β-cells in the pancreas. GLP-1 (7-37) has the amino acid sequence of SEQ ID NO: 15:

His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Glu-Trp-Leu-Val-Lys-Gly-Arg-Gly.

A GLP-1 fragment is a polypeptide obtained after truncation of one or more amino acids from the N-terminus and/or C-terminus of GLP-1 (7-37) or an analog or derivative thereof. A GLP-1 homolog is a peptide in which one or more amino acids have been added to the N-terminus and/or C-terminus of GLP-1 (7-37), or fragments or analogs thereof. A GLP-1 analog is a peptide in which one or more amino acids of GLP-1 (7-37) have been modified and/or substituted. A GLP-1 analog has sufficient homology to GLP-1 (7-37) or a fragment of GLP-1 (7-37) such that the analog has insulinotropic activity. A GLP-1 derivative is defined as a molecule having the amino acid sequence of a GLP-1 peptide, a GLP-1 homolog or a GLP-1 analog, but additionally having chemical modification of one or more of its amino acid side groups, α-carbon atoms, terminal amino group, or terminal carboxylic acid group.

Numerous active GLP-1 fragments, analogs and derivatives are known in the art and any of these analogs and derivatives can also be part of the GLP-1 mimetibody of the present invention. Some GLP-1 analogs and GLP-1 fragments known in the art are disclosed in U.S. Pat. Nos. 5,118,666, 5,977,071, and 5,545,618, and Adelhorst, et al., *J. Biol. Chem.* 269:6275 (1994). Examples include, but not limited to, GLP-1 (7-34), GLP-1 (7-35), GLP-1 (7-36), Gln9-GLP-1 (7-37), D-Gln9-GLP-1(7-37), Thr16-Lys18-GLP-1 (7-37), and Lys18-GLP-1 (7-37).

A "GLP-1 mimetibody," "GLP-1 mimetibody portion," or "GLP-1 mimetibody fragment" and/or "GLP-1 mimetibody variant" and the like has, mimics or simulates at least one biological activity, such as but not limited to ligand binding, in vitro, in situ and/or preferably in vivo, of at least one GLP-1 peptide, variant or derivative, such as but not limited to at least one of SEQ ID NO: 1. For example, a suitable GLP-1 mimetibody, specified portion, or variant can also modulate, increase, modify, activate, at least one GLP-1 receptor signaling or other measurable or detectable activity.

GLP-1 mimetibodies useful in the methods and compositions of the present invention are characterized by suitable affinity binding to protein ligands, for example, GLP-1 receptors, and optionally and preferably having low toxicity. In particular, a GLP-1 mimetibody, where the individual components, such as the portion of variable region, constant region (without a CH1 portion) and framework, or any portion thereof (e.g., a portion of the J, D or V rgions of the variable heavy or light chain; at least a portion of at least one hinge region, the constant heavy chain or light chain, and the like) individually and/or collectively optionally and preferably possess low immunogenicity, is useful in the present invention. The mimetibodies that can be used in the invention are optionally characterized by their ability to treat patients for extended periods with good to excellent alleviation of symptoms and low toxicity. Low immunogenicity and/or high affinity, as well as other undefined properties, may contribute to the therapeutic results achieved. "Low immunogenicity" is defined herein as raising significant HAMA, HACA or HAHA responses in less than about 75%, or preferably less than about 50, 45, 40, 35, 30, 35, 20, 15, 10, 9, 8, 7, 6, 5, 4, 3, 2, and/or 1% of the patients treated and/or raising low titres in the patient treated (less than about 300, preferably less than about 100 measured with a double antigen enzyme immunoassay) (see, e.g., Elliott et al., *Lancet* 344:1125-1127 (1994)).

Utility. The isolated nucleic acids of the present invention can be used for production of at least one GLP-1 mimetibody, fragment or specified variant thereof, which can be used to effect in an cell, tissue, organ or animal (including mammals and humans), to modulate, treat, alleviate, help prevent the incidence of, or reduce the symptoms of, at least one protein related condition, selected from, but not limited to, at least one of a diabetes related disorder, an insulin metabolism related disorder, an immune disorder or disease, a cardiovascular disorder or disease, an infectious, malignant, and/or neurologic disorder or disease, as well as other known or specified protein related conditions.

Such a method can comprise administering an effective amount of a composition or a pharmaceutical composition comprising at least one GLP-1 mimetibody or specified portion or variant to a cell, tissue, organ, animal or patient in need of such modulation, treatment, alleviation, prevention, or reduction in symptoms, effects or mechanisms. The effective amount can comprise an amount of about 0.0001 to 500 mg/kg per single or multiple administration, or to achieve a serum concentration of 0.01-5000 µg/ml serum concentration per single or multiple administration, or any effective range or value therein, as done and determined using known methods, as described herein or known in the relevant arts.

Citations. All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2003); Sambrook, et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2003); Colligan et al., Current Protocols in Protein Science, John Wiley & Sons, NY, N.Y., (1997-2003).

Mimetibodies of the Present Invention. The GLP-1 mimetibody can optionally comprise at least one CH3 region directly linked with at least one CH2 region directly linked with at least one portion of at least one hinge region fragment (H), such as comprising at least one core hinge region, directly linked with at least one partial variable region (V), directly linked with an optional linker sequence (L), directly linked to at least one GLP-1 therapeutic peptide (P). In a preferred embodiment, a pair of a CH3-CH2-H-V-L-P can be linked by association or covalent linkage, such as, but not limited to, a Cys-Cys disulfide bond. Thus, a GLP-1 mimetibody of the present invention mimics an antibody structure with its inherent properties and functions, while providing a therapeutic peptide and its inherent or acquired in vitro, in vivo or in situ properties or activities. The various portions of the antibody and therapeutic peptide portions of at least one GLP-1 mimetibody of the present invention can vary as described herein in combination with what is known in the art.

Mimetibodies of the present invention thus provide at least one suitable property as compared to known proteins, such as, but not limited to, at least one of increased half-life, increased activity, more specific activity, increased avidity, increased or decreased off rate, a selected or more suitable subset of activities, less immunogenicity, increased quality or duration of at least one desired therapeutic effect, less side effects, and the like.

Fragments of mimetibodies according to Formula (I) can be produced by enzymatic cleavage, synthetic or recombinant techniques, as known in the art and/or as described herein. Mimetibodies can also be produced in a variety of truncated forms using antibody genes in which one or more stop codons have been introduced upstream of the natural stop site. The various portions of mimetibodies can be joined together chemically by conventional techniques, or can be prepared as a contiguous protein using genetic engineering techniques. For example, a nucleic acid encoding at least one of the constant regions of a human antibody chain can be expressed to produce a contiguous protein for use in mimetibodies of the present invention. See, e.g., Ladner et al., U.S. Pat. No. 4,946, 778 and Bird, R. E. et al., *Science,* 242: 423-426 (1988), regarding single chain antibodies.

As used herein, the term "human mimetibody" refers to an antibody in which substantially every part of the protein (e.g., GLP-1 peptide, $C_H$ domains (e.g., $C_H2$, $C_H3$), hinge, V) is expected to be substantially non-immunogenic in humans with only minor sequence changes or variations. Such changes or variations optionally and preferably retain or reduce the immunogenicity in humans relative to non-modified human antibodies, or mimetibodies of the present invention. Thus, a human antibody and corresponding GLP-1 mimetibody of the present invention is distinct from a chimeric or humanized antibody. It is pointed out that the GLP-1 mimetibody can be produced by a non-human animal or cell that is capable of expressing human immunoglobulins (e.g., heavy chain and/or light chain) genes.

Human mimetibodies that are specific for at least one protein ligand thereof can be designed against an appropriate ligand, such as an isolated GLP-1 receptor, or a portion thereof (including synthetic molecules, such as synthetic peptides). Preparation of such mimetibodies are performed using known techniques to identify and characterize ligand binding regions or sequences of at least one protein or portion thereof.

In a preferred embodiment, at least one GLP-1 mimetibody or specified portion or variant of the present invention is produced by at least one cell line, mixed cell line, immortalized cell or clonal population of immortalized and/or cultured cells. Immortalized protein producing cells can be produced using suitable methods. Preferably, the at least one GLP-1 mimetibody or specified portion or variant is generated by providing nucleic acid or vectors comprising DNA derived or having a substantially similar sequence to, at least one human immunoglobulin locus that is functionally rearranged, or which can undergo functional rearrangement, and which further comprises a mimetibody structure as described herein, e.g., but not limited to Formula (I), wherein portions of C-terminal variable regions can be used for V, hinge regions for H, CH2 for CH2 and CH3 for CH3, as known in the art.

The term "functionally rearranged," as used herein refers to a segment of nucleic acid from an immunoglobulin locus that has undergone V(D)J recombination, thereby producing an immunoglobulin gene that encodes an immunoglobulin chain (e.g., heavy chain), or any portion thereof. A functionally rearranged immunoglobulin gene can be directly or indirectly identified using suitable methods, such as, for example, nucleotide sequencing, hybridization (e.g., Southern blotting, Northern blotting) using probes that can anneal to coding joints between gene segments or enzymatic amplification of immunoglobulin genes (e.g., polymerase chain reaction) with primers that can anneal to coding joints between gene segments. Whether a cell produces a GLP-1 mimetibody or portion or variant comprising a particular variable region or a variable region comprising a particular sequence (e.g., at least one P sequence) can also be determined using suitable methods.

Mimetibodies, specified portions and variants of the present invention can also be prepared using at least one GLP-1 mimetibody or specified portion or variant encoding nucleic acid to provide transgenic animals or mammals, such as goats, cows, horses, sheep, and the like, that produce such mimetibodies or specified portions or variants in their milk. Such animals can be provided using known methods as applied for antibody encoding sequences. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference.

Mimetibodies, specified portions and variants of the present invention can additionally be prepared using at least one GLP-1 mimetibody or specified portion or variant encoding nucleic acid to provide transgenic plants and cultured plant cells (e.g., but not limited to tobacco and maize) that produce such mimetibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize or corn have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain mimetibodies (scFv's), including tobacco seeds and potato tubers. See, e.g., Conrad et al., Plant Mol. Biol. 38:101-109 (1998) and references cited therein. Thus, mimetibodies, specified portions and variants of the present invention can also be produced using transgenic plants, according to know methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. The above references are entirely incorporated herein by reference.

The mimetibodies of the invention can bind human protein ligands with a wide range of affinities ($K_D$). In a preferred embodiment, at least one human GLP-1 mimetibody of the present invention can optionally bind at least one protein ligand with high affinity. For example, at least one GLP-1 mimetibody of the present invention can bind at least one protein ligand with a $K_D$ equal to or less than about $10^{-7}$ M or, more preferably, with a $K_D$ equal to or less than about 0.1-9.9 (or any range or value therein)$\times 10^{-7}$, $10^{-8}$, $10^{-9}$, $10^{-10}$, $10^{-11}$, $10^{-12}$, or $10^{-13}$ M, or any range or value therein.

The affinity or avidity of a GLP-1 mimetibody for at least one protein ligand can be determined experimentally using any suitable method, e.g., as used for determining antibody-antigen binding affinity or avidity. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular GLP-1 mimetibody-ligand interaction can vary if measured under different conditions (e.g., salt concentration, pH). Thus, measurements of affinity and other ligand-binding parameters (e.g., $K_D$, $K_a$, $K_d$) are preferably made with standardized solutions of GLP-1 mimetibody and ligand, and a standardized buffer, such as the buffer described herein or known in the art.

Nucleic Acid Molecules. Using the information provided herein, such as the nucleotide sequences encoding at least 90-100% of the contiguous amino acids of at least one of SEQ ID NOS: 1 and 6, as well as at least one portion of an antibody, wherein the above sequences are inserted as the P sequence of Formula (I) to provide a GLP-1 mimetibody of the present invention, further comprising specified fragments, variants or consensus sequences thereof, or a deposited vector comprising at least one of these sequences, a nucleic acid molecule of the present invention encoding at least one GLP-1 mimetibody or specified portion or variant can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combination thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, nucleic acid molecules comprising the coding sequence for a GLP-1 mimetibody or specified portion or variant; and nucleic acid molecules which comprise a nucleotide sequence substantially different from those described above but which, due to the degeneracy of the genetic code, still encode at least one GLP-1 mimetibody as described herein and/or as known in the art. Of course, the genetic code is well known in the art. Thus, it would be routine for one skilled in the art to generate such degenerate nucleic acid variants that code for specific GLP-1 mimetibody or specified portion or variants of the present invention. See, e.g., Ausubel, et al., supra, and such nucleic acid variants are included in the present invention.

As indicated herein, nucleic acid molecules of the present invention which comprise a nucleic acid encoding a GLP-1 mimetibody or specified portion or variant can include, but are not limited to, those encoding the amino acid sequence of a GLP-1 mimetibody fragment, by itself; the coding sequence for the entire GLP-1 mimetibody or a portion thereof; the coding sequence for a GLP-1 mimetibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding a GLP-1 mimetibody or specified portion or variant can be fused to a marker sequence, such as a sequence encoding a peptide that facilitates purification of the fused GLP-1 mimetibody or specified portion or variant comprising a GLP-1 mimetibody fragment or portion.

Polynucleotides Which Selectively Hybridize to a Polynucleotide as Described Herein. The present invention provides isolated nucleic acids that hybridize under selective hybridization conditions to a polynucleotide disclosed herein, or others disclosed herein, including specified variants or portions thereof. Thus, the polynucleotides of this embodiment can be used for isolating, detecting, and/or quantifying nucleic acids comprising such polynucleotides.

Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 40-99% sequence identity and can be employed to identify orthologous or paralogous sequences.

Optionally, polynucleotides of this invention will encode at least a portion of a GLP-1 mimetibody or specified portion or variant encoded by the polynucleotides described herein. The polynucleotides of this invention embrace nucleic acid sequences that can be employed for selective hybridization to a polynucleotide encoding a GLP-1 mimetibody or specified portion or variant of the present invention. See, e.g., Ausubel, supra; Colligan, supra, each entirely incorporated herein by reference.

Construction of Nucleic Acids. The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. See, e.g., Ausubel, supra; or Sambrook, supra.

Recombinant Methods for Constructing Nucleic Acids. The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under suitable stringency conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra).

Synthetic Methods for Constructing Nucleic Acids. The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes. The present invention further provides recombinant expression cassettes comprising a nucleic acid of the present invention. A nucleic acid sequence of the present invention, for example a cDNA or a genomic sequence encoding a GLP-1 mimetibody or specified portion or variant of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution, as known in the art. A polynucleotide of the present invention can be expressed in either sense or anti-sense orientation as desired. It will be appreciated that control of gene expression in either sense or anti-sense orientation can have a direct impact on the observable characteristics. Another method of suppression is sense suppression. Introduction of nucleic acid configured in the sense orientation has been shown to be an effective means by which to block the transcription of target genes.

Vectors And Host Cells. The present invention also relates to vectors that include isolated nucleic acid molecules of the present invention, host cells that are genetically engineered with the recombinant vectors, and the production of at least one GLP-1 mimetibody or specified portion or variant by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced into a cell using suitable known methods, such as electroporation and the like, other known methods include the use of the vector as a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites optionally for at least one of transcription initiation, termination and, in the transcribed region, a ribosome binding site for translation.

The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one GLP-1 mimetibody or specified portion or variant of the present invention can be expressed in a modified form, such as a fusion protein, and can include not only secretion signals, but also additional heterologous functional regions. For instance, a region of additional amino acids, particularly charged amino acids, can be added to the N-terminus of a GLP-1 mimetibody or specified portion or variant to improve stability and persistence in the host cell, during purification, or during subsequent handling and storage. Also, peptide moieties can be added to a GLP-1 mimetibody or specified portion or variant of the present invention to facilitate purification. Such regions can be removed prior to final preparation of a GLP-1 mimetibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention.

Illustrative of cell cultures useful for the production of the mimetibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610, DG-44) and BSC-1 (e.g., ATCC CRL-26) cell lines, hepG2 cells, P3X63Ag8.653, SP2/0-Ag14, 293 cells, HeLa cells and the like, which are readily available from, for example, American Type Culture Collection, Manassas, Va. Preferred host cells include cells of lymphoid origin such as myeloma and lymphoma cells. Particularly preferred host cells are P3X63Ag8.653 cells (ATCC Accession Number CRL-1580) and SP2/0-Ag14 cells (ATCC Accession Number CRL-1851).

Expression vectors for these cells can include one or more of the following expression control sequences, such as, but not limited to an origin of replication; a promoter (e.g., late or early SV40 promoters, the CMV promoter (e.g., U.S. Pat. Nos. 5,168,062; 5,385,839), an HSV tk promoter, a pgk (phosphoglycerate kinase) promoter, an EF-1 alpha promoter (e.g., U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of a GLP-1 mimetibody or specified portion or variant thereof. A GLP-1 mimetibody or specified portion or variant can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2003), e.g., Chapters 1, 4, 6, 8, 9, 10, each entirely incorporated herein by reference.

Mimetibodies or specified portions or variants of the present invention include naturally purified products, products of chemical synthetic procedures, and products produced by recombinant techniques from a eukaryote host, including, for example, yeast, higher plant, insect and mammalian cells. Depending upon the host employed in a recombinant production procedure, the GLP-1 mimetibody or specified portion or variant of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

MIMETIBODIES, SPECIFIED FRAGMENTS AND/OR VARIANTS. The isolated mimetibodies of the present invention comprise a GLP-1 mimetibody or specified portion or variant encoded by any one of the polynucleotides of the present invention as discussed more fully herein, or any isolated or prepared GLP-1 mimetibody or specified portion or variant thereof.

Preferably, the GLP-1 mimetibody or ligand-binding portion or variant binds at least one GLP-1 protein ligand and thereby provides at least one GLP-1 biological activity of the corresponding protein or a fragment thereof. Different therapeutically or diagnostically significant proteins are well known in the art and suitable assays or biological activities of such proteins are also well known in the art.

Non-limiting examples of suitable GLP-1 peptides, variants and derivatives for this invention appear as SEQ ID NO: 1: His-Xaa2-Xaa3-Gly-Thr-Xaa6-Xaa7-Xaa8-Xaa9-Xaa10-

Ser-Xaa12-Tyr-Xaa14-Glu-Xaa16-Xaa17-Xaa18-Xaa19-Lys-Xaa21-Phe-Xaa23-Ala-Trp-Leu-Xaa27-Xaa28-Gly-Xaa30-Xaa31, wherein: Xaa2 is Ala, Gly, Ser, Thr, Leu, Ile, Val, Glu, Asp, or Lys; Xaa3 is Glu, Asp, or Lys; Xaa6 is Phe, His, Trp, or Tyr; Xaa7 is Thr or Asn; Xaa8 is Ser, Ala, Gly, Thr, Leu, Ile, Val, Glu, Asp, or Lys; Xaa9 is Asp or Glu; Xaa10 is Val, Gln, His, Glu, or Lys; Xaa12 is Ser, Val, Ala, Gly, Thr, Leu, Ile, Glu, Asp or Lys; Xaa14 is Leu, Gln, His, Glu, or Lys; Xaa16 is Gly, Ala, Ser, Thr, Leu, Ile, Val, Gln, Asn, Arg, Cys, Glu, Asp or Lys; Xaa17 is Gln, Asn, Arg, His, Glu, Asp or Lys; Xaa18 is Ala, Gly, Ser, Thr, Leu, Ile, Val, Glu, Asp or Lys; Xaa19 is Ala, Gly, Ser, Thr, Leu, Ile, Val, Glu, Asp or Lys; Xaa21 is Glu, Leu, Ala, His, Phe, Tyr, Trp, Arg, Gln, Thr, Ser, Gly, Asp or Lys; Xaa23 is Ile, Ala, Val, Leu or Glu; Xaa27 is Val, Gln, His, Glu, or Lys; Xaa28 is Lys, Asn, Arg, His, Glu or Asp; Xaa30 is Arg, His, Thr, Ser, Trp, Tyr, Phe, Glu, Asp or Lys; and Xaa31 is Gly, Ala, Ser, Thr, Leu, Ile, Val, Arg, Trp, Tyr, Phe, His, Glu, Asp, Lys or Pro.

Another preferred group of GLP-1 peptides, variants or derivatives are exemplified in SEQ ID NO:6: His-Xaa2-Xaa3-Gly-Xaa5-Xaa6-Xaa7-Xaa8-Xaa9-Xaa10-Ser-Xaa12-Xaa13-Xaa14-Glu-Xaa16-Xaa17-Xaa18-Xaa19-Lys-Xaa21-Phe-Xaa23-Xaa24-Trp-Leu-Xaa27-Xaa28-Gly-Xaa30, wherein: Xaa2 is Ala, Gly, or Ser; Xaa3 is Glu or Asp; Xaa5 is a variable amino acid; Xaa6 is His, Trp, Phe or Tyr; Xaa7 is Thr or Asn; Xaa8 is Ser, Thr or Ala; Xaa9 is Asp or Glu; Xaa10 is Val, Gln, His, Glu, or Lys; Xaa12 is Ser or Lys; Xaa13 is Tyr, Gln, His, Glu or Lys; Xaa14 is Leu, Gln, His, Glu, or Lys; Xaa16 is Gly, Ala, Glu or Asp; Xaa17 is Gln or Glu; Xaa18 is Ala or Lys; Xaa19 is Ala, Val, Ile, Leu or Met; Xaa21 is Glu or Leu; Xaa23 is Ile, Ala, Val, Leu or Glu; Xaa 24 is Ala, Gln, His, Glu, or Lys; Xaa27 is Val, Gln, His, Glu, or Lys; Xaa28 is Lys or Asn; and Xaa30 is Arg or Glu.

These peptides can be prepared by methods disclosed and/or known in the art. The Xaas in the sequence (and throughout this specification, unless specified otherwise in a particular instance) include specified amino acid residues, derivatives or modified amino acids thereof. Because the enzyme, dipeptidyl-peptidase IV (DPP-IV), may be responsible for the observed rapid in vivo inactivation of administered GLP-1, GLP-1 peptides, homologs, analogs and derivatives that are protected from the activity of DPP-IV in the context of mimetibody are preferred A GLP-1 mimetibody, or specified portion or variant thereof, that partially or preferably substantially provides at least one GLP-1 biological activity, can bind the GLP-1 ligand and thereby provide at least one activity that is otherwise mediated through the binding of GLP-1 to at least one ligand, such as a GLP-1 receptor, or through other protein-dependent or mediated mechanisms. As used herein, the term "GLP-1 mimetibody activity" refers to a GLP-1 mimetibody that can modulate or cause at least one GLP-1 dependent activity by about 20-10,000%, preferably by at least about 60, 70, 80, 90, 91, 92, 93, 94, 95, 96, 97, 98, 99, 100, 110, 120, 130, 140, 150, 160, 170, 180, 190, 200, 250, 300, 350, 400, 450, 500, 550, 600, 700, 800, 900, 1000, 2000, 3000, 4000, 5000, 6000, 7000, 8000, 9000% or more, depending on the assay.

The capacity of a GLP-1 mimetibody or specified portion or variant to provide at least one protein-dependent activity is preferably assessed by at least one suitable protein biological assay, as described herein and/or as known in the art. A human GLP-1 mimetibody or specified portion or variant of the invention can be similar to any class (IgG, IgA, IgM, etc.) or isotype and can comprise at least a portion of a kappa or lambda light chain. In one embodiment, the human GLP-1 mimetibody or specified portion or variant comprises IgG heavy chain variable fragments, hinge region, CH2 and CH3 of, at least one of isotypes, e.g., IgG1, IgG2, IgG3 or IgG4.

At least one GLP-1 mimetibody or specified portion or variant of the invention binds at least one ligand, subunit, fragment, portion or any combination thereof. The at least one GLP-1 peptide, variant or derivative of at least one GLP-1 mimetibody, specified portion or variant of the present invention can optionally bind at least one specified epitope of the ligand. The binding epitope can comprise any combination of at least one amino acid sequence of at least 1-3 amino acids to the entire specified portion of contiguous amino acids of the sequences of a protein ligand, such as a GLP-1 receptor or portion thereof.

Such mimetibodies can be prepared by joining together the various portions of Formula (I) of the GLP-1 mimetibody using known techniques, by preparing and expressing at least one nucleic acid molecules that encode the GLP-1 mimetibody, using known techniques of recombinant DNA technology or by using any other suitable method, such as chemical synthesis.

Mimetibodies that bind to human GLP-1 ligands, such as receptors, and that comprise a defined heavy or light chain variable region or portion thereof, can be prepared using suitable methods, such as phage display (Katsube, Y., et al., Int J. Mol. Med, 1(5):863-868 (1998)) or methods that employ transgenic animals, as known in the art. The GLP-1 mimetibody, specified portion or variant can be expressed using the encoding nucleic acid or portion thereof in a suitable host cell.

The invention also relates to mimetibodies, ligand-binding fragments and immunoglobulin chains comprising amino acids in a sequence that is substantially the same as an amino acid sequence described herein. Preferably, such mimetibodies or ligand-binding fragments thereof can bind human GLP-1 ligands, such as receptors, with high affinity (e.g., $K_D$ less than or equal to about $10^{-7}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes. The amino acids that make up mimetibodies or specified portions or variants of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994).

| SINGLE LETTER CODE | THREE LETTER CODE | NAME | THREE NUCL CODON(S) |
|---|---|---|---|
| A | Ala | Alanine | GCA, GCC, GCG, GCU |
| C | Cys | Cysteine | UGC, UGU |

-continued

| SINGLE LETTER CODE | THREE LETTER CODE | NAME | THREE NUCL CODON(S) |
|---|---|---|---|
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

A GLP-1 mimetibody or specified portion or variant of the present invention can include one or more amino acid substitutions, deletions or additions, either from natural mutations or human manipulation, as specified herein. Such or other sequences that can be used in the present invention, include, but are not limited to the following sequences presented in Table 1, as shown corresponding to specified portions of SEQ ID NOS:47-64, where the partial variable region of the antibody sequence can be, but is not limited to, at least one portion of at least one of SEQ ID NOS:47-55, or fragment thereof as described in Table 1, further optionally comprising at least one substitution, insertion or deletion as further described in FIGS. 1-9 of PCT publication WO 05/05604 (PCT US04/19898) filed Jun. 24, 2004 and published Jan. 20, 2005, with corresponding SEQ ID NOS: 1-9. The CH2, CH3 and hinge region can be, but not limited to, at least one portion of at least one of SEQ ID NOS:56-64, or fragment thereof as described in Table 1, further optionally comprising at least one substitution, insertion or deletion as further described in FIGS. 32-40 of PCT publication WO 05/05604 (PCT US04/19898) filed Jun. 24, 2004 and published Jan. 20, 2005, with corresponding SEQ ID NOS:32-40. Of course, the number of amino acid substitutions a skilled artisan would make depends on many factors, including those described above. Generally speaking, the number of amino acid substitutions, insertions or deletions for at least one of a GLP-1 mimetibody will not be more than 40, 30, 20,19, 18, 17, 16, 15, 14, 13, 12, 11, 10, 9, 8, 7, 6, 5, 4, 3, 2, 1 amino acids, such as 1-30 or any range or value therein, as specified herein.

In formula I of the present invention ((P(n)-L(o)-V(p)-H(q)-CH2(r)-CH3(s))(t), the V, H, CH2, CH3 portions according to Formula I can be any suitable human or human compatible sequence, e.g., as presented in Table 1, where the partial variable region of the antibody sequence can be, but is not limited to, at least one portion of at least one of SEQ ID NOS:47-55, or fragment thereof as described in Table 1, further optionally comprising at least one substitution, insertion or deletion as further described in FIGS. 1-9 of PCT publication WO 05/05604 (PCT US04/19898) filed Jun. 24, 2004 and published Jan. 20, 2005, with corresponding SEQ ID NOS:1-9; and where the CH2, CH3 and hinge region can be, but not limited to, at least one portion of at least one of SEQ ID NOS:56-64, or fragment thereof as described in Table 1, further optionally comprising at least one substitution, insertion or deletion as further described in FIGS. 32-40 of PCT publication WO 05/05604 (PCT US04/19898) filed Jun. 24, 2004 and published Jan. 20, 2005, with corresponding SEQ ID NOS:32-40, or as known in the art, or any combination or consensus sequence thereof, or any fusion protein thereof, preferably of human origin or engineered to minimize immunogenicity when administered to humans.

The P portion can comprise at least one GLP-1 therapeutic peptide known in the art or described herein, such as, but not limited to those presented in SEQ ID NO: 1, or any combination or consensus sequence thereof, or any fusion protein thereof. In a preferred embodiment, the P portion can comprise at least one GLP-1 peptide having the sequence of at least one of SEQ ID NO:6, or any combination or consensus sequence thereof, or any fusion protein thereof.

The optional linker sequence can be any suitable peptide linker as known in the art. Preferred sequences include any combination of G and S, e.g., X1-X2-X3-X4-...-Xn, where X can be G or S, and n can be 5-30. Non-limiting examples include GS, GGS, GGGS (SEQ ID NO:16), GSGGGS (SEQ ID NO: 17), GGSGGGS (SEQ ID NO:18), GGSGGGSGG (SEQ ID NO: 19) and GGGSGGGSGG (SEQ ID NO:20); and the like.

Amino acids in a GLP-1 mimetibody or specified portion or variant of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least one protein related activity, as specified herein or as known in the art. Sites that are critical for GLP-1 mimetibody or specified portion or variant binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

Mimetibodies or specified portions or variants of the present invention can comprise as the P portion of Formula (I), e.g. but not limited to, at least one portion of at least one of SEQ ID NOS: 1 and 6. A GLP-1 mimetibody or specified portion or variant can further optionally comprise at least one functional portion of at least one polypeptide as P portion of Formula (I), at least 90-100% of at least on of SEQ ID NOS: 1 and 6. Non-limiting variants that can enhance or maintain at least one of the listed activities above include, but are not limited to, any of the above polypeptides, further comprising at least one mutation corresponding to at least one substitution, insertion or deletion that does not significantly affect the suitable biological activities or functions of said GLP-1 mimetibody.

In one embodiment, the P amino acid sequence, or portion thereof, has about 90-100% identity (i.e., 90, 91, 92, 93, 94, 95, 96, 97, 98, 99, 100 or any range or value therein) to the corresponding amino acid sequence of the corresponding portion of at least one of SEQ ID NOS:1 and 6. Preferably, 90-100% amino acid identity (i.e., 90, 91, 92, 93, 94, 95, 96, 97, 98, 99, 100 or any range or value therein) is determined using a suitable computer algorithm, as known in the art.

Mimetibodies or specified portions or variants of the present invention can comprise any number of contiguous amino acid residues from a GLP-1 mimetibody or specified portion or variant of the present invention, wherein that number is selected from the group of integers consisting of from 10-100% of the number of contiguous residues in a GLP-1 mimetibody. Optionally, this subsequence of contiguous amino acids is at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, 5, 6, 7, 8, 9, 10, 11, 12, 13, 14, 15, 16, 17, 18, 19, 20, or more.

As those of skill will appreciate, the present invention includes at least one biologically active GLP-1 mimetibody or specified portion or variant of the present invention. Biologically active mimetibodies or specified portions or variants have a specific activity at least 20%, 30%, or 40%, and preferably at least 50%, 60%, or 70%, and most preferably at least 80%, 90%, or 95%-1000% of that of the native (non-synthetic), endogenous or related and known inserted or fused protein or specified portion or variant. Methods of assaying and quantifying measures of enzymatic activity and substrate specificity are well known to those of skill in the art.

In another aspect, the invention relates to human mimetibodies and ligand-binding fragments, as described herein, which are modified by the covalent attachment of an organic moiety. Such modification can produce a GLP-1 mimetibody or ligand-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified mimetibodies and ligand-binding fragments of the invention can comprise one or more organic moieties that are covalently bonded, directly or indirectly, to the GLP-1 mimetibody or specified portion or variant. Each organic moiety that is bonded to a GLP-1 mimetibody or ligand-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, a GLP-1 mimetibody modified by the covalent attachment of polylysine is encompassed by the invention. Hydrophilic polymers suitable for modifying mimetibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the GLP-1 mimetibody of the invention has a molecular weight of about 800 to about 150,000 Daltons as a separate molecular entity. For example, $PEG_{2500}$, $PEG_{5000}$, $PEG_{7500}$, $PEG_{9000}$, $PEG_{1000}$, $PEG_{12500}$, $PEG_{15000}$, and $PEG_{20,000}$, wherein the subscript is the average molecular weight of the polymer in Daltons, can be used.

The hydrophilic polymeric group can be substituted with one to about six alkyl, fatty acid or fatty acid ester groups.

Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying mimetibodies of the invention can be saturated or can contain one or more units of unsaturation. Fatty acids that are suitable for modifying mimetibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-Δ9-octadecanoate ($C_{18}$, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include monoesters of dicarboxylic acids that comprise a linear or branched lower alkyl group. The lower alkyl group can comprise from one to about twelve, preferably one to about six, carbon atoms.

The modified human mimetibodies and ligand-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl)carbodimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified mimetibodies of the invention can be produced by reacting an human GLP-1 mimetibody or ligand-binding fragment with a modifying agent. For example, the organic moieties can be bonded to the GLP-1 mimetibody in a non-site specific manner by employing an amine-reactive modifying agent, for example, an NHS ester of PEG. Modified human mimetibodies or ligand-binding fragments can also be prepared by reducing disulfide bonds (e.g., intra-chain disulfide bonds) of a GLP-1 mimetibody or ligand-binding fragment. The reduced GLP-1 mimetibody or ligand-binding fragment can then be reacted with a thiol-reactive modifying agent to produce the modified GLP-1 mimetibody of the invention. Modified human mimetibodies and ligand-binding fragments comprising an organic moiety that is bonded to specific sites of a GLP-1 mimetibody or specified portion or variant of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10): 2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, Calif. (1996).

GLP-1 MIMETIBODY COMPOSITIONS. The present invention also provides at least one GLP-1 mimetibody or specified portion or variant composition comprising at least one, at least two, at least three, at least four, at least five, at least six or more mimetibodies or specified portions or variants thereof, as described herein and/or as known in the art that are provided in a non-naturally occurring composition, mixture or form. Such composition percentages are by weight, volume, concentration, molarity, or molality as liquid or dry solutions, mixtures, suspension, emulsions or colloids, as known in the art or as described herein.

Such compositions can comprise 0.00001-99.9999 percent by weight, volume, concentration, molarity, or molality as liquid, gas, or dry solutions, mixtures, suspension, emulsions or colloids, as known in the art or as described herein, on any range or value therein, such as but not limited to 0.00001, 0.00003, 0.00005, 0.00009, 0.0001, 0.0003, 0.0005, 0.0009, 0.001, 0.003, 0.005, 0.009, 0.01, 0.02, 0.03, 0.05, 0.09, 0.1, 0.2, 0.3, 0.4., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, 5, 6, 7, 8, 9, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9%. Such compositions of the present invention thus include but are not limited to 0.00001-100 mg/ml and/or 0.00001-100 mg/g.

The composition can optionally further comprise an effective amount of at least one compound or protein selected from at least one of a diabetes or insuling metabolism related drug, an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see e.g., Nursing 2001 Handbook of Drugs, 21$^{st}$ edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

The diabetes related drug can be at least one of glitazones, insulin and derivatives, sulfonylureas, meglitinides, biguanides, alpha-glucosidase inhibitors, protein tyrosine phosphastase-1B, glycogen synthase kinase 3, gluconeogenesis inhibitors, pyruvate dehydrogenase kinase (PDH) inhibitors, lipolysis inhibitors, fat oxidation inhibitors, carnitine palmitoyltransferase I and/or II inhibitors, beta-3 adrenoceptor agonists, sodium and glucose cotransporter (SGLT) inhibitors, or compounds that act on one or more of at least one of: autoimmune suppression, immune regulation, activation, proliferation, migration and/or suppressor cell function of T-cells, inhibition of T cell receptor/peptide/MHC-II interaction, Induction of T cell anergy, deletion of autoreactive T cells, reduction of trafficking across blood brain barrier, alteration of balance of pro-inflammatory (Th1) and immunomodulatory (Th2) cytokines, inhibition of matrix metalloprotease inhibitors, neuroprotection, reduction of gliosis, promotion of re-myelination.

The anti-infective drug can be at least one selected from amebicides or antiprotozoals, anthelmintics, antifungals, antimalarials, antituberculotics or antileprotics, aminoglycosides, penicillins, cephalosporins, tetracyclines, sulfonamides, fluoroquinolones, antivirals, macrolide anti-infectives and miscellaneous anti-infectives. The CV drug can be at least one selected from inotropics, antiarrhythmics, antianginals, antihypertensives, antilipemics and miscellaneous cardiovascular drugs. The CNS drug can be at least one selected from nonnarcotic analgesics or at least one selected from antipyretics, nonsteroidal anti-inflammatory drugs, narcotic or opiod analgesics, sedative-hypnotics, anticonvulsants, antidepressants, antianxiety drugs, antipsychotics, central nervous system stimulants, antiparkinsonians and miscellaneous central nervous system drugs. The ANS drug can be at least one selected from cholinergics (parasympathomimetics), anticholinergics, adrenergics (sympathomimetics), adrenergic blockers (sympatholytics), skeletal muscle relaxants and neuromuscular blockers. The respiratory tract drug can be at least one selected from antihistamines, bronchodilators, expectorants or antitussives and miscellaneous respiratory drugs. The GI tract drug can be at least one selected from antacids, adsorbents, antiflatulents, digestive enzymes, gallstone solubilizers, antidiarrheals, laxatives, antiemetics and antiulcer drugs. The hormonal drug can be at least one selected from corticosteroids, androgens, anabolic steroids, estrogens, progestins, gonadotropins, antidiabetic drugs, at least one glucagon, thyroid hormones, thyroid hormone antagonists, pituitary hormones and parathyroid-like drugs. The drug for fluid and electrolyte balance can be at least one selected from diuretics, electrolytes, replacement solutions, acidifiers and alkalinizers. The hematologic drug can be at least one selected from hematinics, anticoagulants, blood derivatives and thrombolytic enzymes. The antineoplastics can be at least one selected from alkylating drugs, antimetabolites, antibiotic antineoplastics, antineoplastics that alter hormone balance and miscellaneous antineoplastics. The immunomodulation drug can be at least one selected from immunosuppressants, vaccines, toxoids, antitoxins, antivenins, immune serums and biological response modifiers. The ophthalmic, otic, and nasal drugs can be at least one selected from ophthalmic anti-infectives, ophthalmic anti-inflammatories, miotics, mydriatics, ophthalmic vasoconstrictors and miscellaneous ophthalmics, otics, nasal drugs.

The topical drug can be at least one selected from local anti-infectives, scabicides, pediculicides and topical corticosteroids. The nutritional drug can be at least one selected from vitamins, minerals and calorics. See, e.g., contents of *Nursing* 2001 *Drug Handbook*, supra.

The at least one amebicide or antiprotozoal can be at least one selected from atovaquone, chloroquine hydrochloride, chloroquine phosphate, metronidazole, metronidazole hydrochloride and pentamidine isethionate. The at least one anthelmintic can be at least one selected from mebendazole, pyrantel pamoate and thiabendazole. The at least one antifungal can be at least one selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin and terbinafine hydrochloride. The at least one antimalarial can be at least one selected from chloroquine hydrochloride, chloroquine phosphate, doxycycline, hydroxychloroquine sulfate, mefloquine hydrochloride, primaquine phosphate, pyrimethamine and pyrimethamine with sulfadoxine. The at least one antituberculotic or antileprotic can be at least one selected from clofazimine, cycloserine, dapsone, ethambutol hydrochloride, isoniazid, pyrazinamide, rifabutin, rifampin, rifapentine and streptomycin sulfate. The at least one aminoglycoside can be at least one selected from amikacin sulfate, gentamicin sulfate, neomycin sulfate, streptomycin sulfate and tobramycin sulfate. The at least one penicillin can be at least one selected from amoxcillin/clavulanate potassium, amoxicillin trihydrate, ampicillin, ampicillin sodium, ampicillin trihydrate, ampicillin sodium/sulbactam sodium, cloxacillin sodium, dicloxacillin sodium, mezlocillin sodium, nafcillin sodium, oxacillin sodium, penicillin G benzathine, penicillin G potassium, penicillin G procaine, penicillin G sodium, penicillin V potassium, piperacillin sodium, piperacillin sodium/tazobactam sodium, ticarcillin disodium and ticarcillin disodium/clavulanate potassium. The at least one cephalosporin can be at least one selected from at least one of cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, loracarbef. The at least one tetracycline can be at least one selected from demeclocycline hydrochloride, doxycycline calcium, doxycycline hyclate, doxycycline hydrochloride, doxycycline monohydrate, minocycline hydrochloride, tetracycline hydrochloride. The at least one sulfonamide can be at least one selected from co-trimoxazole, sulfadiazine, sulfamethoxazole, sulfisoxazole, sulfisoxazole acetyl. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, trovafloxacin mesylate. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, trovafloxacin mesylate. The at least one antiviral can be at least one selected from abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, zidovudine. The at least one macroline anti-infective can be at least one selected from azithromycin, clarithromycin, dirithromycin, erythromycin base, erythromycin estolate, erythromycin ethylsuccinate, erythromycin lactobionate, erythromycin stearate. The at least one miscellaneous anti-infective can be at least one selected from aztreonam, bacitracin, chloramphenicol sodium sucinate, clindamycin hydrochloride, clindamycin palmitate hydrochloride, clindamycin phosphate, imipenem and cilastatin sodium, meropenem, nitrofurantoin macrocrystals, nitrofurantoin microcrystals, quinupristin/dalfopristin, spectinomycin hydrochloride, trimethoprim, vancomycin hydrochloride. (See, e.g., pp. 24-214 of *Nursing* 2001 *Drug Handbook*.)

The at least one inotropic can be at least one selected from amrinone lactate, digoxin, milrinone lactate. The at least one antiarrhythmic can be at least one selected from adenosine, amiodarone hydrochloride, atropine sulfate, bretylium tosylate, diltiazem hydrochloride, disopyramide, disopyramide phosphate, esmolol hydrochloride, flecainide acetate, ibutilide fumarate, lidocaine hydrochloride, mexiletine hydrochloride, moricizine hydrochloride, phenytoin, phenytoin sodium, procainamide hydrochloride, propafenone hydrochloride, propranolol hydrochloride, quinidine bisulfate, quinidine gluconate, quinidine polygalacturonate, quinidine sulfate, sotalol, tocainide hydrochloride, verapamil hydrochloride. The at least one antianginal can be at least one selected from amlodipidine besylate, amyl nitrite, bepridil hydrochloride, diltiazem hydrochloride, isosorbide dinitrate, isosorbide mononitrate, nadolol, nicardipine hydrochloride, nifedipine, nitroglycerin, propranolol hydrochloride, verapamil, verapamil hydrochloride. The at least one antihypertensive can be at least one selected from acebutolol hydrochloride, amlodipine besylate, atenolol, benazepril hydrochloride, betaxolol hydrochloride, bisoprolol fumarate, candesartan cilexetil, captopril, carteolol hydrochloride, carvedilol, clonidine, clonidine hydrochloride, diazoxide, diltiazem hydrochloride, doxazosin mesylate, enalaprilat, enalapril maleate, eprosartan mesylate, felodipine, fenoldopam mesylate, fosinopril sodium, guanabenz acetate, guanadrel sulfate, guanfacine hydrochloride, hydralazine hydrochloride, irbesartan, isradipine, labetalol hydrchloride, lisinopril, losartan potassium, methyldopa, methyldopate hydrochloride, metoprolol succinate, metoprolol tartrate, minoxidil, moexipril hydrochloride, nadolol, nicardipine hydrochloride, nifedipine, nisoldipine, nitroprusside sodium, penbutolol sulfate, perindopril erbumine, phentolamine mesylate, pindolol, prazosin hydrochloride, propranolol hydrochloride, quinapril hydrochloride, ramipril, telmisartan, terazosin hydrochloride, timolol maleate, trandolapril, valsartan, verapamil hydrochloride The at least one antilipemic can be at least one selected from atorvastatin calcium, cerivastatin sodium, cholestyramine, colestipol hydrochloride, fenofibrate (micronized), fluvastatin sodium, gemfibrozil, lovastatin, niacin, pravastatin sodium, simvastatin. The at least one miscellaneous CV drug can be at least one selected from abciximab, alprostadil, arbutamine hydrochloride, cilostazol, clopidogrel bisulfate, dipyridamole, eptifibatide, midodrine hydrochloride, pentoxifylline, ticlopidine hydrochloride, tirofiban hydrochloride. (See, e.g., pp. 215-336 of *Nursing* 2001 *Drug Handbook*.)

The at least one nonnarcotic analgesic or antipyretic can be at least one selected from acetaminophen, aspirin, choline magnesium trisalicylate, diflunisal, magnesium salicylate. The at least one nonsteroidal anti-inflammatory drug can be at least one selected from celecoxib, diclofenac potassium, diclofenac sodium, etodolac, fenoprofen calcium, flurbiprofen, ibuprofen, indomethacin, indomethacin sodium trihydrate, ketoprofen, ketorolac tromethamine, nabumetone, naproxen, naproxen sodium, oxaprozin, piroxicam, rofecoxib, sulindac. The at least one narcotic or opiod analgesic can be at least one selected from alfentanil hydrochloride, buprenorphine hydrochloride, butorphanol tartrate, codeine phosphate, codeine sulfate, fentanyl citrate, fentanyl transdermal system, fentanyl transmucosal, hydromorphone hydrochloride, meperidine hydrochloride, methadone hydrochloride, morphine hydrochloride, morphine sulfate, morphine tartrate, nalbuphine hydrochloride, oxycodone hydrochloride, oxycodone pectinate, oxymorphone hydrochloride, pentazocine hydrochloride, pentazocine hydrochloride and naloxone hydrochloride, pentazocine lactate, propoxyphene hydrochloride, propoxyphene napsylate, remifentanil hydrochloride, sufentanil citrate, tramadol hydrochloride. The at least one sedative-hypnotic can be at least one selected from chloral hydrate, estazolam, flurazepam hydrochloride, pentobarbital, pentobarbital sodium, phenobarbital sodium, secobarbital sodium, temazepam, triazolam, zaleplon, zolpidem tartrate. The at least one anticonvulsant can be at least one selected from acetazolamide sodium, carbamazepine, clonazepam, clorazepate dipotassium, diazepam, divalproex sodium, ethosuximde, fosphenytoin sodium, gabapentin, lamotrigine, magnesium sulfate, phenobarbital, phenobarbital sodium, phenytoin, phenytoin sodium, phenytoin sodium (extended), primidone, tiagabine hydrochloride, topiramate, valproate sodium, valproic acid. The at least one antidepressant can be at least one selected from amitriptyline hydrochloride, amitriptyline pamoate, amoxapine, bupropion hydrochloride, citalopram hydrobromide, clomipramine hydrochloride, desipramine hydrochloride, doxepin hydrochloride, fluoxetine hydrochloride, imipramine hydrochloride, imipramine pamoate, mirtazapine, nefazodone hydrochloride, nortriptyline hydrochloride, paroxetine hydrochloride, phenelzine sulfate, sertraline hydrochloride, tranylcypromine sulfate, trimipramine maleate, venlafaxine hydrochloride. The at least one antianxiety drug can be at least one selected from alprazolam, buspirone hydrochloride, chlordiazGLP-1 xide, chlordiazGLP-1 xide hydrochloride, clorazepate dipotassium, diazepam, doxepin hydrochloride, hydroxyzine embonate, hydroxyzine hydrochloride, hydroxyzine pamoate, lorazepam, mephrobamate, midazolam hydrochloride, oxazepam. The at least one antipsychotic drug can be at least one selected from chlorpromazine hydrochloride, clozapine, fluphenazine decanoate, fluephenazine enanthate, fluphenazine hydrochloride, haloperidol, haloperidol decanoate, haloperidol lactate, loxapine hydrochloride, loxapine succinate, mesoridazine besylate, molindone hydrochloride, olanzapine, perphenazine, pimozide, prochlorperazine, quetiapine fumarate, risperidone, thioridazine hydrochloride, thiothixene, thiothixene hydrochloride, trifluoperazine hydrochloride. The at least one central nervous system stimulant can be at least one selected from amphetamine sulfate, caffeine, dextroamphetamine sulfate, doxapram hydrochloride, methamphetamine hydrochloride, methylphenidate hydrochloride, modafinil, pemoline, phentermine hydrochloride. The at least one antiparkinsonian can be at least one selected from amantadine hydrochloride, benztropine mesylate, biperiden hydrochloride, biperiden lactate, bromocriptine mesylate, carbidopa-levodopa, entacapone, levodopa, pergolide mesylate, pramipexole dihydrochloride, ropinirole hydrochloride, selegiline hydrochloride, tolcapone, trihexyphenidyl hydrochloride. The at least one miscellaneous central nervous system drug can be at least one selected from bupropion hydrochloride, donepezil hydrochloride, droperidol, fluvoxamine maleate, lithium carbonate, lithium citrate, naratriptan hydrochloride, nicotine polacrilex, nicotine transdermal system, propofol, rizatriptan benzoate, sibutramine hydrochloride monohydrate, sumatriptan succinate, tacrine hydrochloride, zolmitriptan. (See, e.g., pp. 337-530 of Nursing 2001 Drug Handbook.)

The at least one cholinergic (e.g., parasymathomimetic) can be at least one selected from bethanechol chloride, edrophonium chloride, neostigmine bromide, neostigmine methylsulfate, physostigmine salicylate, pyridostigmine bromide. The at least one anticholinergics can be at least one selected from atropine sulfate, dicyclomine hydrochloride, glycopyrrolate, hyoscyamine, hyoscyamine sulfate, propantheline bromide, scopolamine, scopolamine butylbromide, scopolamine hydrobromide. The at least one adrenergics (sympathomimetics) can be at least one selected from dobutamine hydrochloride, dopamine hydrochloride, metaraminol bitartrate, norepinephrine bitartrate, phenylephrine hydrochloride, pseudoephedrine hydrochloride, pseudoephedrine sulfate. The at least one adrenergic blocker (sympatholytic) can be at least one selected from dihydroergotamine mesylate, ergotamine tartrate, methysergide maleate, propranolol hydrochloride. The at least one skeletal muscle relaxant can be at least one selected from baclofen, carisoprodol, chlorzoxazone, cyclobenzaprine hydrochloride, dantrolene sodium, methocarbamol, tizanidine hydrochloride. The at least one neuromuscular blockers can be at least one selected from atracurium besylate, cisatracurium besylate, doxacurium chloride, mivacurium chloride, pancuronium bromide, pipecuronium bromide, rapacuronium bromide, rocuronium bromide, succinylcholine chloride, tubocurarine chloride, vecuronium bromide. (See, e.g., pp. 531-84 of Nursing 2001 Drug Handbook.)

The at least one antihistamine can be at least one selected from brompheniramine maleate, cetirizine hydrochloride, chlorpheniramine maleate, clemastine fumarate, cyproheptadine hydrochloride, diphenhydramine hydrochloride, fexofenadine hydrochloride, loratadine, promethazine hydrochloride, promethazine theoclate, triprolidine hydrochloride. The at least one bronchodilators can be at least one selected from albuterol, albuterol sulfate, aminophylline, atropine sulfate, ephedrine sulfate, epinephrine, epinephrine bitartrate, epinephrine hydrochloride, ipratropium bromide, isoproterenol, isoproterenol hydrochloride, isoproterenol sulfate, levalbuterol hydrochloride, metaproterenol sulfate, oxtriphylline, pirbuterol acetate, salmeterol xinafoate, terbutaline sulfate, theophylline. The at least one expectorants or antitussives can be at least one selected from benzonatate, codeine phosphate, codeine sulfate, dextramethorphan hydrobromide, diphenhydramine hydrochloride, guaifenesin, hydromorphone hydrochloride. The at least one miscellaneous respiratory drug can be at least one selected from acetylcysteine, beclomethasone dipropionate, beractant, budesonide, calfactant, cromolyn sodium, dornase alfa, GLP-1 prostenol sodium, flunisolide, fluticasone propionate, montelukast sodium, nedocromil sodium, palivizumab, triamcinolone acetonide, zafirlukast, zileuton. (See, e.g., pp. 585-642 of Nursing 2001 Drug Handbook.)

The at least one antacid, adsorbents, or antiflatulents can be at least one selected from aluminum carbonate, aluminum hydroxide, calcium carbonate, magaldrate, magnesium hydroxide, magnesium oxide, simethicone, and sodium bicarbonate. The at least one digestive enymes or gallstone solubilizers can be at least one selected from pancreatin, pancrelipase, and ursodiol. The at least one antidiarrheal can be at least one selected from attapulgite, bismuth subsalicylate, calcium polycarbophil, diphenoxylate hydrochloride or atropine sulfate, loperamide, octreotide acetate, opium tincture, opium tincure (camphorated). The at least one laxative can be at least one selected from bisocodyl, calcium polycarbophil, cascara sagrada, cascara sagrada aromatic fluidextract, cascara sagrada fluidextract, castor oil, docusate calcium, docusate sodium, glycerin, lactulose, magnesium citrate, magnesium hydroxide, magnesium sulfate, methylcellulose, mineral oil, polyethylene glycol or electrolyte solution, psyllium, senna, sodium phosphates. The at least one antiemetic can be at least one selected from chlorpromazine hydrochloride, dimenhydrinate, dolasetron mesylate, dronabinol, granisetron hydrochloride, meclizine hydrochloride, metocloproamide hydrochloride, ondansetron hydrochloride, perphenazine, prochlorperazine, prochlorperazine edisylate, prochlorperazine maleate, promethazine hydrochloride, scopolamine, thiethylperazine maleate, trimethobenzamide hydrochloride. The at least one antiulcer drug can be at least one selected from cimetidine, cimetidine hydrochloride, famotidine, lansoprazole, misoprostol, nizatidine, omeprazole, rabeprozole sodium, rantidine bismuth citrate, ranitidine hydrochloride, sucralfate. (See, e.g., pp. 643-95 of *Nursing* 2001 *Drug Handbook.*) The at least one coricosteroids can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, triamcinolone diacetate. The at least one androgen or anabolic steroids can be at least one selected from danazol, fluoxymesterone, methyltestosterone, nandrolone decanoate, nandrolone phenpropionate, testosterone, testosterone cypionate, testosterone enanthate, testosterone propionate, testosterone transdermal system. The at least one estrogen or progestin can be at least one selected from esterified estrogens, estradiol, estradiol cypionate, estradiol/norethindrone acetate transdermal system, estradiol valerate, estrogens (conjugated), estropipate, ethinyl estradiol, ethinyl estradiol and desogestrel, ethinyl estradiol and ethynodiol diacetate, ethinyl estradiol and desogestrel, ethinyl estradiol and ethynodiol diacetate, ethinyl estradiol and levonorgestrel, ethinyl estradiol and norethindrone, ethinyl estradiol and norethindrone acetate, ethinyl estradiol and norgestimate, ethinyl estradiol and norgestrel, ethinyl estradiol and norethindrone and acetate and ferrous fumarate, levonorgestrel, medroxyprogesterone acetate, mestranol and norethindron, norethindrone, norethindrone acetate, norgestrel, progesterone. The at least one gonadroptropin can be at least one selected from ganirelix acetate, gonadoreline acetate, histrelin acetate, menotropins. The at least one antidiabetic or glucaon can be at least one selected from acarbose, chlorpropamide, glimepiride, glipizide, glucagon, glyburide, insulins, metformin hydrochloride, miglitol, pioglitazone hydrochloride, repaglinide, rosiglitazone maleate, troglitazone. The at least one thyroid hormone can be at least one selected from levothyroxine sodium, liothyronine sodium, liotrix, thyroid. The at least one thyroid hormone antagonist can be at least one selected from methimazole, potassium iodide, potassium iodide (saturated solution), propylthiouracil, radioactive iodine (sodium iodide $^{131}$I), strong iodine solution. The at least one pituitary hormone can be at least one selected from corticotropin, cosyntropin, desmophressin acetate, leuprolide acetate, rGLP-1sitory corticotropin, somatrem, somatropin, vasopressin. The at least one parathyroid-like drug can be at least one selected from calcifediol, calcitonin (human), calcitonin (salmon), calcitriol, dihydrotachysterol, etidronate disodium. (See, e.g., pp. 696-796 of *Nursing* 2001 *Drug Handbook.*)

The at least one diuretic can be at least one selected from acetazolamide, acetazolamide sodium, amiloride hydrochloride, bumetanide, chlorthalidone, ethacrynate sodium, ethacrynic acid, furosemide, hydrochlorothiazide, indapamide, mannitol, metolazone, spironolactone, torsemide, triamterene, urea. The at least one electrolyte or replacement solution can be at least one selected from calcium acetate, calcium carbonate, calcium chloride, calcium citrate, calcium glubionate, calcium gluceptate, calcium gluconate, calcium lactate, calcium phosphate (dibasic), calcium phosphate (tribasic), dextran (high-molecular-weight), dextran (low-molecular-weight), hetastarch, magnesium chloride, magnesium sulfate, potassium acetate, potassium bicarbonate, potassium chloride, potassium gluconate, Ringer's injection, Ringer's injection (lactated), sodium chloride. The at least one acidifier or alkalinizer can be at least one selected from sodium bicarbonate, sodium lactate, tromethamine. (See, e.g., pp. 797-833 of *Nursing* 2001 *Drug Handbook.*)

The at least one hematinic can be at least one selected from ferrous fumarate, ferrous gluconate, ferrous sulfate, ferrous sulfate (dried), iron dextran, iron sorbitol, polysaccharide-iron complex, sodium ferric gluconate complex. The at least one anticoagulant can be at least one selected from ardeparin sodium, dalteparin sodium, danaparoid sodium, enoxaparin sodium, heparin calcium, heparin sodium, warfarin sodium. The at least one blood derivative can be at least one selected from albumin 5%, albumin 25%, antihemophilic factor, anti-inhibitor coagulant complex, antithrombin m (human), factor IX (human), factor IX complex, plasma protein fractions. The at least one thrombolytic enzyme can be at least one selected from alteplase, anistreplase, reteplase (recombinant), streptokinase, urokinase. (See, e.g., pp. 834-66 of *Nursing* 2001 *Drug Handbook.*)

The at least one alkylating drug can be at least one selected from busulfan, carboplatin, carmustine, chlorambucil, cisplatin, cyclophosphamide, ifosfamide, lomustine, mechlorethamine hydrochloride, melphalan, melphalan hydrochloride, streptozocin, temozolomide, thiotepa. The at least one antimetabolite can be at least one selected from capecitabine, cladribine, cytarabine, floxuridine, fludarabine phosphate, fluorouracil, hydroxyurea, mercaptopurine, methotrexate, methotrexate sodium, thioguanine. The at least one antibiotic antineoplastic can be at least one selected from bleomycin sulfate, dactinomycin, daunorubicin citrate liposomal, daunorubicin hydrochloride, doxorubicin hydrochloride, doxorubicin hydrochloride liposomal, epirubicin hydrochloride, idarubicin hydrochloride, mitomycin, pentostatin, plicamycin, valrubicin. The at least one antineoplastics that alter hormone balance can be at least one selected from anastrozole, bicalutamide, estramustine phosphate sodium, exemestane, flutamide, goserelin acetate, letrozole, leuprolide acetate, megestrol acetate, nilutamide, tamoxifen citrate, testolactone, toremifene citrate. The at least one miscellaneous antineoplastic can be at least one selected from asparaginase, bacillus Calmette-Guerin (BCG) (live intravesical), dacarbazine, docetaxel, etoposide, etoposide phosphate, gemcitabine hydrochloride, irinotecan hydrochloride, mitotane, mitoxantrone hydrochloride, paclitaxel, pegaspargase, porfimer sodium, procarbazine hydrochloride, rituximab, teniposide, topotecan hydrochloride, trastuzumab, tretinoin, vinblastine sulfate, vincristine sulfate, vinorelbine tartrate. (See, e.g., pp. 867-963 of *Nursing* 2001 *Drug Handbook.*)

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, tacrolimus. The at least one vaccine or toxoid can be at least one selected from BCG vaccine, cholera vaccine, diphtheria and tetanus toxoids (adsorbed), diphtheria and tetanus toxoids and acellular pertussis vaccine adsorbed, diphtheria and tetanus toxoids and whole-cell pertussis vaccine, Haemophilius b conjugate vaccines, hepatitis A vaccine (inactivated), hepatisis B vaccine (recombinant), influenza virus vaccine 1999-2000 trivalent types A & B (purified surface antigen), influenza virus vaccine 1999-2000 trivalent types A & B (subvirion or purified subvirion), influenza virus vaccine 1999-2000 trivalent types A & B (whole virion), Japanese encephalitis virus vaccine (inactivated), Lyme disease vaccine (recombinant OspA), measles and mumps and rubella virus vaccine (live), measles and mumps and rubella virus vaccine (live attenuated), measles virus vaccine (live attenuated), meningococcal polysaccharide vaccine, mumps virus vaccine (live), plague vaccine, pneumococcal vaccine (polyvalent), poliovirus vaccine (inactivated), poliovirus vaccine (live, oral, trivalent), rabies vaccine (adsorbed), rabies vaccine (human diploid cell), rubella and mumps virus vaccine (live), rubella virus vaccine (live, attenuated), tetanus toxoid (adsorbed), tetanus toxoid (fluid), typhoid vaccine (oral), typhoid vaccine (parenteral), typhoid Vi polysaccharide vaccine, varicella virus vaccine, yellow fever vaccine. The at least one antitoxin or antivenin can be at least one selected from black widow spider antivenin, Crotalidae antivenom (polyvalent), diphtheria antitoxin (equine), *Micrurus fulvius* antivenin). The at least one immune serum can be at least one selected from cytomegalovirus immune globulin (intraveneous), hepatitis B immune globulin (human), immune globulin intramuscular, immune globulin intravenous, rabies immune globulin (human), respiratory syncytial virus immune globulin intravenous (human), $Rh_0(D)$ immune globulin (human), $Rh_0(D)$ immune globulin intravenous (human), tetanus immune globulin (human), varicella-zoster immune globulin. The at least one biological response modifiers can be at least one selected from aldesleukin, GLP-1 etin alfa, filgrastim, glatiramer acetate for injection, interferon alfacon-1, interferon alfa-2a (recombinant), interferon alfa-2b (recombinant), interferon beta-la, interferon beta-1b (recombinant), interferon gamma-1b, levamisole hydrochloride, oprelvekin, sargramostim. (See, e.g., pp. 964-1040 of *Nursing* 2001 *Drug Handbook.*)

The at least one ophthalmic anti-infectives can be selected form bacitracin, chloramphenicol, ciprofloxacin hydrochloride, erythromycin, gentamicin sulfate, ofloxacin 0.3%, polymyxin B sulfate, sulfacetamide sodium 10%, sulfacetamide sodium 15%, sulfacetamide sodium 30%, tobramycin, vidarabine. The at least one ophthalmic anti-inflammatories can be at least one selected from dexamethasone, dexamethasone sodium phosphate, diclofenac sodium 0.1%, fluorometholone, flurbiprofen sodium, ketorolac tromethamine, prednisolone acetate (suspension) prednisolone sodium phosphate (solution). The at least one miotic can be at least one selected from acetylocholine chloride, carbachol (intraocular), carbachol (topical), echothiophate iodide, pilocarpine, pilocarpine hydrochloride, pilocarpine nitrate. The at least one mydriatic can be at least one selected from atropine sulfate, cyclopentolate hydrochloride, epinephrine hydrochloride, epinephryl borate, homatropine hydrobromide, phenylephrine hydrochloride, scopolamine hydrobromide, tropicamide. The at least one ophthalmic vasoconstrictors can be at least one selected from naphazoline hydrochloride, oxymetazoline hydrochloride, tetrahydrozoline hydrochloride. The at least one miscellaneous ophthalmics can be at least one selected from apraclonidine hydrochloride, betaxolol hydrochloride, brimonidine tartrate, carteolol hydrochloride, dipivefrin hydrochloride, dorzolamide hydrochloride, emedastine difumarate, fluorescein sodium, ketotifen fumarate, latanoprost, levobunolol hydrochloride, metipranolol hydrochloride, sodium chloride (hypertonic), timolol maleate. The at least one otic can be at least one selected from boric acid, carbamide peroxide, chloramphenicol, triethanolamine polypeptide oleate-condensate. The at least one nasal drug can be at least one selected from beclomethasone dipropionate, budesonide, ephedrine sulfate, epinephrine hydrochloride, flunisolide, fluticasone propionate, naphazoline hydrochloride, oxymetazoline hydrochloride, phenylephrine hydrochloride, tetrahydrozoline hydrochloride, triamcinolone acetonide, xylometazoline hydrochloride. (See, e.g., pp. 1041-97 of *Nursing* 2001 *Drug Handbook.*)

The at least one local anti-infectives can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, triamcinolone acetonide. (See, e.g., pp. 1098-1136 of *Nursing* 2001 *Drug Handbook.*)

The at least one vitamin or mineral can be at least one selected from vitamin A, vitamin B complex, cyanocobalamin, folic acid, hydroxocobalamin, leucovorin calcium, niacin, niacinamide, pyridoxine hydrochloride, riboflavin, thiamine hydrochloride, vitamin C, vitamin D, cholecalciferol, ergocalciferol, vitamin D analogue, doxercalciferol, paricalcitol, vitamin E, vitamin K analogue, phytonadione, sodium fluoride, sodium fluoride (topical), trace elements, chromium, copper, iodine, manganese, selenium, zinc. The at least one calorics can be at least one selected from amino acid infusions (crystalline), amino acid infusions in dextrose, amino acid infusions with electrolytes, amino acid infusions with electrolytes in dextrose, amino acid infusions for hepatic failure, amino acid infusions for high metabolic stress, amino acid infusions for renal failure, dextrose, fat emulsions, medium-chain triglycerides. (See, e.g., pp. 1137-63 of *Nursing* 2001 *Drug Handbook.*)

The present invention also provides at least one of any suitable and/or effective amount of a composition or pharmaceutical composition comprising at least one GLP-1 mimetibody or specified portion or variant, optionally further comprise an effective amount of at least one further compound, protein or composition selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, enteracept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limited to, any of IL-1 to IL-23. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such compositions can also include toxin molecules that are associated, bound, co-formulated or co-administered with at least one antibody or polypeptide of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), *Staphylococcal enterotoxin* A (SEA), B (SEB), or C (SEC), *Streptococcal enterotoxins* and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella cholera-suis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa,* and *Streptococci*. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., *The Merck Manual,* 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

GLP-1 mimetibody or specified portion or variant compositions of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., *Remington's Pharmaceutical Sciences,* $18^{th}$ Edition, Mack Publishing Co. (Easton, Pa.) 1990. Pharmaceutically acceptable carriers can be routinely selected that are suitable for the mode of administration, solubility and/or stability of the GLP-1 mimetibody composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/GLP-1 mimetibody or specified portion or variant components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

GLP-1 mimetibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, the GLP-1 mimetibody or specified portion or variant compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the GLP-1 mimetibody compositions according to the invention are known in the art, e.g., as listed in "Remington: The Science & Practice of Pharmacy", 19th ed., Williams & Williams, (1995), and in the "Physician's Desk Reference", 52nd ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

Formulations. As noted above, the invention provides for stable formulations, which can preferably include a suitable buffer with saline or a chosen salt, as well as optional preserved solutions and formulations containing a preservative as well as multi-use preserved formulations suitable for pharmaceutical or veterinary use, comprising at least one GLP-1 mimetibody or specified portion or variant in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1., 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one GLP-1 mimetibody or specified portion or variant with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one GLP-1 mimetibody or specified portion or variant, and a second vial comprising an aqueous diluent of prescribed buffer or preservative, wherein said packaging material comprises a label that instructs a patient to reconstitute the at least one GLP-1 mimetibody or specified portion or variant in the aqueous diluent to form a solution that can be held over a period of twenty-four hours or greater.

The at least one GLP-1 mimetibody or specified portion or variant used in accordance with the present invention can be produced by recombinant means, including from mammalian cell or transgenic preparations, or can be purified from other biological sources, as described herein or as known in the art.

The range of amounts of at least one GLP-1 mimetibody or specified portion or variant in the product of the present invention includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one GLP-1 mimetibody or specified portion or variant and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one GLP-1 mimetibody or specified portion or variant and preservative in an aqueous diluent is carried out using conventional dissolution and mixing procedures. To prepare a suitable formulation, for example, a measured amount of at least one GLP-1 mimetibody or specified portion or variant in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that may be optimized for the concentration and means of administration used.

The claimed formulations can be provided to patients as clear solutions or as dual vials comprising a vial of lyophilized at least one GLP-1 mimetibody or specified portion or variant that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to at least one of 1-12 months, one-half, one and a half, and/or two years.

The solutions of at least one GLP-1 mimetibody or specified portion or variant in the invention can be prepared by a process that comprises mixing at least one GLP-1 mimetibody or specified portion or variant in an aqueous diluent. Mixing is carried out using conventional dissolution and mixing procedures. To prepare a suitable diluent, for example, a measured amount of at least one GLP-1 mimetibody or specified portion or variant in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that may be optimized for the concentration and means of administration used.

The claimed products can be provided to patients as clear solutions or as dual vials comprising a vial of lyophilized at least one GLP-1 mimetibody or specified portion or variant that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one GLP-1 mimetibody or specified portion or variant that is reconstituted with a second vial containing the aqueous diluent. The clear solution in this case can be up to one liter or even larger in size, providing a large reservoir from which smaller portions of the at least one GLP-1 mimetibody or specified portion or variant solution can be retrieved one or multiple times for transfer into smaller vials and provided by the pharmacy or clinic to their customers and/or patients.

Recognized devices comprising these single vial systems include those pen-injector devices for delivery of a solution such as Humaject®, NovoPen®, B-D®Pen, AutoPen®, and OptiPen®. Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one GLP-1 mimetibody or specified portion or variant in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one GLP-1 mimetibody or specified portion or variant and a selected buffer, preferably a phosphate buffer containing saline or a chosen salt. Mixing the at least one GLP-1 mimetibody or specified portion or variant and buffer in an aqueous diluent is carried out using conventional dissolution and mixing procedures. To prepare a suitable formulation, for example, a measured amount of at least one GLP-1 mimetibody or specified portion or variant in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one GLP-1 mimetibody or specified portion or variant that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one GLP-1 mimetibody or specified portion or variant in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications. The present invention for mimetibodies also provides a method for modulating or treating diabetes, type I or type II diabetes mellitus, including adult onset or juvenile, insulin dependent, non-insulin dependent, and the like, including the associated signs and symptoms, such as but not limited to, insulin resistance, hyperglycemia, hypoglycemia, pancreatitis, Sushing's syndrome, acanthosis nigricans, lipoatrophic diabetes, retinopathy, nephropathy, polyneuropathy, mononeuropathy, autonomic neuropathy, ulcers, foot ulcers, joint problems, infections (e.g., fungal or bacterial), and the like, in a cell, tissue, organ, animal, or patient.

The present invention also provides a method for modulating or treating at least one diabetes associated immune related disease, in a cell, tissue, organ, animal, or patient including, but not limited to, at least one of type I or type II diabetes mellitus, including adult onset or juvenile, insulin dependent, non-insulin dependent, and the like, including the associated signs and symptoms, such as but not limited to, insulin resistance, hyperglycemia, hypoglycemia, pancreatitis, Sushing's syndrome, acanthosis nigricans, lipoatrrophic diabetes, retinopathy, nephropathy, polyneuropathy, mononeuropathy, autonomic neuropathy, ulcers, foot ulcers, joint problems, infections (e.g., fungal or bacterial), and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2001), each entirely incorporated by reference.

Such a method can optionally comprise administering an effective amount of at least one composition or pharmaceutical composition comprising at least one GLP-1 mimetibody or specified portion or variant to a cell, tissue, organ, animal or patient in need of such modulation, treatment or therapy.

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, arteriosclerosis, atherosclerosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), chaotic or multifocal atrial tachycardia, regular narrow QRS tachycardia, specific arrythmias, ventricular fibrillation, His bundle arrythrnias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one GLP-1 mimetibody or specified portion or variant to a cell, tissue, organ, animal or patient in need of such modulation, treatment or therapy.

Any method of the present invention can comprise administering an effective amount of a composition or pharmaceutical composition comprising at least one GLP-1 mimetibody or specified portion or variant to a cell, tissue, organ, animal or patient in need of such modulation, treatment or therapy. Such a method can optionally further comprise co-administration or combination therapy for treating such immune diseases, wherein the administering of said at least one GLP-1 mimetibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an antirheumatic, a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., GLP-1 etin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Mimetibodies can also be used ex vivo, such as in autologous marrow culture. Briefly, bone marrow is removed from a patient prior to chemotherapy and treated with TPO and/or GLP-1, optionally in combination with mimetibodies, optionally in combination with one or more additional cytokines. The treated marrow is then returned to the patient after chemotherapy to speed the recovery of the marrow. In addition, TPO, alone and in combination with GLP-1 mimetibodies and/or GLP-1, can also be used for the ex vivo expansion of marrow or peripheral blood progenitor (PBPC) cells. Prior to chemotherapy treatment, marrow can be stimulated with stem cell factor (SCF) or G-CSF to release early progenitor cells into peripheral circulation. These progenitors are optionally collected and concentrated from peripheral blood and then treated in culture with TPO and mimetibodies, optionally in combination with one or more other cytokines, including but not limited to SCF, G-CSF, IL-3, GM-CSF, IL-6 or IL-11, to differentiate and proliferate into high-density megakaryocyte cultures, which are optionally then be returned to the patient following high-dose chemotherapy. Doses of TPO for ex vivo treatment of bone marrow will be in the range of 100 pg/ml to 10 ng/ml, preferably 500 pg/ml to 3 ng/ml. Doses of mimetibodies will be equivalent in activity to GLP-1 which can be used from 0.1 units/ml to 20 units/ml, preferably from 0.5 units/ml to 2 units/ml, or any range or value therein.

TNF antagonists suitable for compositions, combination therapy, co-administration, devices and/or methods of the present invention (further comprising at least one anti body, specified portion and variant thereof, of the present invention), include, but are not limited to, anti-TNF antibodies, ligand-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

As used herein, a "tumor necrosis factor antibody," "TNF antibody," "TNα antibody," or fragment and the like decreases, blocks, inhibits, abrogates or interferes with TNFα activity in vitro, in situ and/or preferably in vivo. For example, a suitable TNF human antibody of the present invention can bind TNFα and includes anti-TNF antibodies, antigen-binding fragments thereof, and specified mutants or domains thereof that bind specifically to TNFα. A suitable TNF antibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

Chimeric antibody cA2 consists of the antigen binding variable region of the high-affinity neutralizing mouse anti-human TNFα IgG1 antibody, designated A2, and the constant regions of a human IgG1, kappa immunoglobulin. The human IgG1 Fc region improves allogeneic antibody effector function, increases the circulating serum half-life and decreases the immunogenicity of the antibody. The avidity and epitope specificity of the chimeric antibody cA2 is derived from the variable region of the murine antibody A2. In a particular embodiment, a preferred source for nucleic acids encoding the variable region of the murine antibody A2 is the A2 hybridoma cell line.

Chimeric A2 (cA2) neutralizes the cytotoxic effect of both natural and recombinant human TNFα in a dose dependent manner. From binding assays of chimeric antibody cA2 and recombinant human TNFα, the affinity constant of chimeric antibody cA2 was calculated to be $1.04 \times 10^{10}$ M$^{-1}$. Preferred methods for determining monoclonal antibody specificity and affinity by competitive inhibition can be found in Harlow, et al., *Antibodies: A Laboratory Manual*, Cold Spring Harbor Laboratory Press, Cold Spring Harbor, N.Y., 1988; Colligan et al., eds., *Current Protocols in Immunology*, Greene Publishing Assoc. and Wiley Interscience, New York, (1992-2003); Kozbor et al., *Immunol. Today*, 4:72-79 (1983); Ausubel et al., eds. *Current Protocols in Molecular Biology*, Wiley Interscience, New York (1987-2003); and Muller, *Meth. Enzymol.*, 92:589-601 (1983), which references are entirely incorporated herein by reference.

Additional examples of monoclonal anti-TNF antibodies that can be used in the present invention are described in the art (see, e.g., U.S. Pat. No. 5,231,024; Möller, A. et al., *Cytokine* 2(3): 162-169 (1990); U.S. application Ser. No. 07/943,852 (filed Sep. 11, 1992); Rathjen et al., International Publication No. WO 91/02078 (published Feb. 21, 1991); Rubin et al., GLP-1 Patent Publication No. 0 218 868 (published Apr. 22, 1987); Yone et al., GLP-1 Patent Publication No. 0 288 088 (Oct. 26, 1988); Liang, et al., *Biochem. Biophys. Res. Comm.* 137:847-854 (1986); Meager, et al., *Hybridoma* 6:305-311 (1987); Fendly et al., *Hybridoma* 6:359-369 (1987); Bringman, et al., *Hybridoma* 6:489-507 (1987); and Hirai, et al., *J. Immunol. Meth.* 96:57-62 (1987), which references are entirely incorporated herein by reference).

TNF Receptor Molecules. Preferred TNF receptor molecules useful in the present invention are those that bind TNFα with high affinity (see, e.g., Feldmann et al., International Publication No. WO 92/07076 (published Apr. 30, 1992); Schall et al., *Cell* 61:361-370 (1990); and Loetscher et al., *Cell* 61:351-359 (1990), which references are entirely incorporated herein by reference) and optionally possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof (see, e.g., Corcoran et al., *Eur. J. Biochem.* 223:831-840 (1994)), are also useful in the present invention. Truncated forms of the TNF receptors, comprising the ECD, have been detected in urine and serum as 30 kDa and 40 kDa TNFα inhibitory binding proteins (Engelmann, H. et al., *J. Biol. Chem.* 265:1531-1536(1990)). TNF receptor multimeric molecules and TNF immunoreceptor fusion molecules, and derivatives and fragments or portions thereof, are additional examples of TNF receptor molecules which are useful in the methods and compositions of the present invention. The TNF receptor molecules which can be used in the invention are characterized by their ability to treat patients for extended periods with good to excellent alleviation of symptoms and low toxicity. Low immunogenicity and/or high affinity, as well as other undefined properties, may contribute to the therapeutic results achieved.

TNF receptor multimeric molecules useful in the present invention comprise all or a functional portion of the ECD of two or more TNF receptors linked via one or more polypeptide linkers or other nonpeptide linkers, such as polyethylene glycol (PEG). The multimeric molecules can further comprise a signal peptide of a secreted protein to direct expression of the multimeric molecule. These multimeric molecules and methods for their production have been described in U.S. application Ser. No. 08/437,533 (filed May 9, 1995), the content of which is entirely incorporated herein by reference.

TNF immunoreceptor fusion molecules useful in the methods and compositions of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein. TNF immunoreceptor fusion molecules and methods for their production have been described in the art (Lesslauer et al., *Eur. J. Immunol.* 21:2883-2886 (1991); Ashkenazi et al., *Proc. Natl. Acad. Sci. USA* 88:10535-10539(1991); Peppel et al., *J. Exp. Med.* 174:1483-1489(1991); Kolls et al., *Proc. Natl. Acad. Sci. USA* 91:215-219 (1994); Butler et al., *Cytokine* 6(6):616-623 (1994); Baker et al., *Eur. J. Immunol.* 24:2040-2048 (1994); Beutler et al., U.S. Pat. No. 5,447,851; and U.S. application Ser. No. 08/442,133 (filed May 16, 1995), each of which references are entirely incorporated herein by reference). Methods for producing immunoreceptor fusion molecules can also be found in Capon et al., U.S. Pat. No. 5,116,964; Capon et al., U.S. Pat. No. 5,225,538; and Capon et al., *Nature* 337:525-531 (1989), which references are entirely incorporated herein by reference.

A functional equivalent, derivative, fragment or region of TNF receptor molecule refers to the portion of the TNF receptor molecule, or the portion of the TNF receptor molecule sequence which encodes TNF receptor molecule, that is of sufficient size and sequences to functionally resemble TNF receptor molecules that can be used in the present invention (e.g., bind TNFα with high affinity and possess low immunogenicity). A functional equivalent of TNF receptor molecule also includes modified TNF receptor molecules that functionally resemble TNF receptor molecules that can be used in the present invention (e.g., bind TNFα with high affinity and possess low immunogenicity). For example, a functional equivalent of TNF receptor molecule can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., *Current Protocols in Molecular Biology*, Greene Publishing Assoc. and Wiley-Interscience, New York (1987-2003).

Cytokines include, but are not limited to all known cytokines. See, e.g., CopewithCytokines.com. Cytokine antagonists include, but are not limited to, any antibody, fragment or mimetic, any soluble receptor, fragment or mimetic, any small molecule antagonist, or any combination thereof.

Any method of the present invention can comprise a method for treating a protein mediated disorder, comprising administering an effective amount of a composition or pharmaceutical composition comprising at least one GLP-1 mimetibody or specified portion or variant to a cell, tissue, organ, animal or patient in need of such modulation, treatment or therapy. Such a method can optionally further comprise co-administration or combination therapy for treating such immune diseases, wherein the administering of said at least one GLP-1 mimetibody, specified portion or variant thereof, further comprises administering, before concurrently, and/or after, at least one selected from at least one other cytokines such as IL-3, -6 and -11; stem cell factor; G-CSF and GM-CSF.

Typically, treatment of pathologic conditions is effected by administering an effective amount or dosage of at least one GLP-1 mimetibody composition that total, on average, a range from at least about 0.0001 to 500 milligrams of at least one GLP-1 mimetibody or specified portion or variant /kilogram of patient per dose, and preferably from at least about 0.001 to 100 milligrams GLP-1 mimetibody or specified portion or variant /kilogram of patient per single or multiple administration, depending upon the specific activity of contained in the composition. Alternatively, the effective serum concentration can comprise 0.001-5000 µg/ml serum concentration per single or multiple adminstration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.0001, 0.0002, 0.0003, 0.0004, 0.0005. 0.0006, 0.0007, 0.0008, 00009, 0.001, 0.002, 0.003, 0.004, 0.005, 0.006, 0.007, 0.008, 0.009, 0.01, 0.02, 0.03, 0.04, 0.05. 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, and/or 30 mg/kg/administration, or any range, value or fraction thereof, or to achieve a serum concentration of 0.0001, 0.0002, 0.0003, 0.0004, 0.0005. 0.0006, 0.0007, 0.0008, 00009, 0.001, 0.002, 0.003, 0.004, 0.005, 0.006, 0.007, 0.008, 0.009, 0.01, 0.02, 0.03, 0.04, 0.05. 0.06, 0.07, 0.08, 0.09, 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, and/or 500 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.0001 to 100 milligrams per kilogram of body weight. Ordinarily 0.001 to 10, and preferably 0.001 to 1 milligrams per kilogram per administration or in sustained release form is effective to obtain desired results.

As a non-limiting example, treatment of humans or animals can be provided as a one-time or periodic dosage of at least one GLP-1 mimetibody or specified portion or variant of the present invention 0.0001 to 100 mg/kg, such as 0.0002, 0.0003, 0.0004, 0.0005. 0.0006, 0.0007, 0.0008, 00009, 0.001, 0.002, 0.003, 0.004, 0.005, 0.006, 0.007, 0.008, 0.009, 0.01, 0.02, 0.03, 0.04, 0.05. 0.06, 0.07, 0.08, 0.09, 0.1, 0.2, 0.3, 0.4, 0.5, 0.9, 1.0, 1.1, 1.5, 2, 3, 4, 5, 6, 7, 8, 9, or 10 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20, or any combination thereof, using single, infusion or repeated doses.

Dosage forms (composition) suitable for internal administration generally contain from about 0.0001 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the GLP-1 mimetibody or specified portion or variant can be formulated as a solution, suspension, emulsion or lyophilized powder in association, or separately provided, with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Therapeutic Administration. Many known and developed modes of can be used for administering pharmaceutically effective amounts of at least one GLP-1 mimetibody or specified portion or variant according to the present invention. A GLP-1 mimetibody of the present invention can be delivered in a carrier, as a solution, emulsion, colloid, or suspension, or as a powder, using any of a variety of devices and methods suitable for administration by inhalation or other modes described here within or known in the art.

Parenteral Formulations and Administration. Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthtetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

Alternative Delivery. The invention further relates to the administration of at least one GLP-1 mimetibody or specified portion or variant by parenteral, subcutaneous, intramuscular, intravenous, bolus, vaginal, rectal, buccal, sublingual, intranasal, or transdermal means. Protein, GLP-1 mimetibody or specified portion or variant compositions can be prepared for use for parenteral (subcutaneous, intramuscular or intravenous) administration particularly in the form of liquid solutions or suspensions; for use in vaginal or rectal administration particularly in semisolid forms such as creams and suppositories; for buccal, or sublingual administration particularly in the form of tablets or capsules; or intranasally particularly in the form of powders, nasal drops or aerosols or certain agents; or transdermally particularly in the form of a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

Pulmonary/Nasal Administration. For pulmonary administration, preferably at least one GLP-1 mimetibody or specified portion or variant composition is delivered in a particle size effective for reaching the lower airways of the lung or sinuses. According to the invention, at least one GLP-1 mimetibody or specified portion or variant can be delivered by any of a variety of inhalation or nasal devices known in the art for administration of a therapeutic agent by inhalation. These devices capable of dGLP-1 siting aerosolized formulations in the sinus cavity or alveoli of a patient include metered dose inhalers, nebulizers, dry powder generators, sprayers, and the like. Other devices suitable for directing the pulmonary or nasal administration of GLP-1 mimetibody or specified portion or variants are also known in the art. All such devices can use of formulations suitable for the administration for the dispensing of GLP-1 mimetibody or specified portion or variant in an aerosol. Such aerosols can be comprised of either solutions (both aqueous and non aqueous) or solid particles. Metered dose inhalers like the Ventolin® metered dose inhaler, typically use a propellent gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one GLP-1 mimetibody or specified portion or variant is delivered by a dry powder inhaler or a sprayer. There are a several desirable features of an inhalation device for administering at least one GLP-1 mimetibody or specified portion or variant of the present invention. For example, delivery by the inhalation device is advantageously reliable, reproducible, and accurate. The inhalation device can optionally deliver small dry particles, e.g. less than about 10 µm, preferably about 1-5 µm, for good respirability.

Administration of GLP-1 mimetibody or specified portion or variant Compositions as a Spray. A spray including GLP-1 mimetibody or specified portion or variant composition protein can be produced by forcing a suspension or solution of at least one GLP-1 mimetibody or specified portion or variant through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one GLP-1 mimetibody or specified portion or variant composition protein delivered by a sprayer have a particle size less than about 10 µm, preferably in the range of about 1 µm to about 5 µm, and most preferably about 2 µm to about 3 µm.

Formulations of at least one GLP-1 mimetibody or specified portion or variant composition protein suitable for use with a sprayer typically include GLP-1 mimetibody or specified portion or variant composition protein in an aqueous solution at a concentration of about 1 mg to about 20 mg of at least one GLP-1 mimetibody or specified portion or variant composition protein per ml of solution. The formulation can include agents such as an excipient, a buffer, an isotonicity agent, a preservative, a surfactant, and, preferably, zinc. The formulation can also include an excipient or agent for stabilization of the GLP-1 mimetibody or specified portion or variant composition protein, such as a buffer, a reducing agent, a bulk protein, or a carbohydrate. Bulk proteins useful in formulating GLP-1 mimetibody or specified portion or variant composition proteins include albumin, protamine, or the like. Typical carbohydrates useful in formulating GLP-1 mimetibody or specified portion or variant composition proteins include sucrose, mannitol, lactose, trehalose, glucose, or the like. The GLP-1 mimetibody or specified portion or variant composition protein formulation can also include a surfactant, which can reduce or prevent surface-induced aggregation of the GLP-1 mimetibody or specified portion or variant composition protein caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as mimetibodies, or specified portions or variants, can also be included in the formulation.

Administration of GLP-1 mimetibody or specified portion or variant compositions by a Nebulizer. GLP-1 mimetibody or specified portion or variant composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of GLP-1 mimetibody or specified portion or variant composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of GLP-1 mimetibody or specified portion or variant composition protein either directly or through a coupling fluid, creating an aerosol including the GLP-1 mimetibody or specified portion or variant composition protein. Advantageously, particles of GLP-1 mimetibody or specified portion or variant composition protein delivered by a nebulizer have a particle size less than about 10 μm, preferably in the range of about 1 μm to about 5 μm, and most preferably about 2 μm to about 3 μm.

Formulations of at least one GLP-1 mimetibody or specified portion or variant suitable for use with a nebulizer, either jet or ultrasonic, typically include GLP-1 mimetibody or specified portion or variant composition protein in an aqueous solution at a concentration of about 1 mg to about 20 mg of at least one GLP-1 mimetibody or specified portion or variant protein per ml of solution. The formulation can include agents such as an excipient, a buffer, an isotonicity agent, a preservative, a surfactant, and, preferably, zinc. The formulation can also include an excipient or agent for stabilization of the at least one GLP-1 mimetibody or specified portion or variant composition protein, such as a buffer, a reducing agent, a bulk protein, or a carbohydrate. Bulk proteins useful in formulating at least one GLP-1 mimetibody or specified portion or variant composition proteins include albumin, protamine, or the like. Typical carbohydrates useful in formulating at least one GLP-1 mimetibody or specified portion or variant include sucrose, mannitol, lactose, trehalose, glucose, or the like. The at least one GLP-1 mimetibody or specified portion or variant formulation can also include a surfactant, which can reduce or prevent surface-induced aggregation of the at least one GLP-1 mimetibody or specified portion or variant caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like.

Additional agents known in the art for formulation of a protein such as at least one GLP-1 mimetibody or specified portion or variant protein can also be included in the formulation.

Administration of GLP-1 mimetibody or specified portion or variant compositions By A Metered Dose Inhaler. In a metered dose inhaler (MDI), a propellant, at least one GLP-1 mimetibody or specified portion or variant, and any excipients or other additives are contained in a canister as a mixture including a liquefied compressed gas. Actuation of the metering valve releases the mixture as an aerosol, preferably containing particles in the size range of less than about 10 μm, preferably about 1 μm to about 5 μm, and most preferably about 2 μm to about 3 μm. The desired aerosol particle size can be obtained by employing a formulation of GLP-1 mimetibody or specified portion or variant composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one GLP-1 mimetibody or specified portion or variant for use with a metered-dose inhaler device will generally include a finely divided powder containing at least one GLP-1 mimetibody or specified portion or variant as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like. Preferably the propellant is a hydrofluorocarbon. The surfactant can be chosen to stabilize the at least one GLP-1 mimetibody or specified portion or variant as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein such as protein can also be included in the formulation.

One of ordinary skill in the art will recognize that the methods of the current invention can be achieved by pulmonary administration of at least one GLP-1 mimetibody or specified portion or variant compositions via devices not described herein.

Mucosal Formulations and Administration. For absorption through mucosal surfaces, compositions and methods of administering at least one GLP-1 mimetibody or specified portion or variant include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

Oral Formulations and Administration. Formulations for oral rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, manriitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations may contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. Nos. 5,879,681 and 5,5,871,753 are used to deliver biologically active agents orally are known in the art.

Transdermal Formulations and Administration. For transdermal administration, the at least one GLP-1 mimetibody or specified portion or variant is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

Prolonged Administration and Formulations. It can be sometimes desirable to deliver the compounds of the present invention to the subject over prolonged periods of time, for example, for periods of one week to one year from a single administration. Various slow release, dGLP-1 t or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, can be formulated,in a gel, for example, an aluminum monostearate gel with, e.g. sesame oil, suitable for injection. Particularly preferred salts are zinc salts, zinc tannate salts, pamoate salts, and the like. Another type of slow release dGLP-1 t formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, dGLP-1 t or implant formulations, e.g. gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

Having generally described the invention, the same will be more readily understood by reference to the following examples, which are provided by way of illustration and are not intended as limiting.

EXAMPLE 1

Cloning and Expression of a GLP-1 mimetibody in Mammalian Cells. A typical mammalian expression vector contains at least one promoter element, which mediates the initiation of transcription of mRNA, the GLP-1 mimetibody or specified portion or variant coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLV1, HIV1 and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (±), pcDNA/Zeo (±) or pcDNA3.1/Hygro (±) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded GLP-1 mimetibody or specified portion or variant. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of GLP-1 mimetibody or specified portion or variants.

The expression vectors pC1 and pC4 contain the strong promoter (LTR) of the Rous Sarcoma Virus (Cullen, et al., Molec. Cell. Biol. 5:438-447 (1985)) plus a fragment of the CMV-enhancer (Boshart, et al., Cell 41:521-530 (1985)).

Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells. The vector pC4 is used for the expression of GLP-1 mimetibody or specified portion or variant. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate. The amplification of the DHFR genes in cells resistant to methotrexate (MTX) has been well documented (see, e.g., F. W. Alt, et al., J. Biol. Chem. 253:1357-1370 (1978); J. L. Hamlin and C. Ma, Biochem. et Biophys. Acta 1097:107-143 (1990); and M. J. Page and M. A. Sydenham, Biotechnology 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molec. Cell. Biol. 5:438-447 (1985)) plus a fragment isolated from the enhancer of the immediate early gene of human cytomegalovirus (CMV) (Boshart, et al., Cell 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human b-actin promoter, the SV40 early or late promoters or the long terminal repeats from other retroviruses, e.g., HIV and HTLVI. Clontech's Tet-Off and Tet-On gene expression systems and similar systems can be used to express the GLP-1 in a regulated way in mammalian cells (M. Gossen, and H. Bujard, Proc. Natl. Acad. Sci. USA 89: 5547-5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with restriction enzymes and then dephosphorylated using calf intestinal phosphatase by procedures known in the art. The vector is then isolated from a 1% agarose gel.

The DNA sequence encoding the complete GLP-1 mimetibody or specified portion or variant is used, corresponding to HC and LC variable regions of a GLP-1 mimetibody of the present invention, according to known method steps. Isolated nucleic acid encoding a suitable human constant region (i.e., HC and LC regions) is also used in this construct.

The isolated variable and constant region encoding DNA and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 μg of the expression plasmid pC4 is cotransfected with 0.5 μg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 μg/ml G418. After 2 days, the cells are trypsinized and seeded in hybridoma cloning plates (Greiner, Germany) in alpha minus MEM supplemented with 10, 25, or 50 ng/ml of methotrexate plus 1 μg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot or by reverse phase HPLC analysis.

EXAMPLE 2

Non-Limiting Example of a GLP-1 mimetibody of the Invention. GLP-1 is a 37-amino acid peptide secreted from the L-cells of the intestine following an oral glucose challenge. A mimetibody construct incorporating a biologically active GLP-1 (7-37) peptide, variant or derivative is expected to prolong the in vivo lifetime of the peptide and provide a novel therapy for lowering blood glucose in Type 2 diabetic patients. Peptides encoding the native GLP-1 (7-37) peptide or a DPP-IV resistant analogue can be incorporated into the mimetibody scaffold. Several of these molecules have been made, and the resulting mimetibodies have demonstrated activity in functional in vitro cell-based assays. It should be noted that different in vitro assays and in vivo models can be used in these studies and the potencies may not be comparable to each other or to results presented herein.

To generate GLP-1 mimetibody variants, the GLP-1 peptide, the linker, the hinge, or the CH2 and CH3 sequences in the mimetibody could be deleted, added, substituted, mutated or modified to improve expression, potency, stability, or effector functions.

The wild-type GLP-1 sequence (GLP-1 MMB of SEQ ID NO: 69), as well as DPP-IV resistant GLP-1 variants, such as GLP-1 MMB of SEQ ID NO: 71 (A2S) or GLP-1 MMB of SEQ ID NO: 70 (A2G) can be incorporated into a mimetibody scaffold. Mutations of the peptide could be made to improve the properties of a GLP-1 mimetibody. For example mutations in the amino terminal residues may improve signaling while mutations in the helical domain may stabilize the helix and thereby improve binding to the receptor and/or stability of the mimetibody.

The length and composition of the linker could be mutated to vary the flexibility or stability of the attachment between the GLP-1 peptide and the Fc region. Different isotypes could be incorporated into the hinge region of the molecule. In addition, mutations could be made within the hinge region of the mimetibody to stabilize the molecule. For example, the human IgG4 hinge could be mutated to make the Ser$^{228}$->Pro variant, to stabilize the interchain disulfide bonds in the mimetibody. Variations within the Fc portion of the mimetibody could be made to improve the stability of the molecule and to change effector functions such as FcR binding. For example, one could use human or murine isotypes (or variations of these molecules) such as IgG4 with Ala/Ala mutations.

GLP-1 mimetibody of the Present Invention. A specific, non-limiting, example of this invention is the GLP-1 mimetibody construct (SEQ ID NO:2) according to Formula (I):

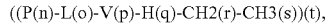

where P is a single copy of the bioactive GLP-1 peptide (7-36), L is a tandem repeat of either Gly-Ser or Gly-Gly-Gly-Ser (SEQ ID NO: 16) flexible linker, V is the C-terminal of $V_H$ sequence, i.e., the J region of a naturally occurring IgG, H is the complete IgG4 hinge region and CH2 & CH3 are of the IgG4 isotype subclass. It is expected that the half-life of this construct will be many times that of the GLP-1 peptide alone or its variant or derivative and similar to that of an IgG.

In addition to the basic structure described above, variants with potentially favorable biological characteristics are described. These include constructs that may have a decreased tendency to self-associate, reduced immune effector functions or decreased immunogenicity. Other modifications that confer desired characteristics such as improved conformation of the biologically active peptide, and transfer across the blood-brain barrier are envisioned. The proposed variants and modifications may be combined in any fashion to yield constructs with desired activities.

Using recombinant DNA methods, the GLP-1 peptide was inserted into an intermediate vector between an immunoglobulin signal peptide and a human J sequence. This was done using complementary synthetic oligonucletides with ends compatible with the restriction sites present in the vector. These oligonucleotides comprised coding sequences for the GLP-1 peptide, and a flexible linker composed of two GGGS (SEQ ID NO: 16) repeats. A restriction fragment containing the above-mentioned functional elements was then transferred into an expression vector. This vector contained the anti-CD4 immunoglobulin promoter and enhancer, and the coding sequence for the human IgG4 hinge sequence, HC constant region 2 (CH2) and constant region 3 (CH3) as well as the necessary elements for plasmid replication and selection in bacteria and selection for stable expressers in mammalian cells.

This plasmid was introduced into the HEK293E cells and expression of the wt GLP-1 MMB was achieved in transiently transfected cells. Purification of GLP-1 MMB was accomplished by standard protein A and Superose 12 affinity chromatography, yielding approximately 1.5 mg/L of transfected cells. This protein was the starting material for the experiments described below.

The amino acid sequence of a GLP-1 mimetibody is shown in FIG. 1. Functional domains are annotated above the peptide coding sequence. It is thought that the J sequence will provide even more flexibility to allow the GLP-1 segment to assume the proper conformation and allow the peptides to protrude from the globular structure of the immunoglobulin enabling appropriate orientation for binding to the GLP-1 receptor. CH2 and CH3 regions constitute the bulk of the protein. One of the reasons that immunoglobulins are believed to have a long serum half-life is their ability to bind the FcRn that extends the serum half-life by returning pinocytosed immunoglobulin back to the extracellular space. The binding site of the FcRn overlaps the junction of the CH2 and CH3 regions (Sheilds et al, 2001, J. Biol. Chem., vol. 276 (9), 6591-6604).

It is well known that two IgG heavy chains are assembled during cellular processing via disulfide bonds between cysteines located in the hinge region to form a homodimer. It is expected that this will also occur between the modified peptides to form the assembled GLP-1 mimetibody construct. The expected structure of a GLP-1 mimetibody contains two GLP-1 peptides.

Similar experiments were repeated for the GLP-1 MMB of SEQ ID NO:4 and similar results were obtained.

EXAMPLE 3

Figure 2B:
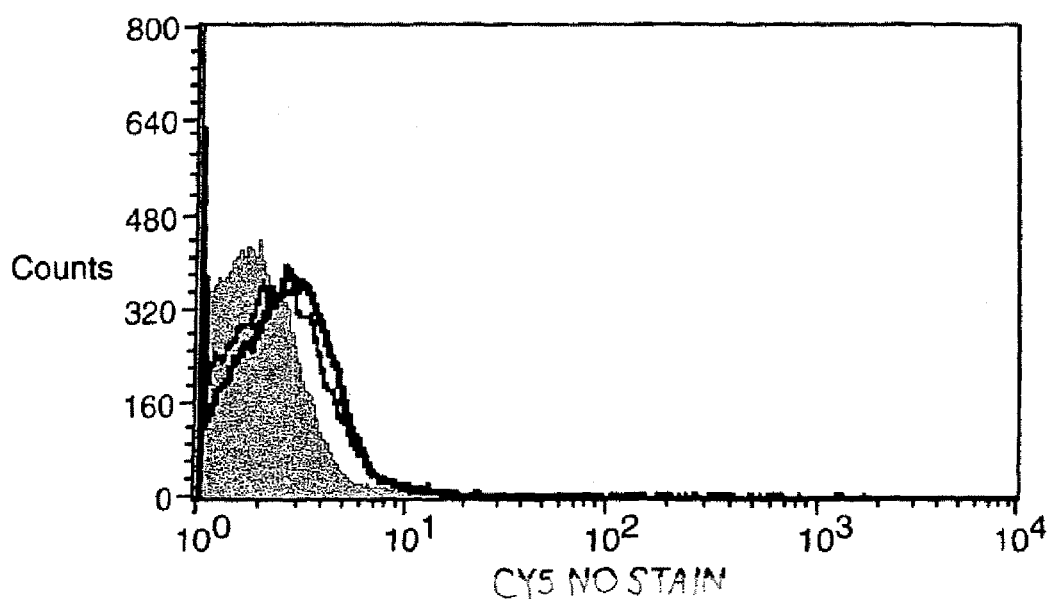
Figure 2C:
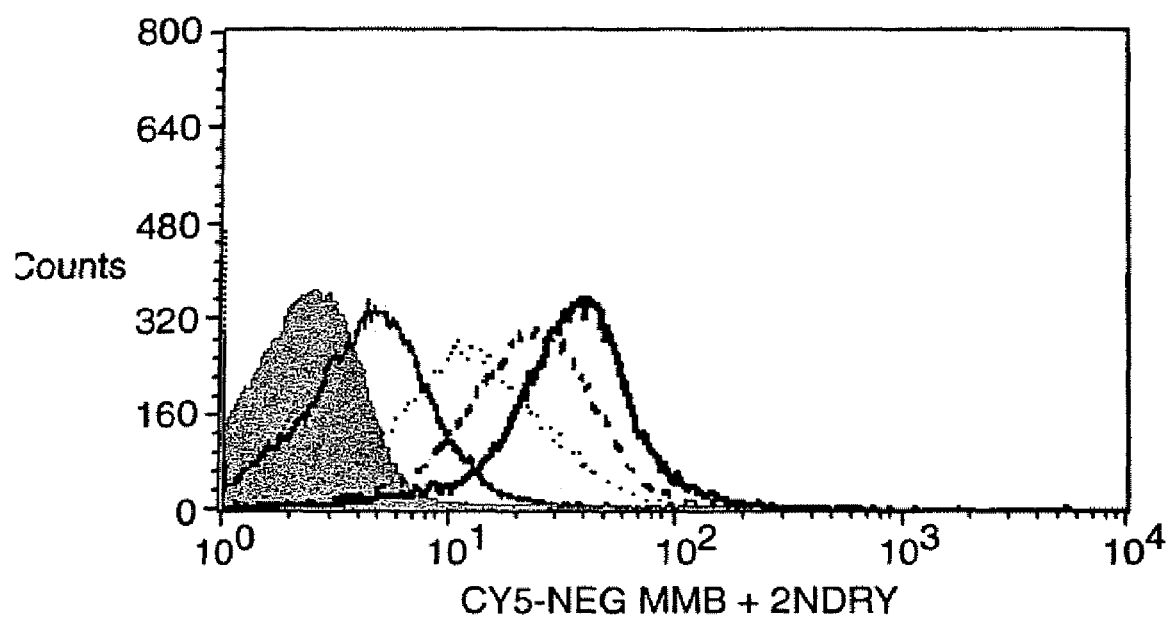
Figure 3A:
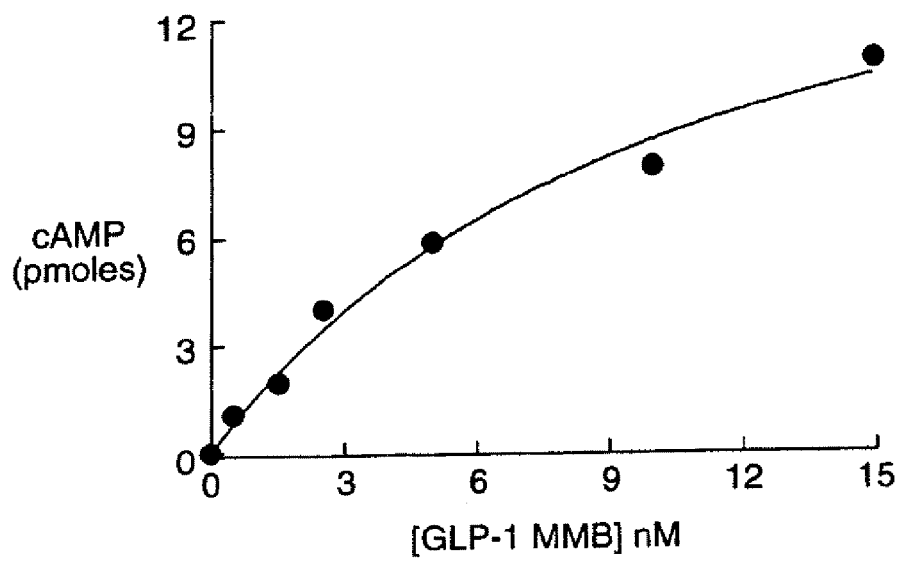
FIGS. 3A-3E illustrate cAMP assays of GLP-1 MMB.
Figure 3B:
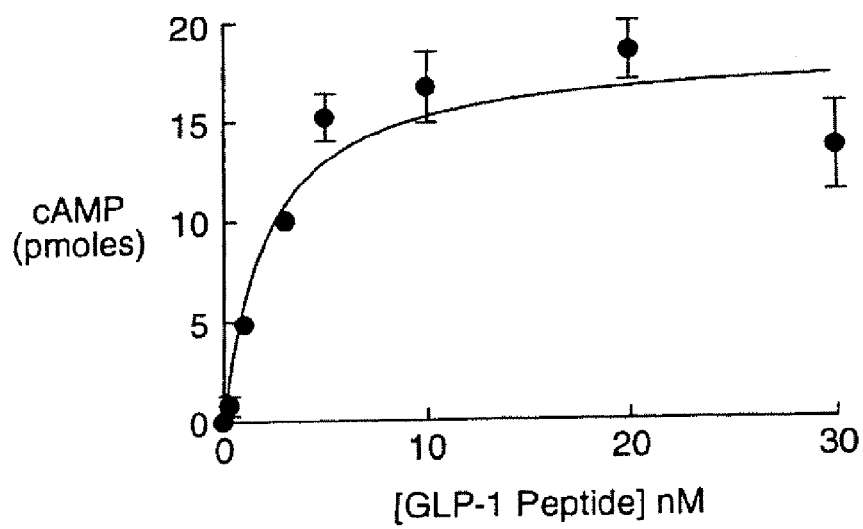
Figure 3C:
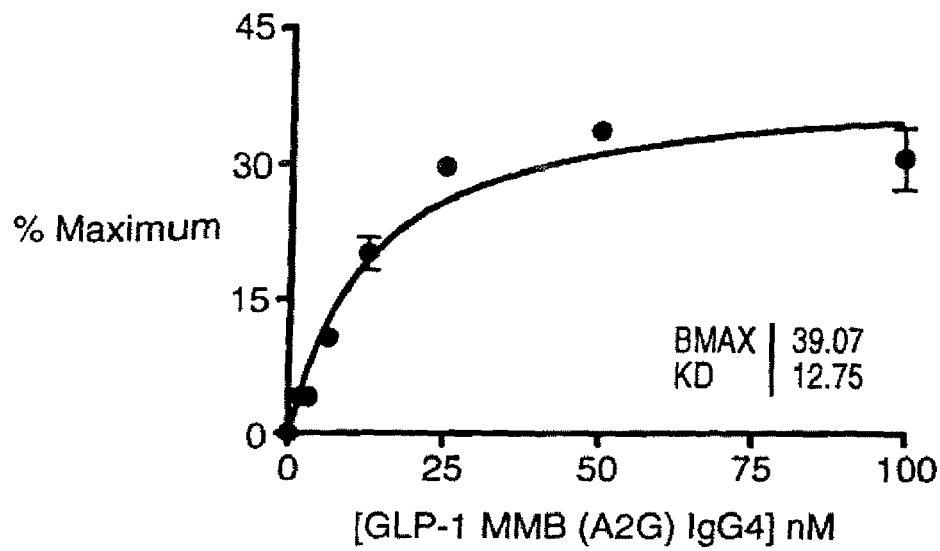
Figure 3D:
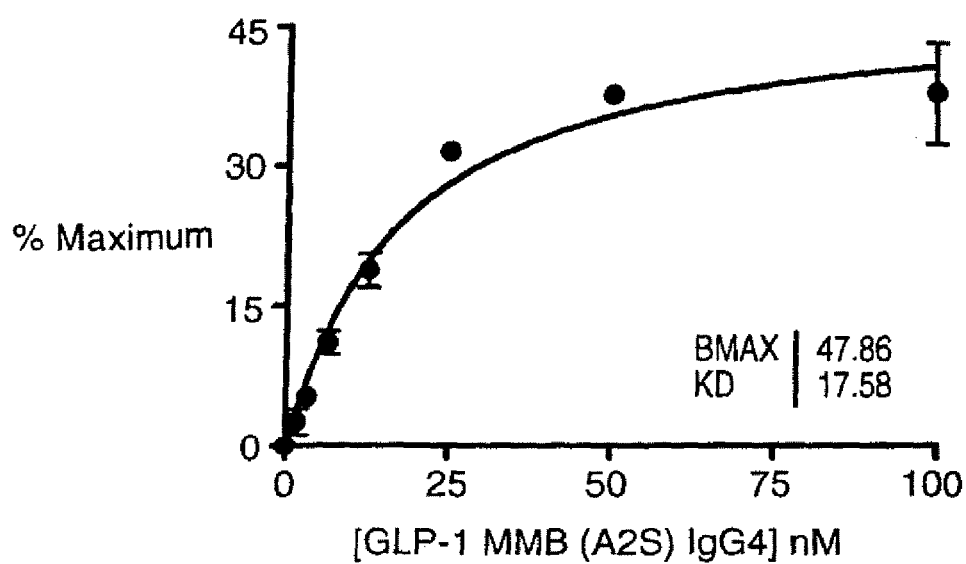
Figure 3E:
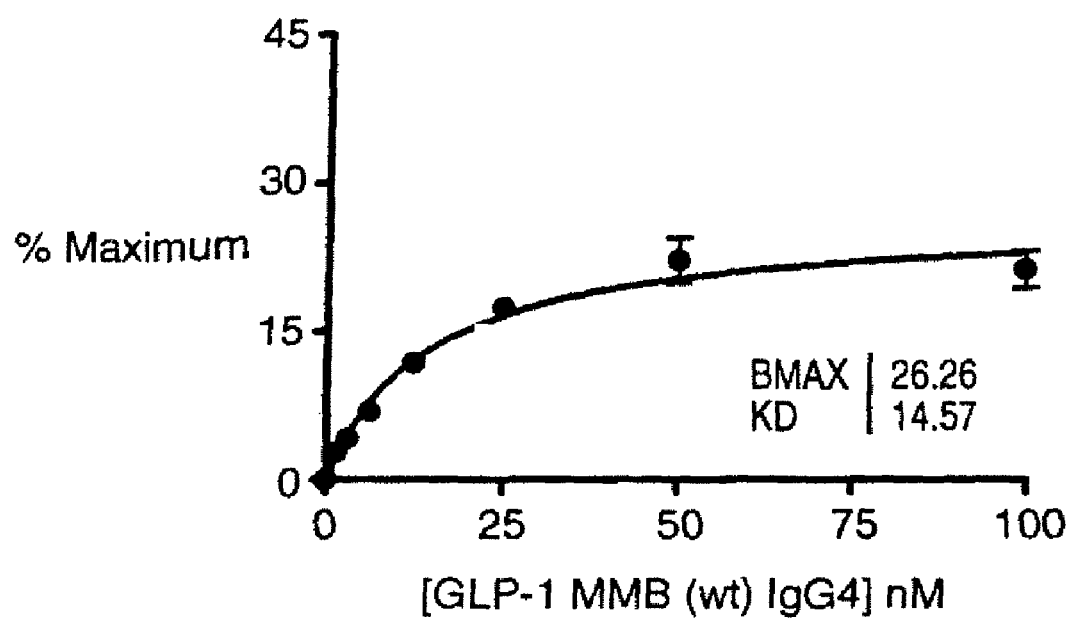

FACS Binding Assay. The activity of a GLP-1 mimetibody was tested in an in vitro FACS binding assay. To determine whether the GLP-1 MMB binds the GLP-1R, HEK293 cells ($1 \times 10^6$ cells) over-expressing the GLP-1 R were incubated with GLP-1 MMB of SEQ ID NO: 69 (20 nM) for 2 hours at 4° C. The cells were washed, and a fluorescently labeled secondary detection antibody (1 μg/mL goat anti-human IgG, Fc gamma specific) was added for 30 minutes at 4° C. The fluorescence intensity of the cells was monitored via flow cytometry. FIG. 2A shows that GLP-1 MMB of SEQ ID NO: 69 binds to HEK293 cells over-expressing the GLP-1R (grey, GLP-1 MMB of SEQ ID NO: 69 but no secondary; black, secondary only; red, negative control MMB and secondary; blue, GLP-1 MMB and secondary). FIG. 2B shows that the GLP-1 MMB of SEQ ID NO: 69 does not bind to the control HEK293 cells (grey, GLP-1 MMB of SEQ ID NO: 69 but no secondary; black, secondary only; blue, GLP-1 MMB of SEQ ID NO: 69 and secondary). FIG. 2C shows that a GLP-1 peptide analogue (A2S) is able to compete with GLP-1 MMB of SEQ ID NO: 69 for binding to HEK293 cells over-expressing the GLP-1 R (grey, GLP-1 MMB of SEQ ID NO: 69 but no secondary; black, GLP-1 MMB of SEQ ID NO: 69 and secondary; orange, GLP-1 MMB of SEQ ID NO: 69, 0.2 nM competitor, secondary; blue, GLP-1 MMB of SEQ ID NO: 69, 20 nM competitor, secondary; red, GLP-1 MMB of SEQ ID NO: 69, 100 nM competitor, secondary).

Similar experiments were repeated for the GLP-1 MMB of SEQ ID NO:4 and similar results were obtained.

EXAMPLE 4 cAMP Assay. GLP-1 binds to its receptor, a G-protein coupled receptor, resulting in a dose-dependent increase in the signaling molecule, 3',5'-cyclic AMP (cAMP). cAMP can be measured with an in vitro assay in cells expressing the GLP-1 R (Applied Biosystems). Briefly, Rinm cells (100,000 cells) were incubated with increasing concentrations of GLP-1 peptide (0-30 nM) or A GLP-1 MMB (0-100 nM). The cells were lysed, and the amount of cAMP was determined using a competitive assay that employs an alkaline-phosphatase labeled cAMP conjugate and a chemiluminescent substrate (Tropix® CDPD®). The concentration dependent cAMP activity for the wt GLP-1 MMB of SEQ ID NO: 69 (FIG. 3A) is comparable to the GLP-1 peptide (FIG. 3B) ($EC_{50}$=11 nM vs. 0.4 nM, respectively). In a similar experiment, GLP-1 MMB of SEQ ID NO: 70 (A2G) in an IgG4 scaffold (FIG. 3C) and GLP-1 MMB of SEQ ID NO: 71 (A2S) in an IgG4 scaffold (FIG. 3D) both increased cAMP levels in Rinm cells to a significantly higher level than wt GLP-1 MMB of SEQ ID NO: 69 in an IgG4 scaffold.

Similar experiments were repeated for the GLP-1 MMB of SEQ ID NO:4 and similar results were obtained.

EXAMPLE 5

In Vitro Activity of GLP-1 MMB as Measured by cAMP: A LANCE™ cAMP assay was used to measure the functional activity of GLP-1 MMB in INS-1E cells, a rat insulinoma cell line expressing the rat GLP-1 receptor.

Materials/Methods: INS-1E cells were cultured in RPMI 1640/10% FBS/1% L-glutamine/1% Sodium Pyruvate/1% Non-essential Amino Acids/50 μM β-Mercaptoethanol and maintained at 37° C. in a humidified incubator with 5% $CO_2$. LANCE cAMP kits were purchased from Perkin Elmer (Boston, Mass.). The GLP-1 peptide was purchased from Sigma (St Louis, Mo.). Data was analyzed in GraphPad PRISM, version 4.03.

cAMP Assay: INS-1E cells were plated at 100,000 cells/well in 96-well plates (Costar 3610) and allowed to recover 4 days in normal growth media. Media was aspirated from the wells and 24 μl of Alexa Fluor 647 anti-cAMP antibody (LANCE cAMP Kit, Perkin Elmer, Boston, Mass.) was added followed by 24 μl of GLP-1 MMB of SEQ ID NO 4 (in PBS/0.5% BSA/0.5 mM IBMX). The cells were stimulated at room temperature for 7 minutes and lysed per the manufacture's protocol. The plates were incubated at room temperature for 1 hour and the fluorescence intensity was measured at 665 nm. cAMP concentrations were determined using a standard curve.

Figure 18A:
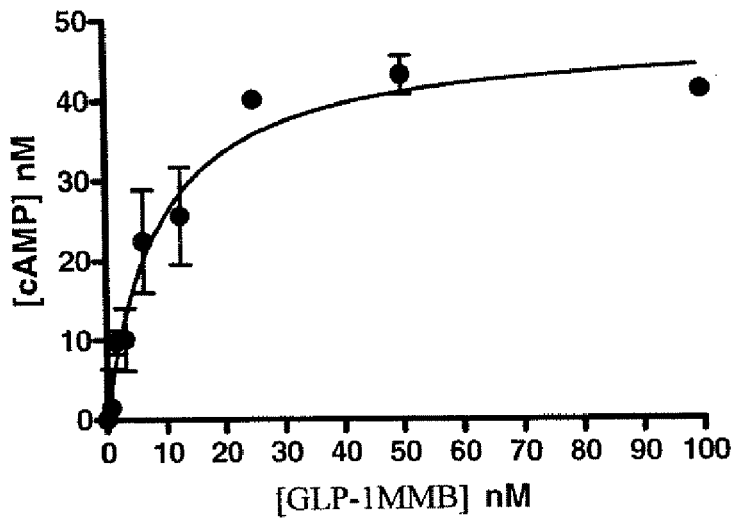
FIG. 18A demonstrates cAMP response in rat INS-1E cells to increasing concentrations of GLP-1 MMB. The data were fit to a hyperbola providing an $EC_{50}$ of 8.7 nM and a maximal amount of secreted cAMP of 48.3 nM.
Figure 18B:
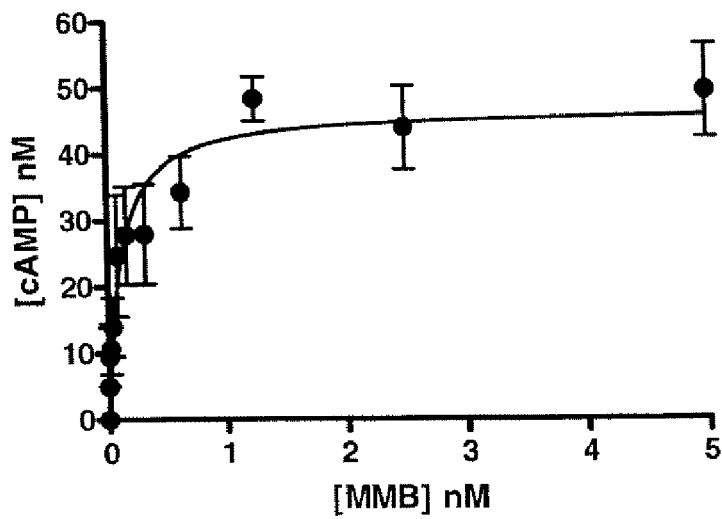
FIG. 18B demonstrates cAMP response in rat INS-1E cells to increasing concentrations of GLP-1 peptide. The data were fit to a hyperbola providing an $EC_{50}$ of 0.11 nM and a maximal amount of secreted cAMP of 46.7 nM.

Results: The concentration of cAMP was plotted against the concentration of GLP-1 MMB of SEQ ID NO 4 (nM) and the points were fit to a hyperbola, providing an $EC_{50}$ of 8.7 nM (FIG. 18A). The data obtained with GLP-1 peptide was plotted in the same manner, providing an $EC_{50}$ of 0.11 nM (FIG. 18B).

EXAMPLE 6

Figure 4:
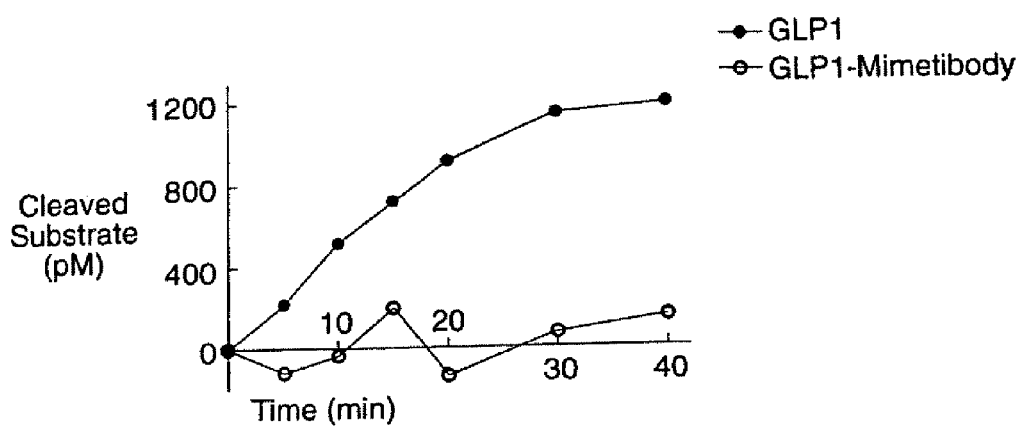
FIG. 4 illustrates the resistance of GLP-1 MMB to DPP-IV cleavage.

DPP-IV cleavage assay. Since GLP-1 is rapidly inactivated by DPP-IV, an in vitro assay was established to quantitate intact (i.e. uncleaved) GLP-1 MMB of SEQ ID NO: 69. Briefly, GLP-1 MMB of SEQ ID NO: 69 or peptide (1.2 nM) was incubated at room temperature with DPP-IV (1 μg/mL, R&D Systems). After various times (0, 5, 10, 15, 20, 30, 40 minutes), a DPP-IV inhibitor (100 μM, Linco) was added to quench the reaction. The amount of intact GLP-1 MMB of SEQ ID NO: 69 or peptide was measured using the GLP-1 Active ELISA (Linco) and the GLP-1 MMB of SEQ ID NO: 69 or peptides for the respective standard curves. FIG. 4 shows that the GLP-1 MMB of SEQ ID NO: 69 was significantly more resistant to cleavage by DPP-IV, relative to the GLP-1 peptide.

Similar experiments were repeated for the GLP-1 MMB of SEQ ID NO:4 and similar results were obtained.

EXAMPLE 7

Figure 5:
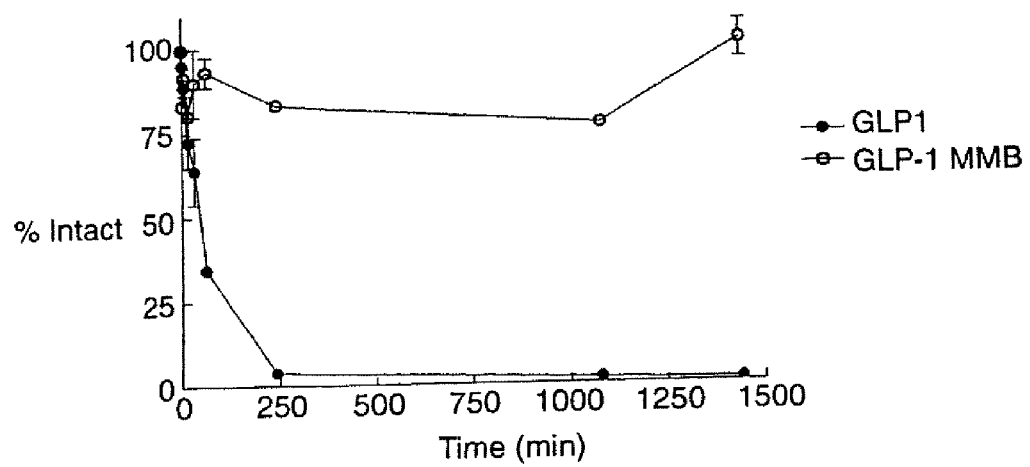
FIG. 5 shows the stability of GLP-1 MMB in serum.

Human Serum stability assay. The stability of the GLP-1 MMB in serum was also measured to ensure that other serum proteases were not able to cleave and inactivate the GLP-1 MMB. Briefly, GLP1 peptide or the GLP-1 MMB of SEQ ID NO: 71 (30 nM) was incubated in human serum at 37° C. After various times, the reactions were quenched with a DPP-IV inhibitor (100 μM, Linco), and the samples were analyzed using the GLP-1 Active ELISA from Linco. FIG. 5 shows that the GLP-1 MMB of SEQ ID NO: 71 is stable in human serum for 24 hours while the peptide is decayed rapidly.

Similar experiments were repeated for the GLP-1 MMB of SEQ ID NO:4 and similar results were obtained.

EXAMPLE 8

Figure 6A:
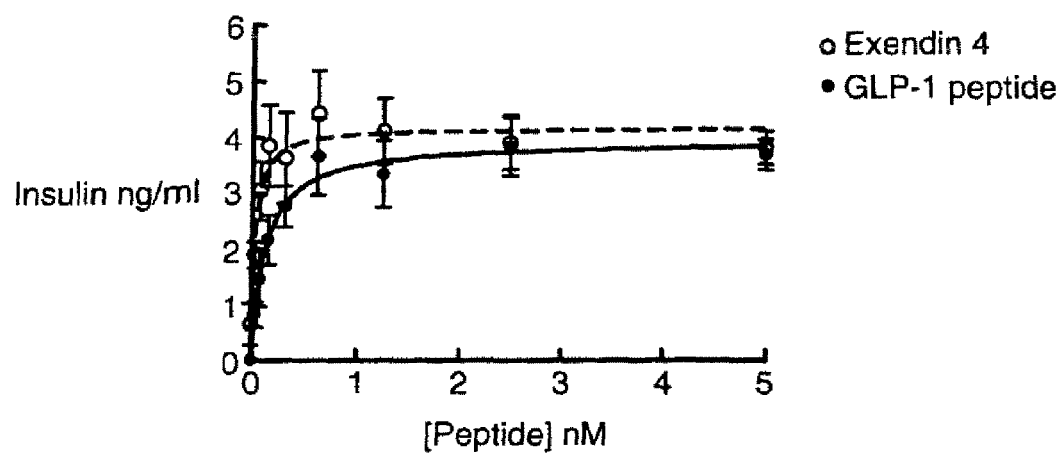
FIG. 6A shows that GLP-1 (7-36) peptide and exendin-4 peptide stimulates insulin release in RINm cells.
Figure 6B:
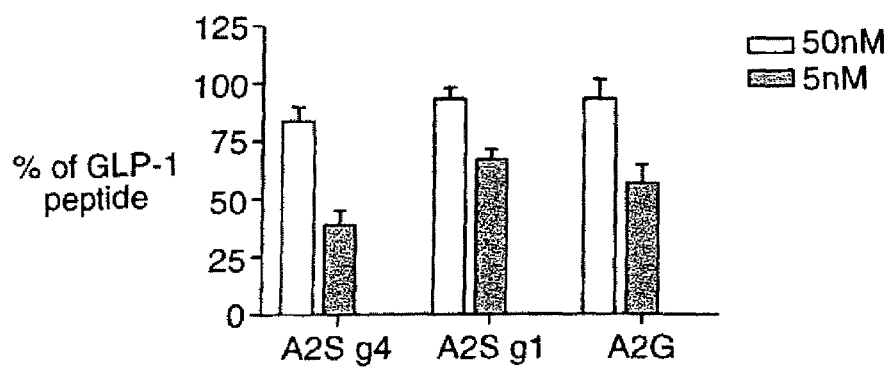
FIG. 6B shows that GLP-1 (A2S) MMB in either IgG1 or IgG4 (Ala/Ala, Ser→Pro) scaffold, or GLP-1 (A2G) MMB in IgG4 (Ala/Ala, Ser->Pro) scaffold are active in stimulating insulin secretion in RINm cells.

GLP-1 MMB causes insulin secretion in RINm cells. To test the effect of GLP-1 MMB in insulin secretion, RINm cells were treated with increasing concentrations of GLP-1 (7-36) peptide (0-5 nM), exendin-4 peptide (0-5 nM), or various GLP-1 mimetibodies (5 or 50 nM) and the amount of insulin secreted was measured via ELISA. All GLP-1 MMBs tested had activities in stimulating insulin secretion in RINm cells (FIG. 6). At 50 nM, the MMBs had activities comparable to that of the wide-type GLP-1 (7-36) peptide.

EXAMPLE 9

In vitro Activity of GLP-1 MMB as Measured by Insulin Secretion. A further insulin secretion assay was developed to measure functional in vitro activity of the GLP-1 MMB of SEQ ID NO 4., Cell culture: INS-1E cells were cultured in RPMI 1640/10% FBS/1% L-glutamine/1% Sodium Pyruvate/1% Non-essential Amino Acids/50 μM β-Mercaptoethanol and maintained at 37° C. in a humidified incubator with 5% $CO_2$. Data was analyzed in GraphPad PRISM, version 4.03.

Insulin Secretion Assay: INS-1E cells were plated at 100,000 cells/well in 96-well plates (Costar 3610) and allowed to recover 4 days in normal growth media. The cells were washed twice and 0.1 ml of KRBH buffer/3 mM glucose was added. The cells were allowed to equilibrate in this buffer for 2 hours. The media was removed and 0.12 ml of GLP-1 MMB of SEQ ID NO 4 in KRBH with 6.5 mM glucose was added per well. Twenty microliters of supernatant was removed per well for the T=0 time point. The cells then were incubated for two hours at 37° C. at 5% $CO_2$ and twenty microliters of supernatant were removed per well. Supernatants were frozen at −20° C. until the insulin ELISA was performed. Insulin concentrations were determined using a the Ultra Sensitive Rat Insulin ELISA kit (Crystal Chem).

Figure 19:
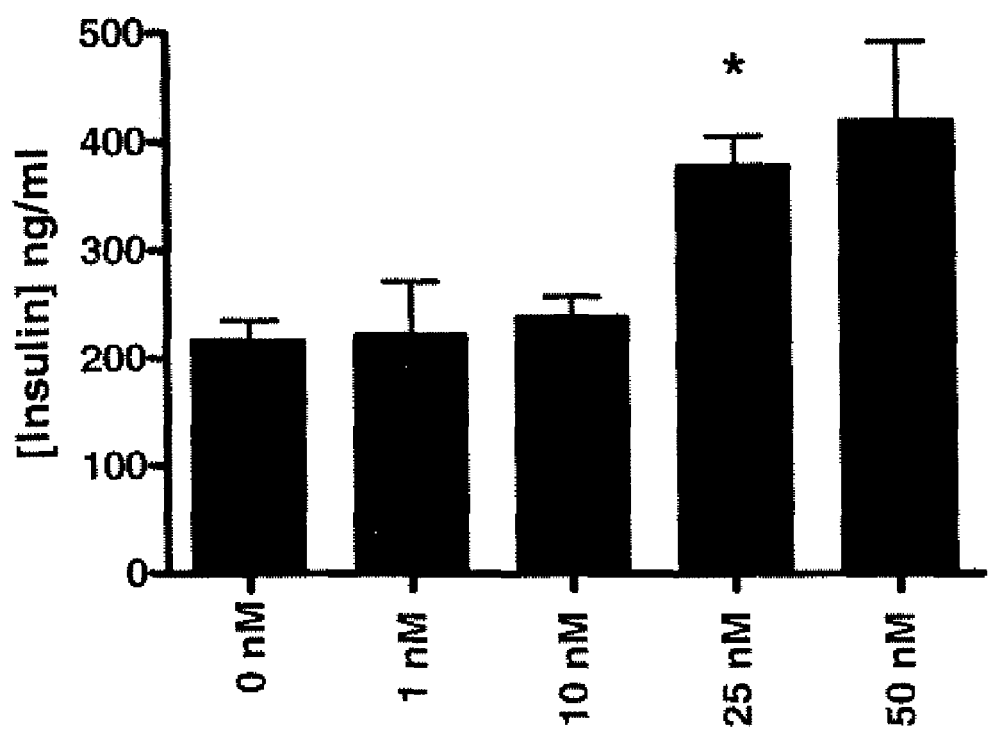
FIG. 19 demonstrates insulin secretion in rat INS-1E cells at increasing concentrations of GLP-1 MMB.

Results: The data was plotted as the amount of insulin secreted at each concentration of GLP-1 MMB of SEQ ID NO 4 (FIG. 19). GLP-1 MMB of SEQ ID NO 4 (25 nM) significantly increased the amount of insulin secreted into the supernatant.

EXAMPLE 10

Figure 7A:
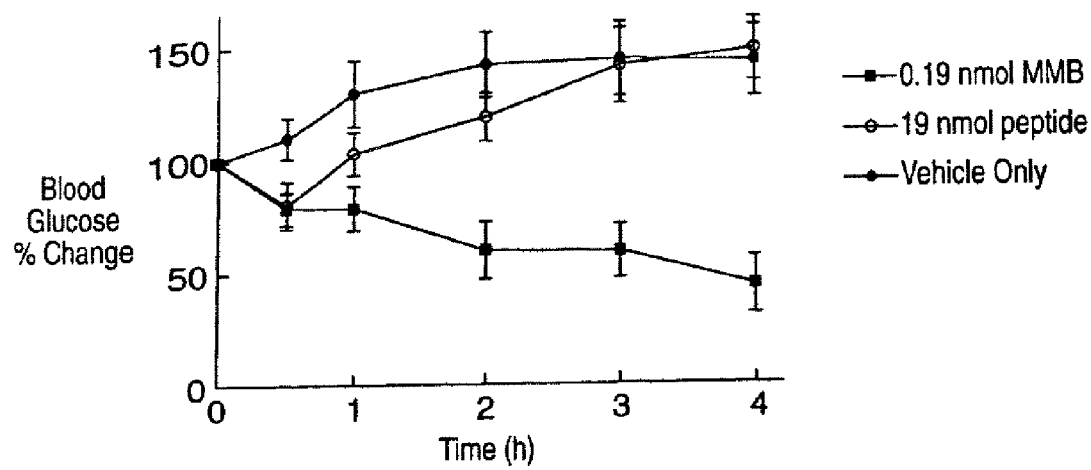
FIG. 7 demonstrates that GLP-1 MMB lowers glucose (FIG. 7A) in a dose-dependent manner (FIG. 7B).
Figure 7B:
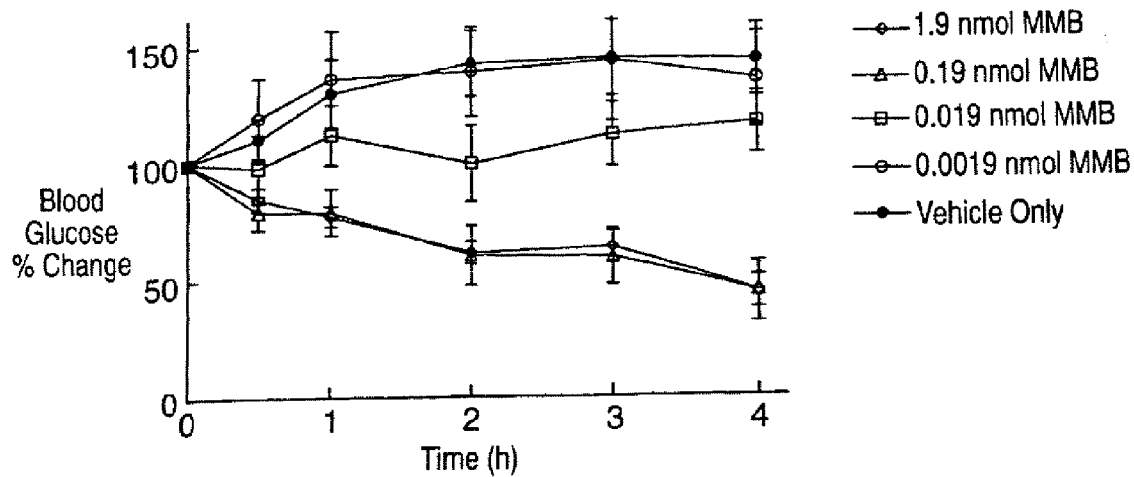

GLP-1 MMB lowers glucose level in db/db mice. Six week old db/db mice were fasted for two hours and then dosed intravenously with vehicle, GLP-1 peptide, or GLP-1 MMB of SEQ ID NO: 71 (A2S). Blood glucose was monitored 0.5, 1, 2, 3, and 4 hours post-dosing. The GLP-1 peptide lowered blood glucose at 30 minutes, but by 60 minutes, the blood glucose began to increase again likely due to the short half-life of the GLP-1 peptide. In comparison, GLP-1 MMB of SEQ ID NO: 71 (A2S) at a dose 100-fold lower than the GLP-1 peptide dose induced a decrease in blood glucose throughout the entire 4 hour period (FIG. 7A). In addition, the decrease in blood glucose was dose dependent (FIG. 7B).

Similar experiments were repeated for the GLP-1 MMB of SEQ ID NO:4 and similar results were obtained.

EXAMPLE 11

Pharmacokinetics of GLP-1 MMBs in mice and in cynomolgus monkeys. To measure the pharmacokinetics of four GLP-1 mimetibodies (A2G, A2S, exedin-cap, and wt) (SEQ ID NO: 70, SEQ ID NO: 71, SEQ ID NO: 72, and SEQ ID NO: 69, respectively), C57/B16 mice were intravenously dosed with 1 mg/kg of the MMBs. Plasma was obtained via cardiac puncture after sacrificing mice at different time point. Various ELISAs were used to measure Fc, total MMB, active MMB, and acive peptide as they were metabolized in the animal. Active MMB reflects the intact N-terminus of the peptide still attached to the Fc region of the mimetibody. Substitution of the second amino acid in the peptide (alanine) with either a serine or a glycine prolonged the lifetime of the active MMB in circulation.

Figure 8:
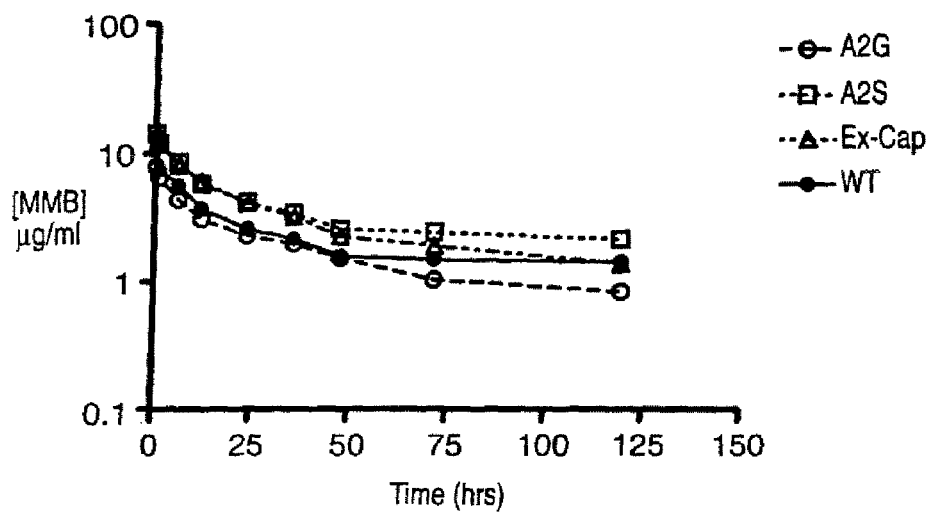
FIG. 8 shows the pharmacokinetic profile of four GLP-1 MMBs (A2G, A2S, Ex-cap and wild-type) in cynomolgus monkey.
Figure 9:
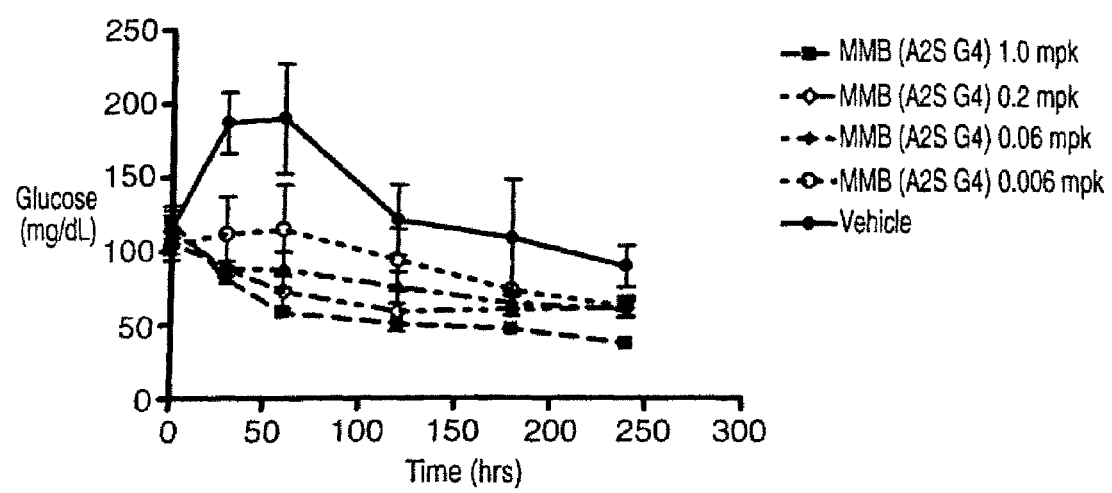
FIG. 9 shows the effects of GLP-1 MMB during an oral glucose tolerance test in diabetic mice.

Cynomolgus monkey were injected intravenously with 1.0 mg/kg of four different GLP-1 MMB constructs and serum samples were taken at different time points from 10 minutes to 5 days following dosing. Serum samples were evaluated by ELISA to quantify intact MMB. As illustrated in FIG. 8, all four MMBs exhibit a rapid distribution phase, followed by a slower clearance phase. Pharmacokinetic constants were calculated for each of the constructs to indicate a T½ of approximately 3 days with similar exposure determined by AUC from T=0 to T=120 hours.

Similar experiments were repeated for the GLP-1 MMB of SEQ ID NO:4 and similar results were obtained.

EXAMPLE 12

Pharmacokinetic characterization of GLP-1 MMB in rats and monkeys. GLP-1 MMB was engineered to maintain the bioactivity of GLP-1 while extending its pharmacokinetic (PK) profile.

Pharmacokinetics in rats: Sprague-Dawley-derived rats were treated with a single subcutaneous or intravenous dose of GLP-1 MMB of SEQ ID NO 4 (3.0 mg/kg, lot #8833173) (1). Approximately 300 μl of blood were collected at various times following dosing in sodium citrate (3.8%) containing protease inhibitors (Roche Complete EDTA free, Roche Applied Science, Indianapolis, Ind.) and DPP4 inhibitors (Linco, St. Charles, Mo.). Plasma was isolated and stored at −80° until samples could be analyzed. The concentration of intact GLP-1 MMB of SEQ ID NO 4 was measured using a mesoscale discovery (MSD) technology [3-7]. Briefly, plasma samples were serially diluted by BioMek Fx for a total of 4 dilutions, neat, 1:8, 1:64 and 1:512. Identical standard curves in neat plasma were included on each plate. GLP-1 MMB of SEQ ID NO 4 was captured on MSD plates by biotinylated monoclonal antibody (CNTO1626) designed to detect intact N-terminus of GLP-1 MMB of SEQ ID NO 4. Ruthenium labeled monoclonal antibody recognizing linker region on GLP-1 MMB of SEQ ID NO 4 (CNTO712) were added for detection and the luminescence responses were determined using the MSD sector imager 6000 reader. GLP-1 MMB of SEQ ID NO 4 level was calculated using sigmoidal dose-response curve (GraphPad PRISM).

Pharmacokinetics in monkeys: Cynomolgus monkeys were dosed intravenously with GLP-1 MMB of SEQ ID NO 4 (1.0 mg/kg, lot #8833013) at Diabetes Research Institute, University of Miami (2). The monkeys were chemically restrained with ketamine HCl (100 mg/mL, 10 mg/kg) prior to dosing and blood collections. GLP-1 MMB of SEQ ID NO 4 was administered at a dose volume of 2.2 mL/kg at a rate of 1 mL/minute. Approximately 2 mL of blood was collected at various time points following dosing in sodium citrate (3.8%) containing protease inhibitors (Roche Complete EDTA free, Roche Applied Science, Indianapolis, Ind.) and DPP4 inhibitors (Linco, St. Charles, Mo.). Plasma was isolated and stored at −80° until samples could be analyzed. GLP-1 MMB of SEQ ID NO 4 concentrations in the plasma was measured as described above.

Data analysis: Non-compartmental analysis (NCA) was employed to calculate the pharmacokinetic parameters of GLP-1 MMB of SEQ ID NO 4 (WinNonlin, Version 5.1, Pharsight Corporation, Mountain View, Calif.). The maximum serum concentration, Cmax and the time to reach Cmax (Tmax), were obtained from inspection of the serum concentration vs. time profiles. The area under the concentration curve (AUC) from time 0 to the last time point with quantifiable levels of GLP-1 MMB of SEQ ID NO 4 was calculated (AUC (0-7d) for rat, AUC (0-21d) for monkey), as well as the AUC from time 0 to infinity. The AUC values were obtained by linear trapezoidal integration. The terminal rate constant (λz) was determined by least-squares regression analysis of the log-linear portion of the terminal phase. The terminal half-life, t½, was calculated from the ratio of 0.693 and λz.

Figure 20A:
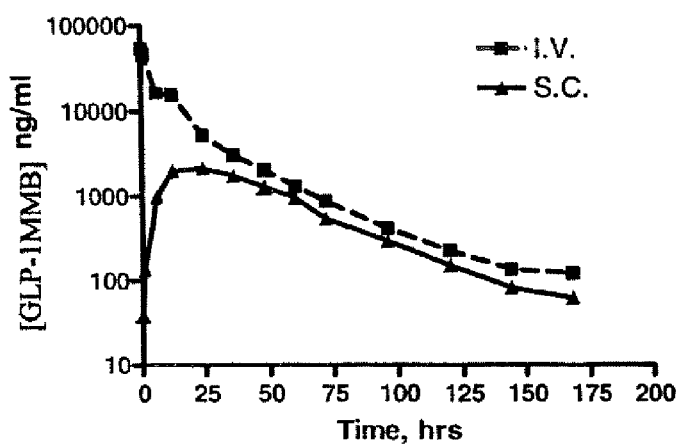
FIG. 20A demonstrates GLP-1 MMB levels in rat plasma following single iv and sc administration (3 mg/kg).

Results: Pharmocokinetics in rats: The plasma pharmacokinetic profile of GLP-1 MMB of SEQ ID NO 4 in rats after a single sc and iv administration is shown (FIG. 20A). The full pharmacokinetic analysis from the rat data is summarized in Table 1. The terminal half-life of GLP-1 MMB of SEQ ID NO 4 was modeled to be 1.5 days following iv dosing and 1.7 days following sc dosing. The bioavalibility of GLP-1 MMB of SEQ ID NO 4 following sc administration was approximately 22%.

TABLE 2

Pharmacokinetic characteristics of GLP-1MMB of SEQ ID NO 4 in SD rats following single sc and iv administration (3 mg/kg).

| Material (route) | | Cmax ug/mL | Tmax day | AUC(0-7 d) day*ug/mL | AUCinf day*ug/mL | Cl mL/day/kg | Vss mL/kg | t½ day | F % |
|---|---|---|---|---|---|---|---|---|---|
| GLP-1MMB (iv) | mean | 53.91 | na | 23.61 | 23.86 | 125.90 | 110.07 | 1.48 | na |
| of SEQ ID NO 4 | sd | 5.03 | na | 1.11 | 1.06 | 5.59 | 7.32 | 0.49 | na |
| | % CV | 9.3 | na | 4.7 | 4.4 | 4.4 | 6.7 | 33.0 | na |
| GLP-1MMB (sc) | mean | 2.29 | 0.83 | 5.04 | 5.20 | na | na | 1.73 | 21.85 |
| of SEQ ID NO 4 | sd | 0.10 | 0.29 | 0.20 | 0.30 | na | na | 1.10 | 1.85 |
| | % CV | 4.5 | 34.6 | 4.0 | 5.7 | na | na | 63.7 | 8.5 |
| GLP-1MMB | mean | 53.91 | na | 23.61 | 23.86 | 125.90 | 110.07 | 1.48 | na |
| of SEQ ID NO 4 (iv) | sd | 5.03 | na | 1.11 | 1.06 | 5.59 | 7.32 | 0.49 | na |
| | % CV | 9.3 | na | 4.7 | 4.4 | 4.4 | 6.7 | 33.0 | na |
| GLP-1MMB | mean | 2.29 | 0.83 | 5.04 | 5.20 | na | na | 1.73 | 21.85 |
| of SEQ ID NO 4 (sc) | sd | 0.10 | 0.29 | 0.20 | 0.30 | na | na | 1.10 | 1.85 |
| | % CV | 4.5 | 34.6 | 4.0 | 5.7 | na | na | 63.7 | 8.5 |

Figure 20B:
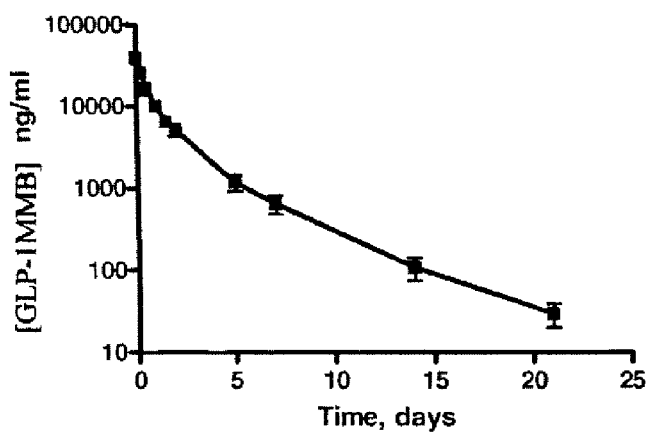
FIG. 20B demonstrates GLP-1 MMB levels in monkey plasma following single iv administration (1 mg/kg).

Pharmocokinetics in monkeys: The plasma pharmacokinetic profile of GLP-1 MMB in monkeys following a single iv administration is shown (FIG. 20B). The full pharmacokinetics analysis is summarized in Table 2. The terminal half-life of GLP-1 MMB in monkey was modeled to be 2.9 days.

TABLE 3

Pharmacokinetic characteristics of GLP-1MMB of SEQ ID NO 4 in cynomolgus monkeys following single iv administration (1 mg/kg).

| PK Parameters | mean conc (ug/mL) | sd | % CV |
|---|---|---|---|
| Cmax ug/mL | 40.09 | 9.28 | 23.1 |
| AUC(0-21) day*ug/mL | 41.92 | 10.25 | 24.4 |
| AUCinf day*ug/mL | 42.05 | 10.29 | 24.5 |
| Cl mL/day/kg | 24.81 | 6.38 | 25.7 |
| Vss mL/kg | 50.18 | 19.07 | 38.0 |
| Vz mL/kg | 105.40 | 34.92 | 33.1 |
| t½ day | 2.93 | 0.37 | 12.7 |

EXAMPLE 13

Effects of GLP-1 MMB during an oral glucose tolerance test in diabetic mice. Eight-week old diabetic db/db mice were fasted for 6 hours prior to a subcutaneous injection of the GLP-1 MMB of SEQ ID NO: 71 (0.02 to 2 mg/kg). Following dosing, mice were fasted for an additional six hours and a baseline fasting blood glucose was measured. At t=0, mice were given an oral gavage of 1.0 mg/g glucose, and blood glucose was measured at various times. Results shown in FIG. 9 indicate that the GLP-1 MMB of SEQ ID NO: 71 was effective in lowering the glucose excursion during an oral glucose tolerance test at all doses tested.

Similar experiments were repeated for the GLP-1 MMB of SEQ ID NO:4 and similar results were obtained.

EXAMPLE 14

Figure 10:
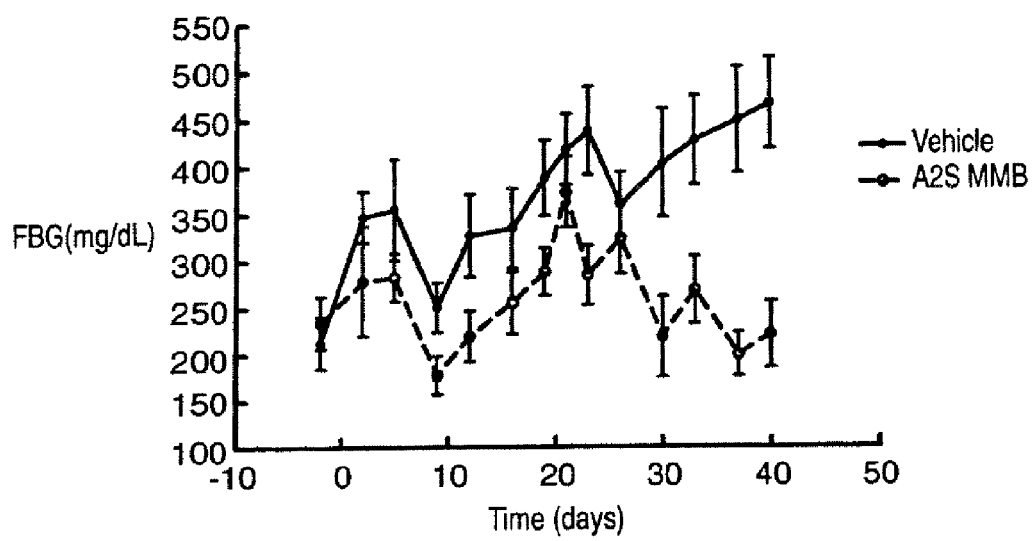
FIG. 10 shows the effects of GLP-1 MMB on fasting blood glucose during chronic dosing to diabetic mice.

Effects of GLP-1 MMB on fasting blood glucose during chronic dosing to diabetic mice. Ten-week old diabetic db/db mice were subcutaneously dosed daily with vehicle or GLP-1 MMB of SEQ ID NO: 71 (1 mg/kg) for six weeks. Fasting blood glucose was measured twice per week during the course of the study. The fasting blood glucose was reduced in the treated animals relative to the controls throughout the study (FIG. 10), and by six weeks, the difference was more than 200 mg/dL (466 vs 221 mg/dL, control and treated animals respectively).

Similar experiments were repeated for the GLP-1 MMB of SEQ ID NO:4 and similar results were obtained.

EXAMPLE 15

Figure 11:
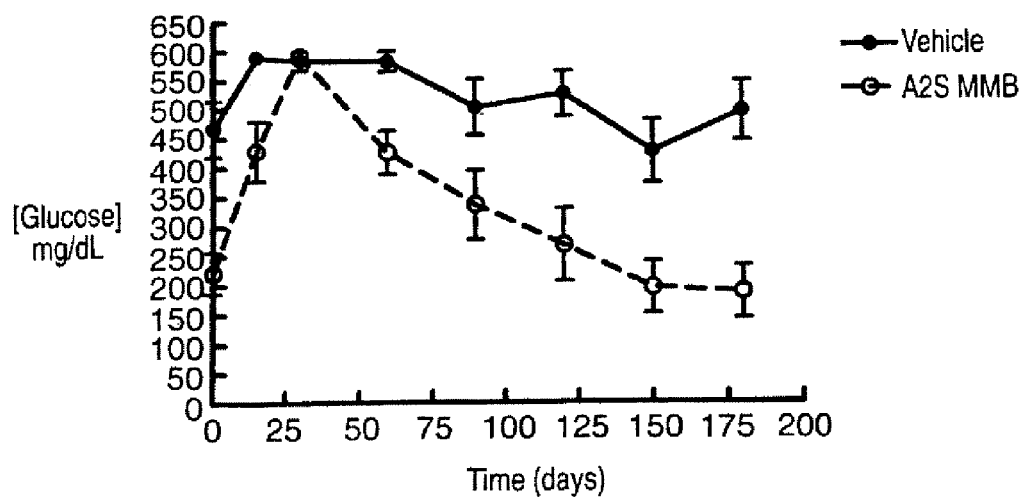
FIG. 11 shows the effects of GLP-1 MMB on oral glucose tolerance test after chronic dosing to diabetic mice.

Effects of GLP-1 MMB on oral glucose tolerance test after chronic dosing to diabetic mice. As in Example 11, ten-week old diabetic db/db mice were dosed daily with vehicle or GLP-1 MMB of SEQ ID NO: 71 (1 mg/kg) for six weeks. After 40 days of dosing, the mice were given an oral glucose tolerance test. Briefly, at t=0, mice were given an oral gavage of 1.0 mg/g glucose, and blood glucose was measured at various times. Results shown in FIG. 11 indicate that the GLP-1 MMB of SEQ ID NO: 71 was effective in lowering the glucose excursion during an oral glucose tolerance test suggesting that mice treated chronically with GLP-1 MMB of SEQ ID NO: 71 are able to dispose of a glucose load more efficiently relative to control animals.

Similar experiments were repeated for the GLP-1 MMB of SEQ ID NO:4 and similar results were obtained.

EXAMPLE 16

Figure 12:
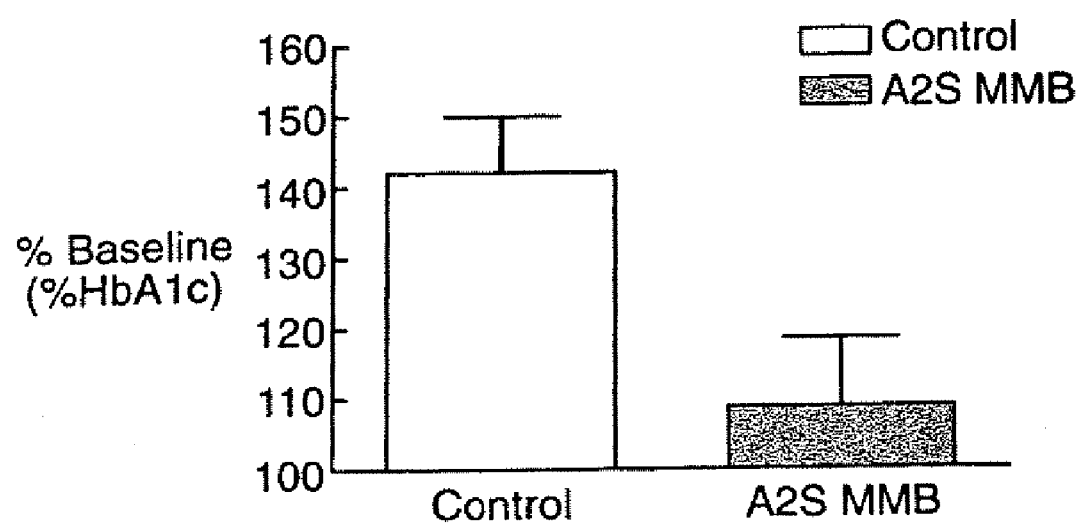
FIG. 12 shows the effects of GLP-1 MMB on reducing HbA1c after chronic dosing to diabetic mice.

Effects of GLP-1 MMB on reducing HbA1c after chronic dosing to diabetic mice. As in Examples 11 and 12, ten-week old diabetic db/db mice were dosed daily with vehicle or GLP-1 MMB of SEQ ID NO: 71 (1 mg/kg) for six weeks. Before and after six-weeks of dosing, whole blood samples were taken and analyzed for percent HbA1c. As shown in FIG. 12, the HbA1C of the GLP-1 treated animals increased by 109 percent during the six-week period whereas the control treated animals increased by 142 percent. This data suggests that the treated animals are better able to regulate their blood glucose over a chronic period relative to the controls.

Similar experiments were repeated for the GLP-1 MMB of SEQ ID NO:4 and similar results were obtained.

EXAMPLE 17

Figure 13A:
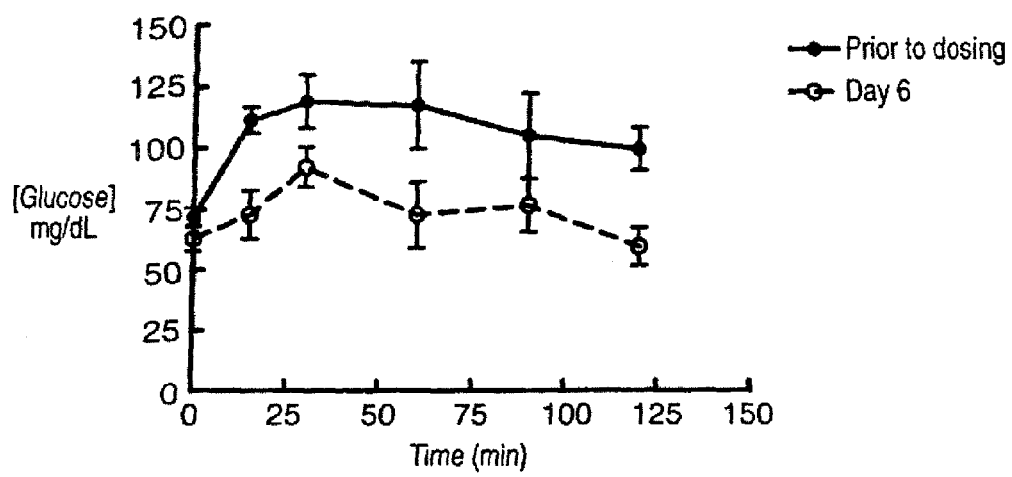
FIG. 13 shows the effects of GLP-1 MMB on blood glucose (FIG. 13A) and insulin (FIG. 13B) levels in an oral glucose tolerance test in normal cynomolgus monkeys.
Figure 13B:
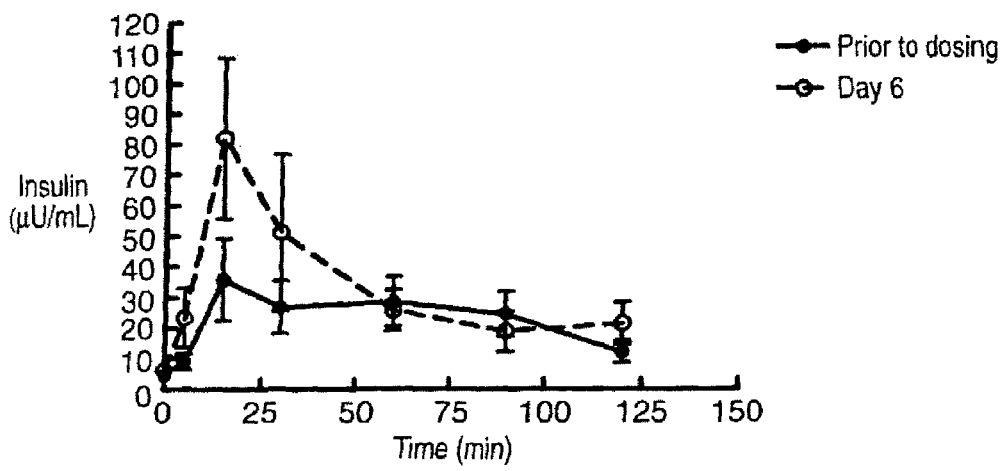

Effects of GLP-1 MMB on an oral glucose tolerance test in normal cynomolgus monkeys. An oral glucose tolerance test (OGTT) was done in normal cynomolgus monekys prior to and six days after a single dose of the GLP-1 MMB of SEQ ID NO: 71 (1 mg/kg). Briefly, at t=0, monkeys were given an oral gavage of 2.0 mg/g glucose, and blood glucose was measured at various times. The blood glucose levels were significantly reduced in the OGTT done six days after dosing (FIG. 13A), and the insulin levels were significantly increased (FIG. 13B). This suggests the GLP-1 MMB of SEQ ID NO: 71 is causing insulin secretion from the pancreas at elevated glucose concentrations.

Similar experiments were repeated for the GLP-1 MMB of SEQ ID NO:4 and similar results were obtained.

EXAMPLE 18

Figure 14:
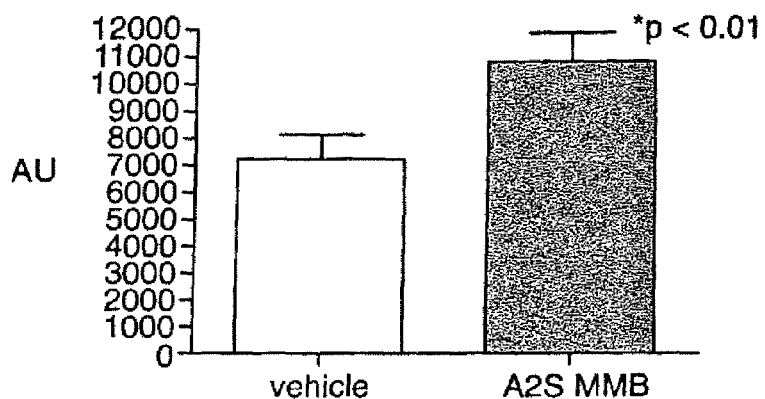
FIG. 14 shows the effects of GLP-1 MMB on insulin staining in islets of diabetic mice after a single dose.

Effects of GLP-1 MMB on insulin staining in islets of diabetic mice (db/db) after a single dose. Twelve-week old diabetic mice (db/db) were treated with a single subcutaneous dose of the GLP-1 MMB of SEQ ID NO: 71 (1.5 mg/kg), and the pancreata were harvested four weeks later. The pancreata were sectioned and stained for the presence of insulin. As shown in FIG. 14, there was significantly more insulin staining in the treated animals relative to the control animals.

Similar experiments were repeated for the GLP-1 MMB of SEQ ID NO:4 and similar results were obtained.

EXAMPLE 19

Figure 15:
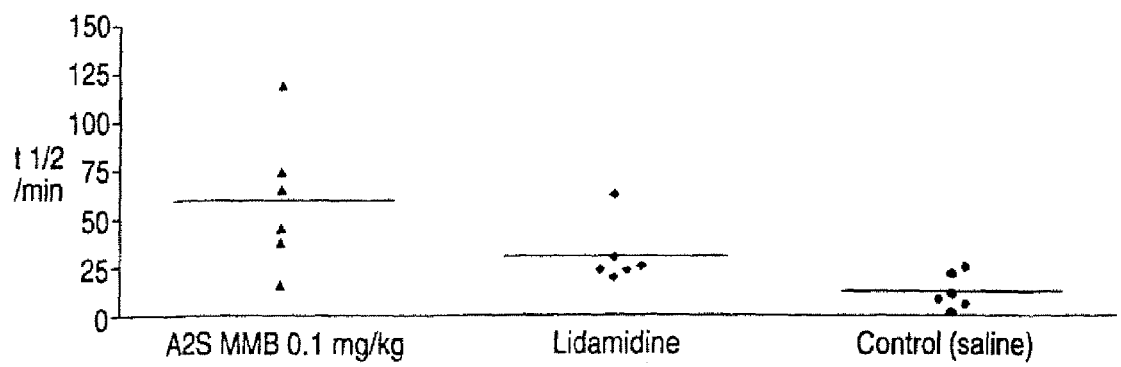
FIG. 15 demonstrates that GLP-1 MMB delays gastric emptying in normal dogs.

GLP-1 MMB delays gastric emptying in normal dogs. A gastric cannula was surgically implanted into female beagle dogs (10-15 kg) under general anesthesia and allowed to recover for at least 2 weeks. Dogs were fasted for 24 hours after which water was freely available. The gastric cannula was opened and gastric juice and food remnants were removed with 40-50 ml of lukewarm water. Groups of six dogs were dosed subcutaneously with lidamidine, an alpha2 agonist (0.63 mg/kg), 60 minutes before the meal, a positive control for delay of gastric emptying. Dogs dosed with the vehicle control or GLP-1 MMB of SEQ ID NO: 70 (0.1 mg/kg) were dosed intravenously in the cephalic vein 15 minutes before the meal. Five minutes before the meal, the gastric cannula was opened to determine the amount of fluid present in stomach for baseline value and fluid was promptly reintroduced. Then a test meal consisting of 250 ml of a glucose solution (5 g/l) was administered via the cannula and allowed to remain in the stomach for 30 minutes. Gastric contents were drained from the stomach to measure total volume after 30 minutes. One ml of gastric contents was retained for analysis and the remaining volume was reintroduced into the stomach via the cannula. Assessment of the gastric content volume and retrieval of samples was repeated at 60, 90, and 120 minutes. Glucose concentrations were evaluated for collected samples and used to determine the absolute amount of glucose remaining in the stomach at each time point. The percentage of glucose retained in the stomach was determined from the starting value and the concentration of glucose at each time point and plotted as a function of time. The time at which 50% of the gastric contents were retained was determined by fitting of the curves to a single exponential. As shown in FIG. 15, 50% of the gastric contents were emptied in dogs dosed with vehicle in 12.35±3.69 minutes following while the lidamidine positive control and GLP-1 MMB of SEQ ID NO: 70 dosed dogs showed a significant delay in gastric emptying (30.60±6.47 and 59.23±14.46, respectively).

Similar experiments were repeated for the GLP-1 MMB of SEQ ID NO 4 and similar results were obtained.

EXAMPLE 20

Figure 16:
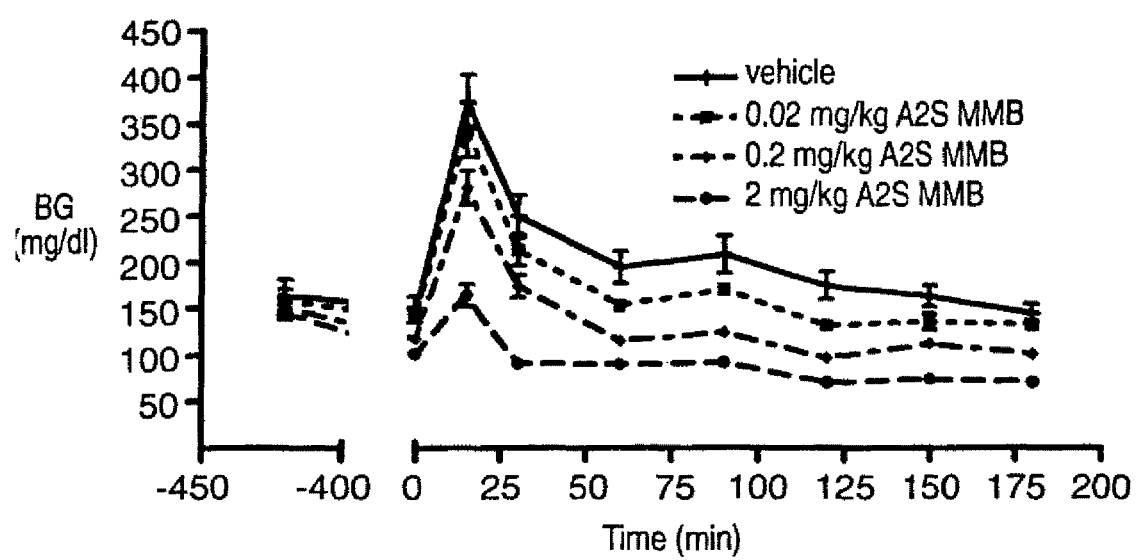
FIG. 16 demonstrates that GLP-1 MMB lowers blood glucose following an oral glucose tolerance test in diet induced obese mice.

GLP-1 MMB lowers blood glucose following an oral glucose tolerance test (OGTT) in diet induced obese mice. To develop a murine model of diet induced obesity, mice were maintained on a high fat diet for at least 27 weeks. Mice became obese and were determined to be diabetic when fasting blood glucose values exceeded 120 mg/dl. To evaluate the effect of GLP-1 MMB therapy on postprandial blood glucose levels, diet induced obese mice were fasted overnight and dosed subcutaneously with 0.02, 0.2, or 2 mg/kg GLP-1 MMB of SEQ ID NO: 71 or vehicle control. Six hours after dosing, mice were given a 1.5 mg/g gastric gavage of glucose. Blood glucose levels were determined prior to MMB dosing, at t=0, 15, 30, 60, 90, 120, 150, and 180 minutes using tail vein blood. As shown in FIG. 16, GLP-1 MMB of SEQ ID NO: 71 dose dependent decrease in fasting blood glucose values was observed at t=0 and all subsequent time points. Areas under the curve were calculated between t=0 and t=180 demonstrating a significant lowering in glucose disposal at all doses.

Similar experiments were repeated for the GLP-1 MMB of SEQ ID NO:4 and similar results were obtained.

EXAMPLE 21

Figure 17A:
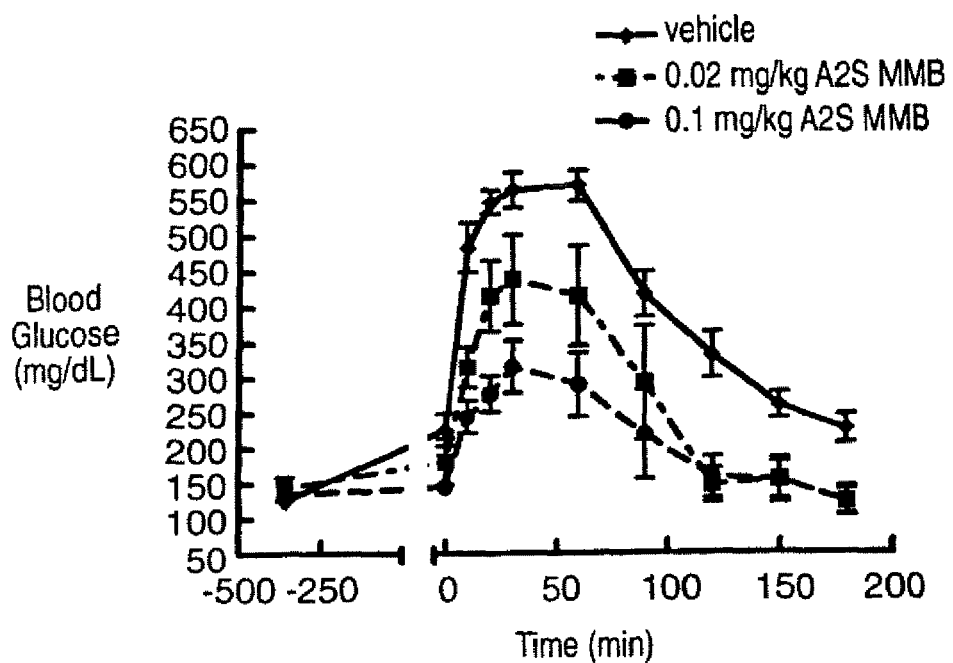
FIG. 17 demonstrates that GLP-1 MMB lowers blood glucose (FIG. 17A) and lowers insulin level (FIG. 17B) in an intraperitoneal glucose tolerance test in diabetic mice.
Figure 17B:
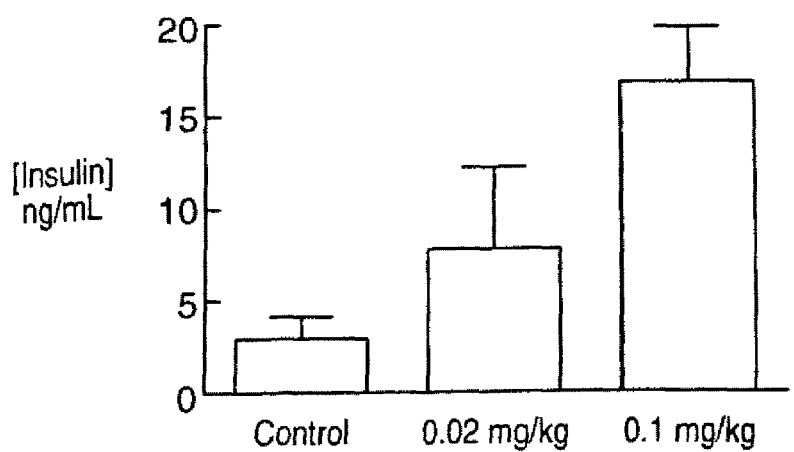

GLP-1 MMB lowers blood glucose in an intraperitoneal glucose tolerance test (IPGTT) in db/db mice. Male db/db mice of approximately 13-15 weeks of age were randomized into treatment groups of six mice based on fasting blood glucose levels. Mice were dosed with either 0.02 mg/kg or 0.1 mg/kg of GLP-1 MMB of SEQ ID NO: 71 or 0.1 mg/kg of negative control MMB six hours prior to the glucose tolerance test. Five minutes before the glucose tolerance test, a glucose measurement was taken with a hand held glucometer from tail vein blood. Mice were then dosed intraperitoneally with 1 mg/g of D-glucose and blood glucose levels were monitored at 10 min, 20 min, 30 min, 60 min, 90 min, 120 min, 150 min, and 180 min. As illustrated in FIG. 17A, blood glucose levels were significant lower in both groups treated with GLP-1 MMB of SEQ ID NO: 71 over the full time course. Additional groups of animals treated in the same manner were sacrificed for measurement of insulin levels at t=10 minutes. There is a dose dependent increase in the amount of insulin released 10 minutes following GLP-1 MMB of SEQ ID NO: 71 dosing.

Similar experiments were repeated for the GLP-1 MMB of SEQ ID NO:4 and similar results were obtained.

EXAMPLE 22

Acute Pharmodynamic Study with GLP-1 MMB. To demonstrate biological activity of a GLP-1 MMB of SEQ ID NO 4, an intraperetoneal glucose tolerance test (ipGTT) was performed in diet-induced obese (DIO) mice.

Materials/Methods: D-glucose was purchased from Sigma. The studies described below used diet-induced obese (DIO) C57B1/6J mice that were started on a diet containing 60.9% fat (Purina TestDiets 58126) at 4 weeks of age. All animals achieved three consecutive weeks of diabetic fasting blood glucose values (>120 mg/dL) prior to their inclusion in the study. ipGTT: Thirty-five mice were fasted overnight (16 hr) and were randomized into 7 groups (n=5) based upon their fasting glucose concentrations. Ten minutes prior to the glucose tolerance test, mice were dosed i.v. with PBS or GLP1 MMB of SEQ ID NO 4 (0.003, 0.01, 0.03, 0.1, 0.3, and 1.0 mg/kg). Five minutes prior to the glucose tolerance test, a fasting glucose measurement was made from tail vein blood. At T=0 min, mice were dosed i.p. with D-glucose (1.0 mg/g). Blood glucose levels were measured at 15, 30, 60, 90, 120, 150 and 180 min using tail vein blood.

Figure 21A:
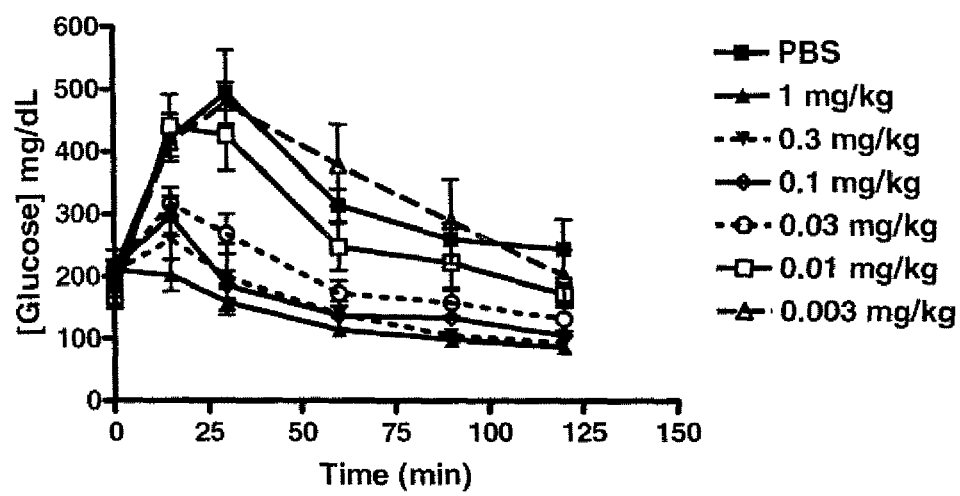
FIG. 21A demonstrates ipGTT in DIO mice dosed with GLP-1 MMB.
Figure 21B:
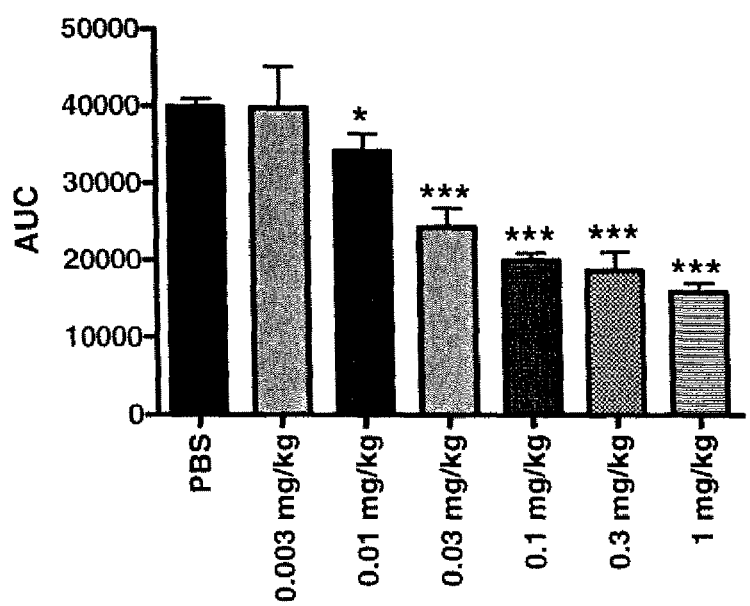
FIG. 21B demonstrates calculated area under the curve (AUC) for ipGTT presented in FIG. 1
Figure 21C:
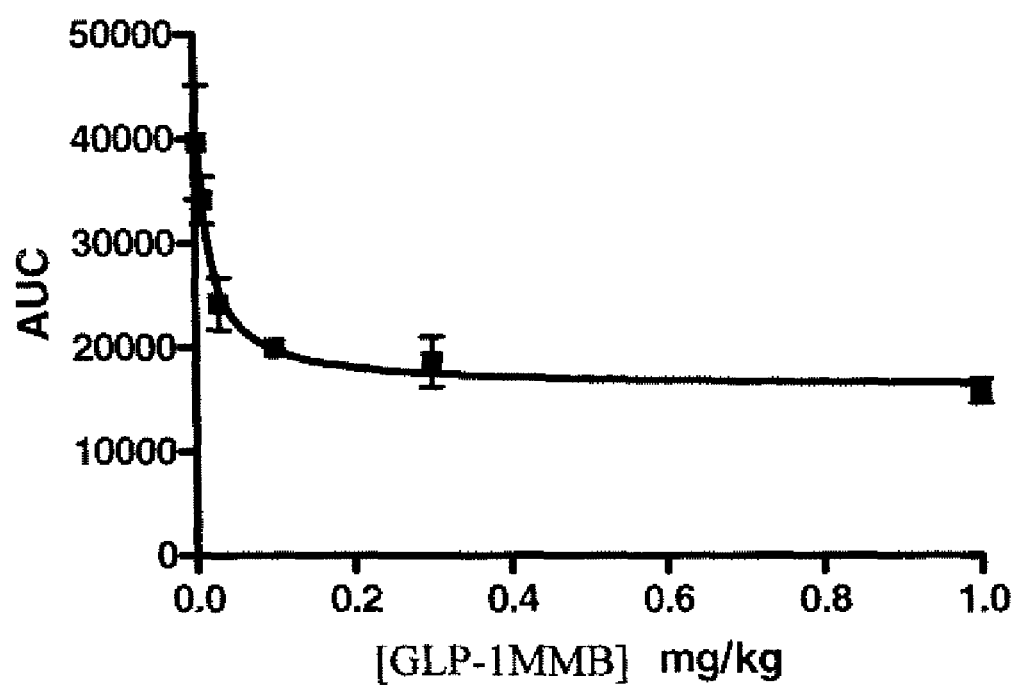
FIG. 21C demonstrates the data from FIG. 2 were fit to a hyperbola, providing an $ED_{50}$ of 15 µg/kg.

Results: The blood glucose levels measured during the glucose tolerance test were plotted as a function of time (FIG. 21A). The area under the curve was calculated and was significantly reduced in a dose dependent manner in five of the groups treated with GLP-1 MMB of SEQ ID NO 4 (0.01, 0.03, 0.1, 0.3, 1 mg/kg) relative to the PBS-treated group (FIG. 21B). The AUC vs GLP-1 MMB of SEQ ID NO 4 concentration was fit to a hyperbola, providing an $ED_{50}$ of 14 µg/kg (FIG. 21C). Data was plotted and analyzed in GraphPad PRISM, version 4.03.

EXAMPLE 23

Effect of a GLP-1 MMB on Food Intake, Glycemic Control and Gastric Emptying in GLP-1R−/− and Wild-Type Mice. The purpose of this study was to evaluate if a GLP-1 MMB affects glycemic control, food intake and gastric emptying in a GLP-1 receptor-dependent manner. Single intravenous (iv) administration of a GLP-1 MMB of SEQ ID NO 4 improved glucose tolerance, reduced food intake and inhibited gastric emptying in wild type, but not in GLP-1 receptor knock out mice. The results demonstrate that the effect of a GLP-1 MMB of SEQ ID NO 4 on glucose and energy metabolism is mediated via the GLP-1 receptor.

Materials/Methods: Animals: Male GLP-1R−/− and age matched wild type mice were randomized into three treatment groups (n=5) based on body weight and fasting blood glucose.

Food intake: Mice were fasted overnight and injected with a single intravenous (iv) dose of a GLP-1 MMB of SEQ ID NO 4 (1 mg/kg), CNTO 1996 (1 mg/kg) (CNTO1996 was used in the study as a negative control since it lacks the GLP-1 peptide and an equimolar dose of exendin-4 (0.07 mg/kg, purchased from Sigma). Food and water intake was measured 4, 6, 24 and 48 h post dosing.

Glucose tolerance test (ipGTT): Mice were fasted overnight and dosed intravenously as discussed above. Fasting glucose was measured via tail snips using a hand-held glucometer (LifeScan). At t=0 min, mice were dosed i.p. with D-glucose (1.0 mg/g, Sigma) and blood glucose was measured after 15, 30, 60, 90 and 120 min using tail vein blood Gastric Emptying: Mice were fasted overnight. The next morning mice were re-fed for 1 h, food intake was recorded and the mice were deprived of food for the rest of the study. Mice were dosed intravenously as discussed above. Two hours post-dosing mice were euthenized.

The stomach was exposed by laparotomy, ligated at both the pylorus and cardia and removed.

The stomach content wet weight was measured. Equation 1 was used to calculate the percent of food remaining in the stomach.

$$\text{(Stomach Content Wet Weight (g)/Food Intake (g))} *100 \quad \text{Equation (1)}$$

Results And Discussion

Figure 22A:
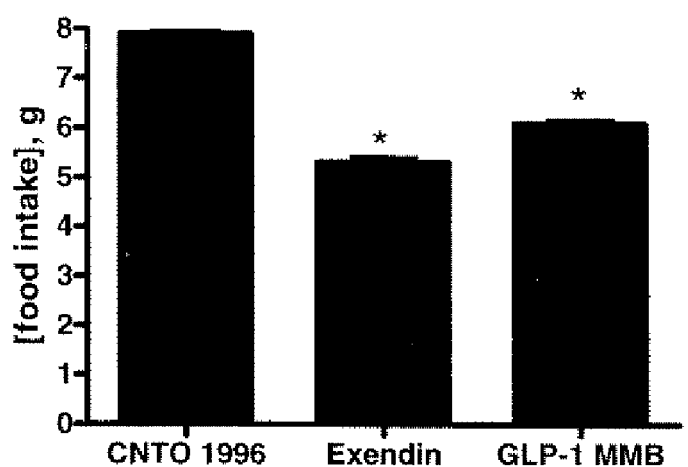
FIGS. 22A and B demonstratre 24 hour cumulative food intake in wild type (A) and GLP-1R-/- (B) mice treated with a single iv dose of CNTO1996 (1 mg/kg), exendin-4 (0.07 mg/kg) and GLP-1 MMB (1 mg/kg). Values represent mean±SE; *p<0.05 vs. CNTO1996-treated group.
Figure 22B:
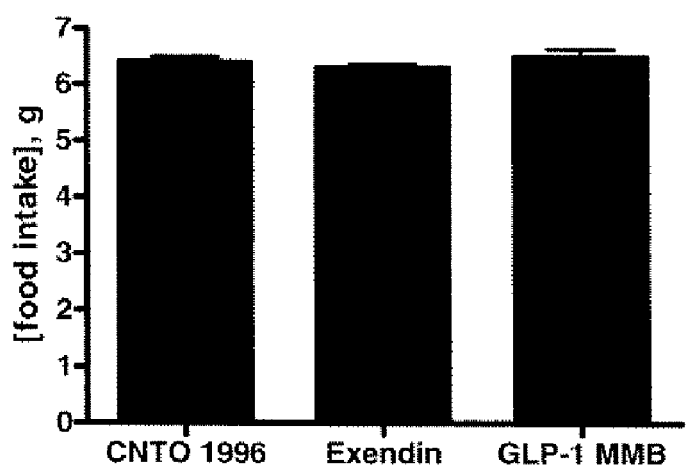

Food Intake: Cumulative food intake for both the wild-type and GLP-1R−/− mice over a 24 hour period post drug administration was plotted (FIG. 22). Both the GLP-1 MMB of SEQ ID NO 4 (1 mg/kg) and an equimolar dose of exendin4 (0.07 mg/kg) resulted in a statistically significant reduction in food intake in wild type animals compared to the control group, CNTO1996 (FIG. 22A). The GLP-1 MMB of SEQ ID NO 4 and exendin-4 had no effect on food intake in GLP-1R−/− mice (FIG. 22B).

Figure 23A:
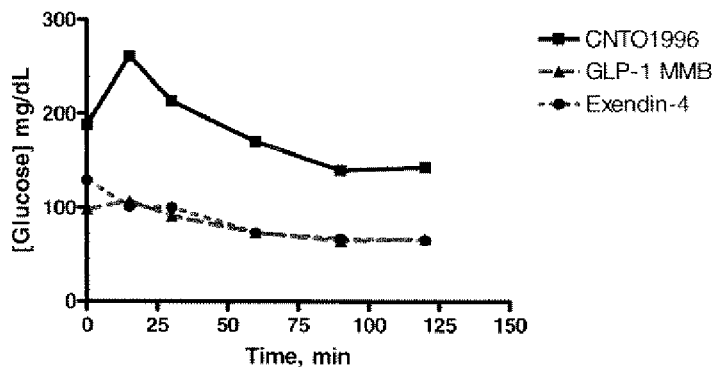
FIGS. 23A, B, and C, demonstrate glucose tolerance test in wild type (A) and GLP-1R-/- (B) mice following a single iv dose of CNTO1996 (1 mg/kg), exendin-4 (0.07 mg/kg) and GLP-1 MMB (1 mg/kg). (C) Area under the curve for ipGTT tests in wild type (black bar) and GLP-1R-/- (grey bar) mice. Values represent mean±SE; *p<0.05 vs. CNTO1996-treated group.
Figure 23B:
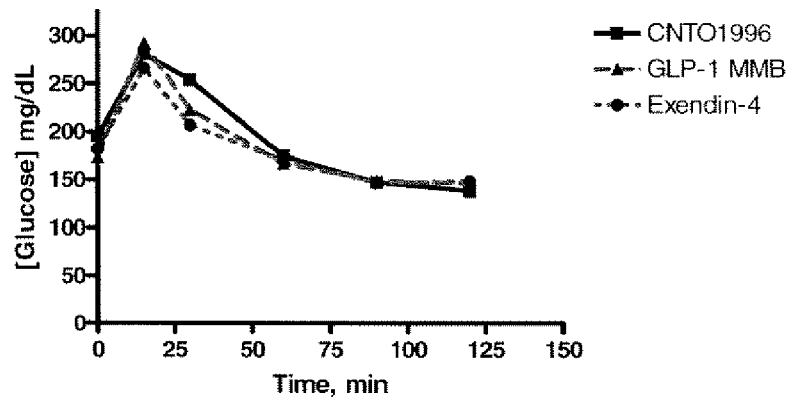
Figure 23C:
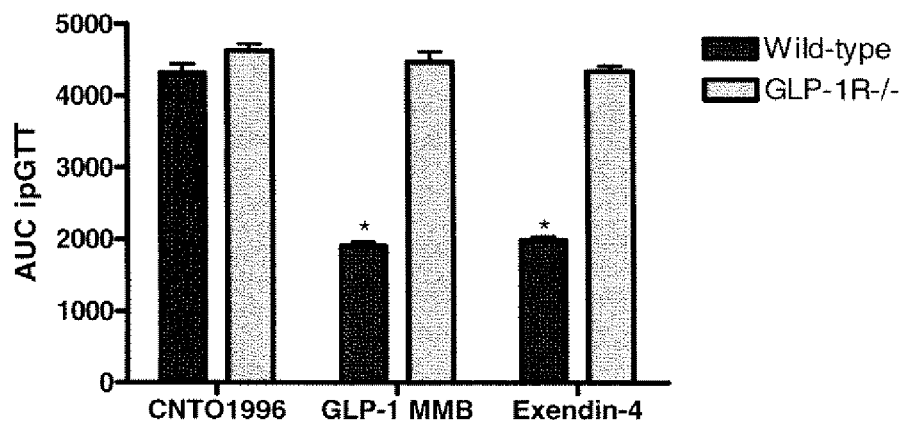
Figure 24:
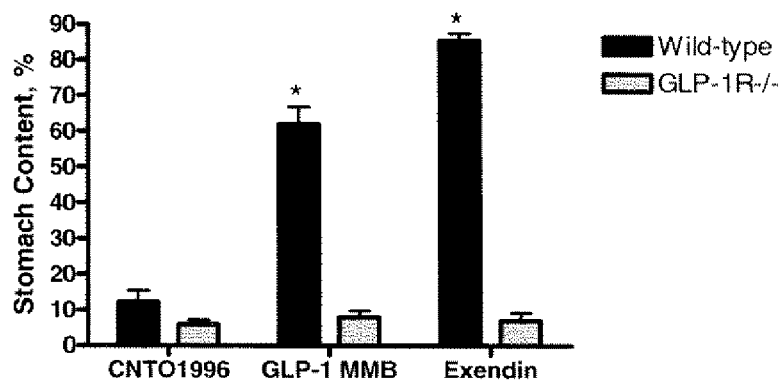
FIG. 24 demonstrates stomach content in wild type (black bars) and GLP-1R-/- (grey bars) mice treated with CNTO1996 (1 mg/kg), exendin-4 (0.07 mg/kg) and GLP-1 MMB (1 mg/kg). Values represent mean±SE; *p<0.05 vs. CNTO1996-treated group.

Glucose Tolerance Test: The data obtained during the ipGTT in wild type and GLP-1R−/− mice was plotted as the concentration of blood glucose versus time (FIGS. 23A and 23B). The area under the curve (AUC) was calculated for each individual ipGTT curve (FIG. 23C). Single administration of a GLP-1 MMB of SEQ ID NO 4 and exendin-4 resulted in a statistically significant reduction in the AUC in wild type but not GLP-1R−/− animals Gastric emptying: The percent of food remaining in the stomach 2 h after dosing in wild type and GLP-1R−/− mice was plotted (FIG. 24). The GLP-1 MMB of SEQ ID NO 4 (1 mg/kg) and an equimolar dose of exendin-4 (0.07 mg/kg) resulted in a statistically significant increase in stomach content in the wild-type mice compared to the control, CNTO1996. The data demonstrate that the GLP-1 MMB of SEQ ID NO 4 and exendin-4 inhibit gastric emptying in wild type animals. The GLP-1 MMB of SEQ ID NO 4 and exendin-4 had no effect on gastric emptying in the GLP-1R−/− mice.

EXAMPLE 24

Correlation of the Pharmacodynamic Activity of a GLP-1 MMB with its Pharmacokinetic Profile in DIO Mice. The purpose of this study was to correlate the effect of a GLP-1 MMB in regulating glucose tolerance with its pharmacokinetic profile in diet-induced obese (DIO) mice. Animals were dosed (iv) with a GLP-1 MMB of SEQ ID NO 4 (1 mg/kg) and glucose tolerance tests were performed at various time post dosing. Simultaneously, blood samples were collected to assess GLP-1 MMB of SEQ ID NO 4 levels. The GLP-1 MMB of SEQ ID NO 4 improved glucose tolerance in DIO mice with an $ED_{50}$ of approximately 370 ng/ml.

Materials/Methods. Animals/Treatments: C57B1/6J mice were started at 4 weeks of age on a diet containing 60.9% fat (Purina TestDiets 58126). At the time of the study start, all of the animals had achieved three consecutive weeks of diabetic fasting blood glucose values (>120 mg/dL). DIO mice were randomized into treatment groups based on fasting blood glucose and and were dosed (iv) with GLP-1 MMB of SEQ ID NO 4 (1 mg/kg, lot#8833173) ) or PBS. At various time post-dosing, glucose tolerance tests were performed and blood samples were collected to measure GLP-1 MMB of SEQ ID NO 4 plasma levels as described below.

Glucose tolerance test (ipGTT): Mice were fasted overnight (16 hr) before the test. In the morning a fasting glucose was measured via tail snips using a hand-held glucometer (LifeScan). At T=0 min, mice were dosed i.p. with D-glucose (1.0 mg/g, Sigma). Blood glucose was measured after 15, 30, 60, 90 and 120 min using tail vein blood.

GLP-1 MMB plasma levels: Blood samples were collected after the ipGTT via cardiac puncture. Approximately 300 µl of blood was collected in sodium citrate (3.8%) containing protease inhibitors (Roche Complete EDTA free, Roche Applied Science, Indianapolis, Ind.) and DPP4 inhibitors (Linco, St. Charles, Mo.). The concentration of intact GLP-1 MMB of SEQ ID NO 4 was measured using a mesoscale discovery (MSD) technology [2-5]. Briefly, plasma samples were serially diluted by a BioMek Fx for a total of 4 dilutions, neat, 1:8, 1:64 and 1:512. Standard curves diluted in the same manner with plasma were included on each plate. GLP-1 MMB was captured on the MSD plates by a biotinylated monoclonal antibody (CNTO1626) designed to detect the intact N-terminus of the mimetibody. A ruthenium labeled monoclonal antibody recognizing the linker region of the mimetibody (CNTO712) was added for detection, and the luminescence responses were determined using the MSD sector imager 6000 reader. GLP-1 MMB of SEQ ID NO 4 level was calculated using sigmoidal dose-response curve (GraphPad PRISM).

Figure 25:
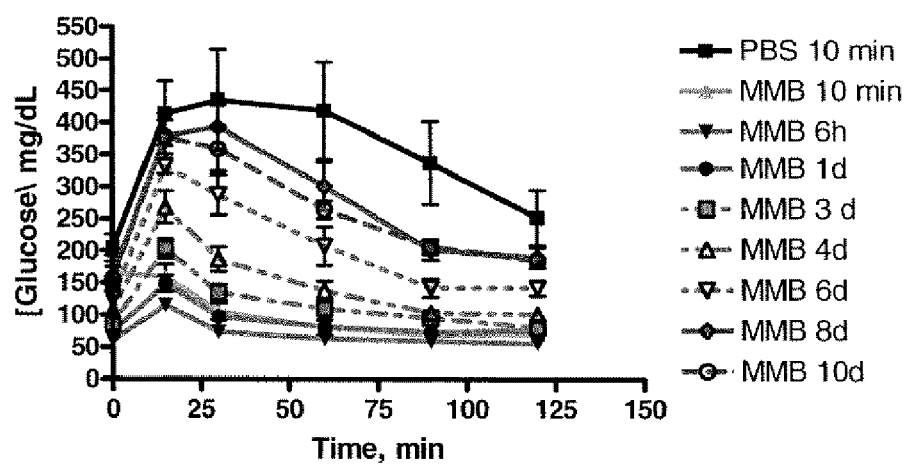
FIG. 25 demonstrates glucose tolerance test in DIO mice performed at various time points following single iv administration of a GLP-1 MMB (1 mg/kg).
Figure 26:
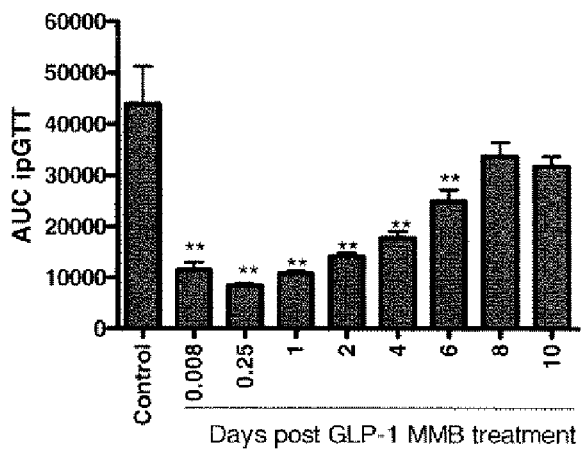
FIG. 26 demonstrates the area under the curve for data obtained during the ipGTT in DIO mice (FIG. 25).

Results And Discussion. Pharmacodynamics of a GLP-1 MMB: The ipGTT data from each time point was plotted as the concentration of blood glucose versus time (FIG. 25). The area under the curve (AUC) was calculated for each individual ipGTT curve (FIG. 26). Single administration of the GLP-1 MMB of SEQ ID NO 4 resulted in a statistically significant reduction in the AUC up to 6 days post injection relative to the negative control.

Figure 27:
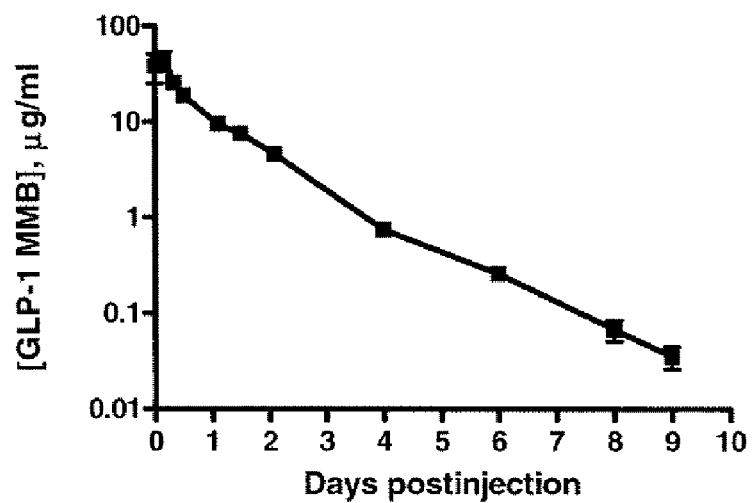
FIG. 27 demonstrates GLP-1 MMB levels in DIO mice plasma following single iv administration (1 mg/kg).

Pharmacokinetics of GLP-1 MMB: The plasma concentration of the GLP-1 MMB of SEQ ID NO 4 in DIO mice following each glucose tolerance test was plotted (FIG. 27).

Figure 28:
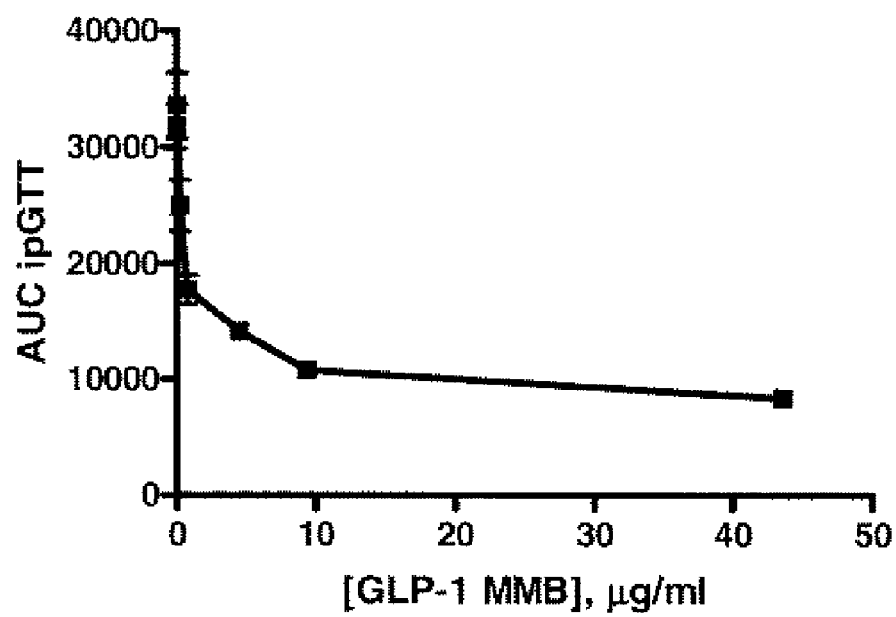
FIG. 28 demonstrates the area under the curve for the glucose tolerance test following single iv administration of a GLP-1 MMB (1 mg/kg) plotted as a function of the GLP-1 MMB plasma concentration immediately after the glucose tolerance test.

Correlation of pharmacodynamic activity of GLP-1 MMB with its plasma levels: The AUC for all of the ipGTT data was plotted versus the GLP-1 MMB of SEQ ID NO 4 plasma levels following each glucose tolerance test (FIG. 28). The data were fit to a hyperbola to obtain the $ED_{50}$ (370 ng/ml).

Advantages of GLP-1 Mimetibody: The use of this novel molecule as a therapeutic to treat type 2 diabetes provides several advantages over other GLP-1 analogues. For example, it is likely to prolong the half-life of the GLP-1 peptide. Also, the wild-type GLP-1 peptide in the mimetibody scaffold is resistant to protease degradation, specifically DPP-IV. This may allow for treatment with the wild-type GLP-1 peptide rather than a mutant peptide. Since GLP-1 is a native peptide, there may be less immune response in patients treated with a GLP-1 mimetibody than in patients treated with a mutated GLP-1 analogue. In addition, the large size of the mimetibody may preclude it from crossing the blood brain barrier. This may offer an advantage since nausea and anxiety have been associated with GLP-1 engaging the GLP-1R in the brain. Furthermore, the mimetibody platform results in expression of two peptides on each mimetibody molecule. This may allow the GLP-1 peptides to interact with each other, forming a dimeric ligand that could increase affinity to the cell surface GLP-1 receptor.

It will be clear that the invention can be practiced otherwise than as particularly described in the foregoing description and examples.

Numerous modifications and variations of the present invention are possible in light of the above teachings and, therefore, are within the scope of the present invention.

TABLE 1

| SEQ ID NO | | | TOTAL AA NO | REGIONS | |
|---|---|---|---|---|---|
| | | | | FR1 | FR4 |
| 47 | Heavy | Vh1 | 125 | 1-31 | 81-125 |
| 48 | chain | Vh2 | 97 | 1-30 | 80-97 |
| 49 | variable | Vh3a | 102 | 1-30 | 80-102 |
| 50 | region | Vh3b | 102 | 1-30 | 80-102 |
| 51 | | Vh3c | 94 | 1-30 | 80-94 |
| 52 | | Vh4 | 106 | 1-30 | 80-106 |
| 53 | | Vh5 | 97 | 1-30 | 80-97 |
| 54 | | Vh6 | 91 | 1-30 | 80-91 |
| 55 | | Vh7 | 91 | 1-30 | 80-91 |

| SEQ ID NO | | | AA NO | REGIONS | | | | | | |
|---|---|---|---|---|---|---|---|---|---|---|
| | | | | hinge1 | hinge2 | hinge3 | hinge4 | CH2 | CH3 | CH4 |
| 56 | Heavy | IgA1 | 354 | 103-122 | | | | 123-222 | 223-354 | |
| 57 | chain | IgA2 | 340 | 103-108 | | | | 109-209 | 210-340 | |
| 58 | constant | IgD | 384 | 102-135 | 319-497 | | | 160-267 | 268-384 | |
| 59 | region | IgE | 497 | | | | | 104-210 | 211-318 | 319-497 |
| 60 | | IgG1 | 339 | 99-121 | | | | 122-223 | 224-339 | |
| 61 | | IgG2 | 326 | 99-117 | | | | 118-219 | 220-326 | |
| 62 | | IgG3 | 377 | 99-115 | | 131-145 | 146-168 | 169-270 | 271-377 | |
| 63 | | IgG4 | 327 | 99-110 | 324-476 | | | 111-220 | 221-327 | |
| 64 | | IgM | 476 | | | | | 105-217 | 218-323 | 324-476 |

The invention claimed is:

1. A mimetibody comprising a polypeptide having the sequence shown in SEQ ID NO: 7.

2. A pharmaceutical composition comprising an effective amount of the mimetibody of claim 1 and a pharmaceutically acceptable carrier of diluent.

* * * * *